(12) United States Patent
Mori et al.

(10) Patent No.: US 7,202,040 B2
(45) Date of Patent: Apr. 10, 2007

(54) METHOD FOR SCREENING COMPOUNDS WHICH CHANGE THE BINDING PROPERTIES OF A PROTEIN WITH A LIGAND

(75) Inventors: Masaaki Mori, Ibaraki (JP); Tomoko Chikatsu, Ibaraki (JP); Shuji Sato, Ibaraki (JP); Toshimi Nagi, Ibaraki (JP); Tsukasa Sugo, Ibaraki (JP)

(73) Assignee: Takeda Pharmaceutical Company Limited, Osaka (JP)

(*) Notice: Subject to any disclaimer, the term of this patent is extended or adjusted under 35 U.S.C. 154(b) by 215 days.

(21) Appl. No.: 10/499,172

(22) PCT Filed: Dec. 13, 2002

(86) PCT No.: PCT/JP02/13096

§ 371 (c)(1),
(2), (4) Date: Jun. 14, 2004

(87) PCT Pub. No.: WO03/052414

PCT Pub. Date: Jun. 26, 2003

(65) Prior Publication Data

US 2005/0154190 A1    Jul. 14, 2005

(30) Foreign Application Priority Data

Dec. 14, 2001  (JP) ............................ 2001-382174
Jul. 9, 2002    (JP) ............................ 2002-200556

(51) Int. Cl.
*G01N 33/53* (2006.01)
*G01N 33/00* (2006.01)
*C12Q 1/68* (2006.01)
*C12N 15/00* (2006.01)
*A61K 38/02* (2006.01)
*A61K 38/16* (2006.01)

(52) U.S. Cl. ..................... 435/7.1; 435/7.2; 435/7.8; 435/7.93; 435/6; 435/975; 435/320.1; 530/300

(58) Field of Classification Search .............. 435/6, 435/7.1, 7.21, 7.8, 7.93, 961, 975, 7.2, 320.1; 436/544, 545, 546, 71, 103; 530/300, 359
See application file for complete search history.

(56) References Cited

U.S. PATENT DOCUMENTS 6,291,177 B1 * 9/2001 Madden et al. ............... 435/6

OTHER PUBLICATIONS

T. Schoneberg et al., "A Novel Subgroup of Class I G-Protein-Coupled Receptors", Biochimica et Biophysica Acta, vol. 1446, pp. 57-70 (1999).
A. Marchese et al., "Discovery of Three Novel Orphan G-Protein-Coupled Receptors", Genomics, vol. 56, pp. 12-21 (1999).
T. Martin et al., "Interactions of Lysophospholipids and Mast Cells", Nature, vol. 279, pp. 250-252 (1979).
G.A. Smith et al., "The Exogenous Lipid Requirement for Histamine Release From Rat Peritoneal Mast Cells Stimulated by Concanavalin A", FEBS Letters, vol. 105, No. 1, pp. 58-62 (1979).
A. Bruni et al., "Interaction Between Nerve Growth Factor and Lysophosphatidylserine on Rat Peritoneal Mast Cells", FEBS Letters, vol. 138, No. 2, pp. 190-192 (1982).
F. Bellini et al., "Role of a Serum Phospholipase $A_1$ in the Phosphatidylserine-Induced T Cell Inhibition", FEBS Letters, vol. 316, No. 1, pp. 1-4 (1993).
S. Lourenssen et al., "Lysophosphatidylserine Potentiates Nerve Growth Factor-Induced Differentiation of PC12 Cells", Neuroscience Letters, vol. 248, pp. 77-80 (1998).
V. Fadok et al., "A Receptor for Phosphatidylserine-Specific Clearance of Apoptotic Cells", Nature, vol. 405, pp. 85-90 (2000).
NCBI Sequence Viewer, Accession No. AAD50550, "G protein-coupled receptor Gpr34 [Mus musculus]" (1999).

* cited by examiner

*Primary Examiner*—Long V. Le
*Assistant Examiner*—Shafiqul Haq
(74) *Attorney, Agent, or Firm*—David G. Conlin; Christine C. O'Day; Edwards Angell Palmer & Dodge LLP

(57) ABSTRACT

The present invention relates to a screening method/screening kit for screening a compound or its salt that changes the binding properties of (a) a protein containing the same or substantially the same amino acid sequence as the amino acid sequence represented by SEQ ID NO: 1 or SEQ ID NO: 19, its partial peptides, or salts thereof, and (b) a ligand capable of binding specifically to the protein; compounds obtained by the screening or salts thereof; pharmaceuticals comprising the compounds or salts thereof; a protein containing the same or substantially the same amino acid sequence as the amino acid sequence represented by SEQ ID NO: 19; etc. The compounds obtained by the screening of the present invention are useful as agents for the prevention/treatment of, for example, neurodegenerative diseases, immunological diseases, edema, acid indigestion, etc.

22 Claims, 2 Drawing Sheets

METHOD FOR SCREENING COMPOUNDS WHICH CHANGE THE BINDING PROPERTIES OF A PROTEIN WITH A LIGAND

RELATED APPLICATIONS

This is a US national phase filing under 35 U.S.C. § 371 of PCT/JP02/13096 filed Dec. 13, 2002 and claims priority from JP 2001-382174 filed Dec. 14, 2001 and JP 2002-200556 filed Jul. 9, 2002.

TECHNICAL FIELD

The present invention relates to a screening method and screening kit for pharmaceuticals using a receptor and a ligand capable of binding specifically to the receptor, compound obtainable by the screening method or kit, novel receptors, etc. More particularly, the present invention relates to a screening method and screening kit for screening agents for the prevention/treatment of neurodegenerative diseases, immunological diseases, edema, acid indigestion, etc.

BACKGROUND ART

Important biological functions including maintenance of homeostasis in vivo, reproduction, development of individuals, metabolism, growth, control of the nervous, circulatory, immune, digestive or metabolic system, sensory adaptation, etc. are regulated by cells that receive endogenous factors such as various hormones and neurotransmitters or sensory stimulation like light or odor, via specific receptors present on cell membranes reserved for these factors or stimulation and interact with them. Many of these receptors for hormones or neurotransmitters by such functional regulation are coupled to guanine nucleotide-binding proteins (hereinafter, sometimes merely referred to as G proteins), and are characterized by developing a variety of functions through mediation of intracellular signal transduction via activation of the G proteins. In addition, these receptor proteins possess common seven transmembrane domains. Based on the foregoing, these receptors are thus collectively referred to as G protein-coupled receptors or seven transmembrane receptors. As such it is known that various hormones or neurotransmitters and their receptors are present and interact with each other to play important roles for regulating the biological functions. However, it often remains unclear if there are any other unknown substances (hormones, neurotransmitters, etc.) and receptors to these substances.

In the G protein-coupled receptors, ligands to some receptors that are subtypes having high homology in structure to known receptors may be readily predictable but in most cases, their endogenous ligands are unpredictable so that ligands corresponding to these receptors are hardly found. For this reason, these receptors are termed orphan receptors. It is likely that unidentified endogenous ligands to such orphan receptors would take part in biological phenomena poorly analyzed because the ligands were unknown. When such ligands are associated with important physiological effects or pathologic conditions, it is expected that development of these receptor agonists or antagonists will result in breakthrough new drugs (Stadel, J. et al., TiPS, 18, 430–437, 1997; Marchese, A. et al., TiPS, 20, 370–375, 1999; Civelli, O. et al., Brain Res., 848, 63–65, 1999, Howard, A. D. et al., TiPS, 22, 132–140, 2001).

Orphan receptors and ligands thereto often take part in a new physiological activity, and it is expected that their clarification will lead to development of new drugs. However, it is known that research on ligands to orphan receptors is accompanied by many difficulties. For example, it is generally unknown what secondary signal transduction system will take place after orphan receptors expressed on cells responded to ligands, and various response system should be examined. Moreover, tissues where ligands are present are not readily predictable so that various tissue extracts should be prepared. Furthermore, since an amount of ligand required to stimulate its receptor is sufficient even in an extremely low level when the ligand is a peptide, the amount of such a ligand present in vivo is a trace amount in many cases. In addition, a peptide is digested by peptidase to lose its activity, or undergoes non-specific adsorption so that its recovery becomes poor during purification. Thus, it is normally extremely difficult to extract such a ligand from the living body and isolate the necessary amount of the ligand for determination of its structure. The presence of many orphan receptors was unraveled, but only a very small part of the ligands to these receptors were discovered so far due to the foregoing problems.

GPR34 (SEQ ID NO: 1) (Genomics, 56, 12–21, 1999; Biochim. Biophys. Acta, 1446, 57–70, 1999), reported as an orphan G protein-coupled receptor, showed 26 to 31% homology to RSC338, RBintron, GPR23 or GPR17, which is a orphan receptor, and a poor (25% or less) homology to platelet-activating factor and uridine diphosphate glycoside, but is totally unknown for its ligand.

On the other hand, it is known that lysophosphatidylserine (hereinafter sometimes simply referred to as lyso-PS) has the histamine release activity on rat mast cells stimulated by an antigen or concanavalin A (Nature, 279, 250–252, 1979; FEBS Lett., 105, 58–62, 1979), the activity of releasing histamine by synergistically acting on rat mast cells together with nerve growth factor (NGF) (FEBS Lett., 138, 190–192, 1982), the growth regulating activity on human T cells (FEBS Lett., 316, 1–4, 1993), and the activity of potentiating the differentiation-inducing ability of NGF on PC12 cells (Neurosci. Lett., 248, 77–80, 1998). Since these actions are specific to lyso-PS and are observed in a relatively low level, it is predicted that specific receptors would mediate the actions. However, there is no report on identification of these receptors so far.

Phosphatidylserine (hereinafter sometimes simply referred to as PS) is known from old to inhibit blood coagulation or platelet agglutination response. Recently, it was demonstrated that PS was exposed on the cell surface of apoptotic cells and a receptor capable of recognizing PS is engaged in clearance of the apoptotic cells (Nature, 405, 85–90, 2000). However, the receptor is distinct from GPR34.

It has been desired to find a ligand to GPR34 and utilizing the screening system for pharmaceuticals using the ligand, thereby to develop pharmaceuticals having entirely a new mechanism of action.

DISCLOSURE OF THE INVENTION

In order to solve the foregoing problems, the present inventors have made extensive investigations and found that lyso-PS exhibits a marked intracellular cAMP production-suppressing activity on GPR34-expressed CHO cells, PS in its high level shows a marked intracellular cAMP production-suppressing activity on GPR34-expressed CHO cells and moreover, lyso-PS and PS are endogenous ligands extremely highly specific to GPR34. A variety of the above-mentioned physiological activities displayed by lyso-PS indicate that lyso-PS possesses critical physiological functions in immune actions such as inflammation, etc., central nervous action such as neuronal regeneration, etc. and disorders associated therewith, and it has also been found that by using lyso-PS or the like and GPR34, it becomes possible to survey pharmaceuticals effective for immune disorders, central nervous disorders, etc. Based on these findings, further extensive investigations have been made so that the present invention has come to be accomplished.

That is, the present invention provides the following features.

(1) A method of screening a compound or its salt that changes the binding properties of a protein containing the same or substantially the same amino acid sequence as the amino acid sequence represented by SEQ ID NO: 1 or SEQ ID NO: 19 (hereinafter sometimes merely referred to as the receptor of the present invention) or its salt, to a ligand capable of binding specifically to the protein or its salt, which comprises using (a) the protein, its partial peptide, or a salt thereof, and (b) the ligand;

(2) The screening method according to (1), wherein the ligand is a lipid;

(3) The screening method according to (1), wherein the ligand is an ether phospholipid, a phosphono-ether lipid, a glycerophospholipid, a phosphono-glycerolipid, a sphingolipid, a sphingophospholipid or a phosphonosphingolipid;

(4) The screening method according to (1), wherein the ligand is a compound represented by the formula below (hereinafter sometimes merely referred to as Compound (I));

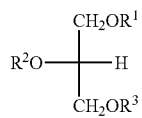

[wherein $R^1$ represents hydrogen atom, a hydrocarbon group which may optionally have a substituent(s), or an acyl;

each of $R^2$ and $R^3$ represents hydrogen atom, a hydrocarbon group which may optionally have a substituent(s), an acyl, or a group represented by the formula below (hereinafter sometimes merely referred to as Group (III));

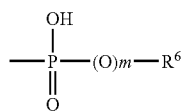

(wherein $R^6$ represents hydrogen atom, an alkyl which may optionally have a substituent(s), or a cycloalkyl which may optionally have a substituent(s), and m is 0 or 1)] or a salt thereof);

(5) The screening method according to (4), wherein $R^1$ is an acyl;

(6) The screening method according to (4), wherein $R^2$ is hydrogen atom or an acyl;

(7) The screening method according to (4), wherein $R^3$ is group (III);

(8) The screening method according to (4), wherein $R^6$ is an alkyl or cycloalkyl, each of which may optionally have a substituent(s) selected from hydroxy, carboxy, amino and an alkylammonio;

(9) The screening method according to (7), wherein $R^6$ is 2-amino-2-carboxyethyl;

(10) The screening method according to (9), wherein each of $R^1$ and $R^2$ is a hydrocarbon group or an acyl, and m is 1;

(11) The screening method according to (1), wherein the ligand is a compound represented by the formula below:

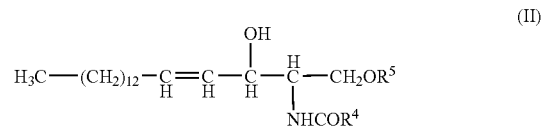

[wherein $R^4$ represents hydrogen atom, a hydrocarbon group which may optionally have a substituent(s), or an acyl; and, $R^5$ represents hydrogen atom, a hydrocarbon group which may optionally have a substituent(s), an acyl, or a group represented by the formula below (hereinafter sometimes merely referred to as Group (IV));

(wherein $R^7$ represents hydrogen atom, an alkyl which may optionally have a substituent(s), or a cycloalkyl which may optionally have a substituent(s) and n is 0 or 1)] or a salt thereof;

(12) The screening method according to (1), wherein the ligand is lysophosphatidylserine or phosphatidylserine;

(13) The screening method according to (1), wherein the protein containing the same or substantially the same amino acid sequence as the amino acid sequence represented by SEQ ID NO: 1 is a protein containing the amino acid sequence represented by SEQ ID NO: 22;

(14) The screening method according to (1), wherein the protein consisting of the amino acid sequence represented by SEQ ID NO: 1 or a salt thereof is used;

(15) The screening method according to (1), wherein the protein consisting of the amino acid sequence represented by SEQ ID NO: 19 or a salt thereof is used;

(16) The screening method according to (1), wherein the binding amount of the ligand capable of binding specifically to the protein containing the same or substantially the same amino acid sequence as the amino acid sequence represented by SEQ ID NO: 1 or SEQ ID NO: 19, or its partial peptide, or a salt thereof, to the protein, its partial peptide, or a salt thereof, is measured (a) when the ligand is brought in contact with the protein, its partial peptide, or a salt thereof and (b) when the ligand and a test compound are brought in contact with the protein, its partial peptide, or a salt thereof, and comparison is made between (a) and (b);

(17) The screening method according to (1), wherein the binding amount of the ligand capable of binding specifically to the protein containing the same or substantially the same amino acid sequence as the amino acid sequence represented by SEQ ID NO: 1 or SEQ ID NO: 19, or its partial peptide, or a salt thereof, to a cell containing the protein, its partial peptide, or a salt thereof, or a membrane fraction of the cell, is measured (a) when the ligand is brought in contact with the cell or its membrane fraction containing the protein, its partial peptide, or a salt thereof and (b) when the ligand and a test compound are brought in contact with the cell or its membrane fraction containing the protein, its partial peptide, or a salt thereof, and comparison is made between (a) and (b);

(18) The screening method according to (16), wherein the protein containing the same or substantially the same amino acid sequence as the amino acid sequence represented by SEQ ID NO: 1 or SEQ ID NO: 19, its partial peptide, or a salt thereof is a protein, its partial peptide, or a salt thereof, which is expressed on a cell membrane by culturing a transformant containing a DNA encoding the protein, its partial peptide, or a salt thereof;

(19) The screening method according to (16) to (18), wherein the ligand is a labeled ligand;

(20) The screening method according to (1), wherein the cell stimulating activity mediated by the protein containing the same or substantially the same amino acid sequence as the amino acid sequence represented by SEQ ID NO: 1 or SEQ ID NO: 19, its partial peptide, or a salt thereof is assayed (a) when the ligand capable of binding specifically to the protein, its partial peptide, or a salt thereof is brought in contact with the protein, its partial peptide, or a salt thereof and (b) when the ligand and a test compound are brought in contact with the protein, its partial peptide, or a salt thereof, and comparison is made between (a) and (b);

(21) The screening method according to (1), wherein the cell stimulating activity mediated by the protein containing the same or substantially the same amino acid sequence as the amino acid sequence represented by SEQ ID NO: 1 or SEQ ID NO: 19, its partial peptide, or a salt thereof is assayed (a) when the ligand capable of binding specifically to the protein, its partial peptide or a salt thereof is brought in contact with a cell containing the protein, its partial peptide, or a salt thereof, or a membrane fraction of the cell, and (b) when the ligand and a test compound are brought in contact with the cell containing the protein, its partial peptide, or a salt thereof, or its membrane fraction and comparison is made between (a) and (b);

(22) The screening method according to (20), wherein the protein containing the same or substantially the same amino acid sequence as the amino acid sequence represented by SEQ ID NO: 1 or SEQ ID NO: 19, its partial peptide, or a salt thereof, is a protein, its partial peptide or a salt thereof, which is expressed on a cell membrane by culturing a transformant containing a DNA encoding the protein, its partial peptide, or a salt thereof;

(23) A kit for screening a compound or its salt that changes the binding properties of a protein containing the same or substantially the same amino acid sequence as the amino acid sequence represented by SEQ ID NO: 1 or SEQ ID NO: 19, or a salt thereof, to a ligand capable of binding specifically to the protein or its salt, comprising (a) the protein or its salt and (b) the ligand;

(24) A compound or its salt, which is obtainable using the screening method according to (1) or the screening kit according to (23);

(25) The compound or its salt according to (24), wherein the compound is a compound or its salt that inhibits the binding of a protein containing the same or substantially the same amino acid sequence as the amino acid sequence represented by SEQ ID NO: 1 or SEQ ID NO: 19, or its salt, to the ligand;

(26) The compound or its salt according to (25), which is an antagonist;

(27) The compound or its salt according to (25), which is an agonist;

(28) A histamine release inhibitor comprising the compound or its salt according to (26);

(29) An agent for the prevention/treatment of immune disease, comprising the compound or its salt according to (26);

(30) An agent for the prevention/treatment of inflammatory disease, comprising the compound or its salt according to (26);

(31) A potentiator for nerve growth factor activity comprising the compound or its salt according to (27);

(32) An agent for the prevention/treatment of neurodegenerative disease, comprising the compound or its salt according to (27);

(33) An agent for the prevention/treatment of immune disease, comprising a compound or its salt that inhibits the activity of a protein containing the same or substantially the same amino acid sequence as the amino acid sequence represented by SEQ ID NO: 1 or SEQ ID NO: 19, its partial peptide, or a salt thereof;

(34) An agent for the prevention/treatment of neurodegenerative disease, comprising a compound or its salt that promotes the activity of a protein containing the same or substantially the same amino acid sequence as the amino acid sequence represented by SEQ ID NO: 1 or SEQ ID NO: 19, its partial peptide, or a salt thereof;

(35) An agent; for the prevention/treatment of immune disease or inflammatory disease, comprising an antibody to a protein containing the same or substantially the same amino acid sequence as the amino acid sequence represented by SEQ ID NO: 1 or SEQ ID NO: 19, its partial peptide, or a salt thereof;

(36) An agent for the prevention/treatment of immune disease or inflammatory disease, comprising a polynucleotide containing a base sequence complementary or substantially complementary to a polynucleotide encoding a protein containing the same or substantially the same amino acid sequence as the amino acid sequence represented by SEQ ID NO: 1 or SEQ ID NO: 19, its partial peptide, or a salt thereof, or a part of the base sequence;

(37) A ligand capable of binding specifically to a protein containing the same or substantially the same amino acid sequence as the amino acid sequence represented by SEQ ID NO: 1 or SEQ ID NO: 19, or a salt thereof;

(38) A protein containing the same or substantially the same amino acid sequence as the amino acid sequence represented by SEQ ID NO: 19, or a salt thereof;

(39) A protein consisting of the amino acid sequence represented by SEQ ID NO: 19, or a salt thereof;

(40) A partial peptide of the protein according to (38), or a salt thereof;

(41) A polynucleotide containing a polynucleotide encoding the protein according to (38), or its partial peptide;

(42) The polynucleotide according to (41), which is a DNA;

(43) A polynucleotide consisting of the base sequence represented by SEQ ID NO: 20;

(44) A recombinant vector containing the polynucleotide according to (41);

(45) A transformant transformed by the recombinant vector according to (44);

(46) A process of manufacturing the protein according to (38), its partial peptide, or a salt thereof, which comprises culturing the transformant according to (45) and producing/accumulating the protein according to (38), or its partial peptide;

(47) A pharmaceutical comprising the protein according to (38), its partial peptide, or a salt thereof;

(48) A pharmaceutical comprising the polynucleotide according to (41);

(49) A diagnostic product comprising the polynucleotide according to (41);

(50) An antibody to the protein according to (38), its partial peptide, or a salt thereof;

(51) A pharmaceutical comprising the antibody according to (50);

(52) A diagnostic product comprising the antibody according to (50);

(53) A polynucleotide containing a base sequence complementary or substantially complementary to the polynucleotide according to (41), or a part of the base sequence;

(54) The polynucleotide according to (53), which is a DNA;

(55) A pharmaceutical comprising the polynucleotide according to (53);

(56) A method of quantification of mRNA of the protein according to (38), which comprises using the polynucleotide according to (41), or a part of the polynucleotide;

(57) A method of quantification of the protein according to (38), which comprises using the antibody according to (50);

(58) A method of diagnosis for diseases associated with the functions of the protein according to (38), which comprises-using the method of quantification according to (57);

(59) A method of determining a ligand to the protein or its salt according to (38), which comprises using the protein according to (38), its partial peptide, or a salt thereof;

(60) A transgenic non-human mammal bearing the polynucleotide according to (42) or its variant DNA, which is exogenous;

(61) The mammal according to (60), wherein the non-human mammal is a rodent;

(62) The mammal according to (61), wherein the rodent is mouse or rat;

(63) A recombinant vector bearing the exogenous polynucleotide according to (42) or its variant DNA and capable of being expressed in the non-human mammal;

(64) A method of screening a compound or its salt having an effect on diseases caused by deficiency/damages of the polynucleotide according to (42), which comprises using the mammal according to (60); etc.

Hereinafter "the protein containing the same or substantially the same amino acid sequence as the amino acid sequence represented by SEQ ID NO: 1 or SEQ ID NO: 19, its partial peptide, or a salt thereof" is sometimes merely referred to as "the receptor of the present invention." Also, "the ligand capable of binding specifically to the receptor of the present invention" is sometimes simply referred to as "the ligand of the present invention."

The present invention further provides the following features:

(i) a method of screening a compound that changes the binding properties of the ligand of the present invention to the receptor of the present invention, which comprises assaying the GTPγS binding-promoting activities on the cell membrane fraction of the receptor of the present invention, in the presence of labeled GTPγS, when the ligand of the present invention is brought in contact with the cell membrane fraction of the receptor of the present invention and when the ligand of the present invention and a test compound are brought in contact with the cell membrane fraction of the receptor of the present invention, and comparing the activities;

(ii) a method of screening a compound that changes the binding properties of the ligand of the present invention to the receptor of the present invention, which comprises assaying the intracellular cAMP production inhibitory activities on the cell described below, in the presence of a substance for increasing the intracellular cAMP level, when the ligand of the present invention is brought in contact with a cell wherein the receptor of the present invention is expressed and when the ligand of the present invention and a test compound are brought in contact with the cell wherein the receptor of the present invention is expressed, and comparing the activities;

(iii) a method of screening a compound that changes the binding properties of the ligand of the present invention to the receptor of the present invention, which comprises assaying the enzyme activities of a reporter gene protein in the presence of a substance for increasing the intracellular cAMP level, when the ligand of the present invention is brought in contact with a cell wherein the receptor of the present invention with a CRE-reporter gene vector transfected is expressed and when the ligand of the present invention and a test compound are brought in contact with the cell wherein the receptor of the present invention with a CRE-reporter gene vector transfected is expressed, and comparing the activities;

(iv) a method of screening a compound that changes the binding properties of the ligand of the present invention to the receptor of the present invention, which comprises assaying the arachidonic acid metabolite-releasing activities, when the ligand of the present invention is brought in contact with a cell wherein the receptor of the present invention containing labeled arachidonic acid is expressed and when the ligand of the present invention and a test compound are brought in contact with the cell wherein the receptor of the present invention containing labeled arachidonic acid is expressed, and comparing the activities;

(v) a method of screening a compound that changes the binding properties of the ligand of the present invention to the receptor of the present invention, which comprises assaying the intracellular calcium level increasing activities, when the ligand of the present invention is brought in contact with a cell wherein the receptor of the present invention is expressed and when the ligand of the present invention and a test compound are brought in contact with the cell wherein the receptor of the present invention is expressed, and comparing the activities;

(vi) a method of screening a compound that changes the binding properties of the ligand of the present invention to the receptor of the present invention, which comprises assaying the inositol triphosphate producing activities in the presence of labeled inositol, when the ligand of the present invention is brought in contact with the cell wherein the receptor of the present invention is expressed and when the ligand of the present invention and a test compound are brought in contact with the cell wherein the receptor of the present invention is expressed, and comparing the activities;

(vii) a method of screening a compound that changes the binding properties of the ligand of the present invention to the receptor of the present invention, which comprises assaying the enzyme activities of a reporter gene protein, when the ligand of the present invention is brought in contact with a cell wherein the receptor of the present invention with a TRE-reporter gene vector transfected is expressed and when the ligand of the present invention and a test compound are brought in contact with the cell wherein the receptor of the present invention with a TRE-reporter gene vector transfected is expressed, and comparing the activities;

(viii) a method of screening a compound that changes the binding properties of the ligand of the present invention to the receptor of the present invention, which comprises assaying the cell growth, when the ligand of the present invention is brought in contact with a cell wherein the receptor of the present invention is expressed and when the ligand of the present invention and a test compound are brought in contact with the cell wherein the receptor of the present invention is expressed, and comparing the cell growth;

(ix) a method of screening a compound that changes the binding properties of the ligand of the present invention to the receptor of the present invention, which comprises assaying the efflux activities of labeled rubidium in the presence of labeled rubidium, when the ligand of the present invention is brought in contact with the cell wherein the receptor of the present invention is expressed and when the ligand of the present invention and a test compound are brought in contact with the cell wherein the receptor of the present invention is expressed, and comparing the cell activities;

(x) a method of screening a compound that changes the binding properties of the ligand of the present invention to the receptor of the present invention, which comprises assaying the extracellular pH changes, when the ligand of the present invention is brought in contact with the cell wherein the receptor of the present invention is expressed and when the ligand of the present invention and a test compound are brought in contact with the cell wherein the receptor of the present invention is expressed, and comparing the changes;

(xi) a method of screening a compound that changes the binding properties of the ligand of the present invention to the receptor of the present invention, which comprises culturing in a histidine-deficient medium yeast wherein the receptor of the present invention with a histidine synthetic gene transfected is expressed, contacting with the ligand of the present invention or with the ligand of the present invention and a test compound, and measuring and comparing the growth of the yeast;

(xii) a method of screening a compound that changes the binding properties of the ligand of the present invention to the receptor of the present invention, which comprises measuring the changes in cell membrane potential when the ligand of the present invention is brought in contact with the *Xenopus laevis* oocytes where RNA of a gene for the receptor of the present invention is transfected and when the ligand of the present invention and a test compound are brought in contact with the *Xenopus laevis* oocytes where RNA of a gene for the receptor of the present invention is transfected, and comparing the changes; etc.

BEST MODE FOR CARRYING OUT THE INVENTION

Figure 1:
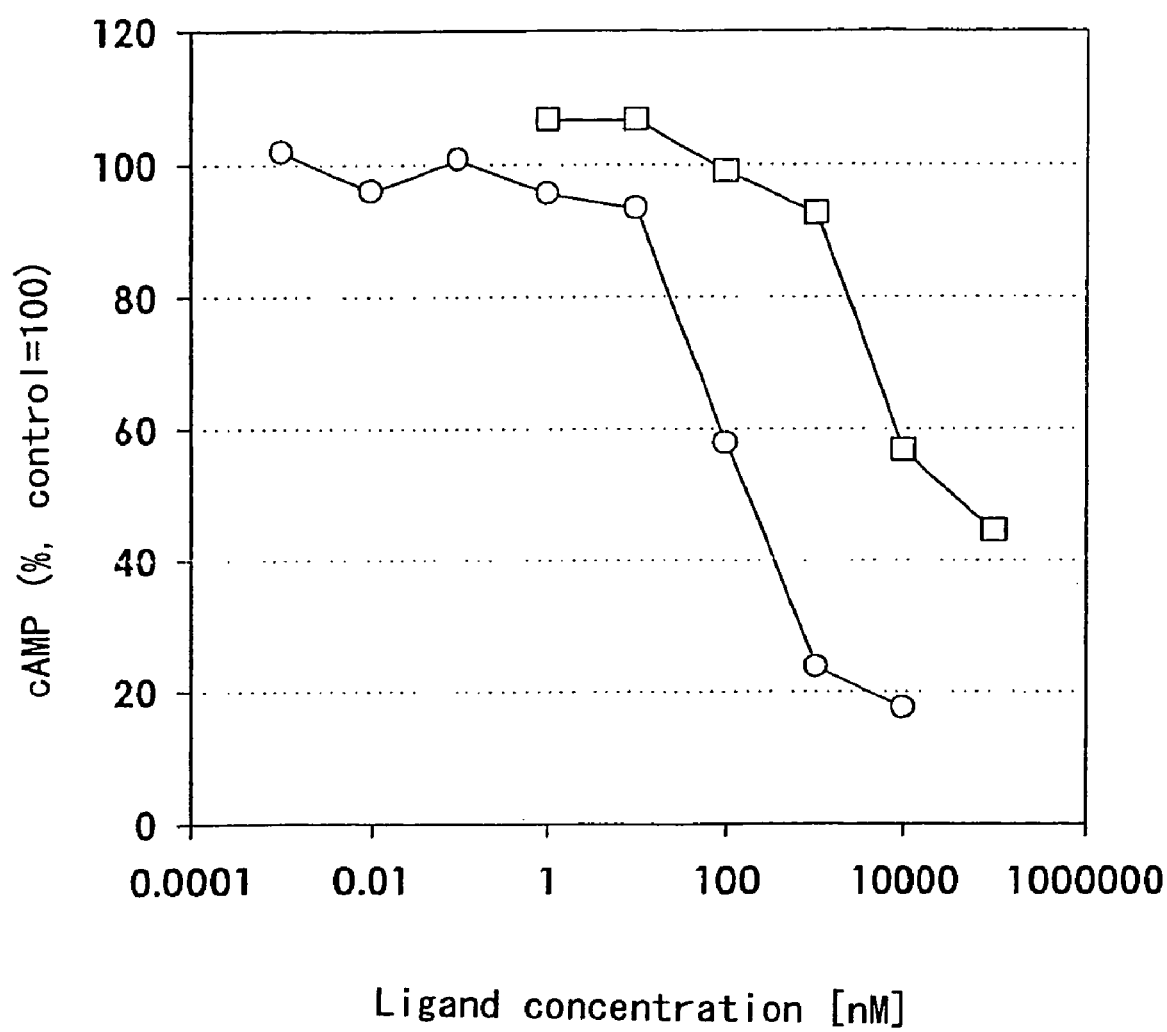
FIG. 1 shows the cAMP production inhibitory activities of lysophosphatidylserine and phosphatidylserine on GPR34-expressed CHO cells. In the figure, -o- designates the activity when lysophosphatidylserine was administered and -□- designates he activity when phosphatidylserine was administered.

The protein containing the same or substantially the same amino acid sequence as the amino acid sequence represented by SEQ ID NO: 1 or SEQ ID NO: 19 may be any protein derived from any cells of human and warm-blooded animals (e.g., guinea pig, rat, mouse, fowl, rabbit, swine, sheep, bovine, monkey, etc.) (for example, retina cell, liver cell, splenocyte, nerve cell, glial cell, pancreatic β cell, bone marrow cell, mesangial cell, Langerhans' cell, epidermic cell, epithelial cell, endothelial cell, fibroblast, fibrocyte, myocyte, fat cell, immune cell (e.g., macrophage, T cell, B cell, natural killer cell, mast cell, neutrophil, basophil, eosinophil, monocyte), megakaryocyte, synovial cell, chondrocyte, bone cell, osteoblast, osteoclast, mammary gland cell, hepatocyte, interstitial cell, etc., or the corresponding precursor cells, stem cells, cancer cells, etc.), or any tissues where such cells are present, such as brain or any of brain regions (e.g., retina, olfactory bulb, amygdaloid nucleus, basal ganglia, hippocampus, thalamus, hypothalamus, cerebral cortex, medulla oblongata, cerebellum), hypothalamus, hypophysis, stomach, pancreas, kidney, liver, gonad, thyroid, gall-bladder, bone marrow, adrenal gland, skin, muscle, lung, gastrointestinal tract (e.g., large intestine and small intestine), blood vessel, heart, thymus, spleen, submandibular gland, peripheral blood, prostate, testis, ovary, placenta, uterus, bone, joint, skeletal muscle, etc.; polypeptides derived from hemocyte type cells or their cultured cells (e.g., MEL, M1, CTLL-2, HT-2, WEHI-3, HL-60, JOSK-1, K562, ML-1, MOLT-3, MOLT-4, MOLT-10, CCRF-CEM, TALL-1, Jurkat, CCRT-HSB-2, KE-37, SKW-3, HUT-78, HUT-102, H9, U937, THP-1, HEL, JK-1, CMK, KO-812, MEG-01, etc.); these proteins may also be synthetic proteins.

The amino acid sequence which is substantially the same amino acid sequence as that represented by SEQ ID NO: 1 includes amino acid sequences having at least about 70% homology, preferably at least about 95% homology, more preferably at least about 80% homology and most preferably at least about 90% homology, to the amino acid sequence shown by SEQ ID NO: 1; etc.

Preferred examples of the protein containing substantially the same amino acid sequence as the amino acid sequence represented by SEQ ID NO: 1 include proteins having substantially the same amino acid sequence as the amino acid sequence represented by SEQ ID NO: 1 and having a property substantially equivalent to that of the protein having the amino acid sequence represented by SEQ ID NO: 1, etc. As the amino acid sequence which is substantially the same as the amino acid sequence represented by SEQ ID NO: 1, there are, for example, the amino acid sequence represented by SEQ ID NO: 22, and the like.

The amino acid sequence having substantially the same amino acid sequence as that represented by SEQ ID NO: 19 includes amino acid sequences having at least about 95% homology, preferably at least about 97% homology and most preferably at least about 99% homology, to the amino acid sequence represented by SEQ ID NO: 19; etc.

Preferred examples of the protein containing substantially the same amino acid sequence as the amino acid sequence represented by SEQ ID NO: 19 include proteins having substantially the same amino acid sequence as the amino acid sequence represented by SEQ ID NO: 19 and having a property substantially equivalent to that of the protein having the amino acid sequence represented by SEQ ID NO: 19, etc.

As the substantially equivalent properties, examples include the ligand binding activity, the signal transduction action, etc. The substantially equivalent is used to mean that the nature of these properties is equivalent in terms of quality (e.g., physiologically or pharmacologically). Thus, the activities such as the ligand binding activity, the signal transduction action, etc. are preferably equivalent (e.g., about 0.01 to 100 times, preferably about 0.1 to 10 times, more preferably 0.5 to 2 times), but differences in degree such as a level of these activities, quantitative factors such as a molecular weight of the protein may be present and allowable.

These activities such as the ligand binding activity, the signal transduction action, etc. can be determined by publicly known methods with modifications. For example, the activities can be assayed in accordance with the methods of determining ligands or screening methods described below.

Examples of the protein of the present invention used include (1) proteins containing (i) the amino acid sequence represented by SEQ ID NO: 1, of which at least 1 or 2 (e.g., about 1 to about 100, preferably about 1 to about 50, preferably about 1 to about 30, more preferably about 1 to about 10 and much more preferably several (1 to 5)) amino acids are deleted; (ii) the amino acid sequence represented by SEQ ID NO: 1, to which at least 1 or 2 (e.g., about 1 to about 100, preferably about 1 to about 50, preferably about 1 to about 30, more preferably about 1 to about 10 and much more preferably several (1 to 5)) amino acids are added; (iii) the amino acid sequence represented by SEQ ID NO: 1, in which at least 1 or 2 (e.g., about 1 to about 100, preferably about 1 to about 50, preferably about 1 to about 30, more preferably about 1 to about 10 and much more preferably several (1 to 5)) amino acids are substituted by other amino acids; (iv) the amino acid sequence represented by SEQ ID NO: 1, in which at least 1 or 2 (e.g., about 1 to about 100, preferably about 1 to about 50, preferably about 1 to about 30, more preferably about 1 to about 10 and much more preferably several (1 to 5)) amino acids are inserted; or (v) a combination of these amino acid sequences; etc.; and (2) proteins containing (i) the amino acid sequence represented by SEQ ID NO: 19, of which at least 1 or 2 (e.g., about 1 to about 15, preferably about 1 to about 10 and more preferably several (1 to 5)) amino acids are deleted; (ii) the amino acid sequence represented by SEQ ID NO: 19, to which at least 1 or 2 (e.g., about 1 to about 15, preferably about 1 to about 10 and more preferably several (1 to 5)) amino acids are added; (iii) the amino acid sequence represented by SEQ ID NO: 19, in which at least 1 or 2 (e.g., about 1 to about 15, preferably about 1 to about 10 and more preferably several (1 to 5)) amino acids are substituted by other amino acids; (iv) the amino acid sequence represented by SEQ ID NO: 1, in which at least 1 or 2 (e.g., about 1 to about 15, preferably about 1 to about 10 and more preferably several (1 to 5)) amino acids are inserted; or (v) a combination of these amino acid sequences; etc.

The partial peptide of the receptor of the present invention (hereinafter sometimes referred to as the partial peptide of the present invention) may be any partial peptide so long as it the partial peptide which can be used for the methods of screening pharmaceuticals later described. Among the protein molecules of the present invention, for example, those bearing the site exposed to outside of the cell membrane and retaining substantially the same ligand binding activity, etc. may be employed.

Specifically, the partial peptide of the receptor protein having the amino acid sequence represented by SEQ ID NO: 1 or SEQ ID NO: 19 is a peptide containing the part which has been analyzed to be an extracellular domain (hydrophilic region) in the hydrophobic plot analysis. A peptide containing a hydrophobic domain part can be used as well. In addition, there may be employed a peptide containing each domain separately and a peptide containing a plurality of domains together.

In the partial peptide of the present invention, the number of amino acids is at least 20, preferably at least 50 and more preferably at least 100, in the amino acid sequence which constitutes the protein of the present invention, and the peptide having the sequence of such amino acids, etc. are preferred.

Herein, the term "substantially equivalent activity" is intended to mean the same significance as defined above. The "substantially equivalent activity" can be assayed in the same way as described above.

Also, in the partial peptide of the present invention, (1) at least 1 or 2 (preferably about 1 to about 20, more preferably about 1 to about 10 and much more preferably several (1 to 5)) amino acids may be deleted in the amino acid sequences described above; (2) at least 1 or 2 (preferably about 1 to about 20, more preferably about 1 to about 10 and much more preferably several (1 to 5)) amino acids may be added to the amino acid sequences described above; or (3) at least 1 or 2 (preferably about 1 to about 20, more preferably about 1 to about 10 and much more preferably several (1 to 5)) amino acids may be substituted by other amino acids.

Specific examples of the partial peptide employed include a partial peptide containing the amino acid sequence of 1–53, 114–128, 197–216 or 293–310 in the sequence represented by SEQ ID NO: 1, a partial peptide containing the amino acid sequence of 1–46, 107–121, 190–209 or 286–303 in the sequence represented by SEQ ID NO: 19; etc.

The receptor of the present invention and the partial peptide of the present invention are represented in accordance with the conventional way of describing peptides, that is, the N-terminus (amino terminus) at the left hand and the C-terminus (carboxyl terminus) at the right hand. The C-terminus may be in the form of a carboxyl group (—COOH), a carboxylate (—COO—), an amide (—CONH$_2$) or an ester (—COOR).

Herein, examples of the ester group shown by R include a $C_{1-6}$ alkyl group such as methyl, ethyl, n-propyl, isopropyl, n-butyl, etc.; a $C_{3-8}$ cycloalkyl group such as cyclopentyl, cyclohexyl, etc.; a $C_{6-12}$ aryl group such as phenyl, α-naphthyl, etc.; a $C_{7-14}$ aralkyl such as a phenyl-$C_{1-2}$ alkyl group, e.g., benzyl, phenethyl, etc.; an α-naphthyl-$C_{1-2}$ alkyl group such as α-naphthylmethyl, etc.; in addition, pivaloyloxymethyl, etc., widely used as an ester for oral administration, may also be used.

Where the receptor of the present invention and the partial peptide of the present invention contain a carboxyl group (or a carboxylate) at a position other than the C-terminus, the carboxyl group may be amidated or esterified and such an amide or ester is also included within the receptor of the present invention and the partial peptide of the present invention. As the ester in this case, the C-terminal esters described above, etc. are used Furthermore, examples of the receptor of the present invention and the partial peptide of the present invention include variants wherein the amino group at the N-terminal amino acid residues (e.g., methionine residue) is protected with a protecting group (e.g., a $C_{1-6}$ acyl group such as a $C_{1-6}$ alkanoyl group, e.g., formyl group, acetyl group, etc.); those wherein the N-terminal glutamine residue is cleaved in vivo and the glutamyl group thus formed is pyroglutaminated;

those wherein a substituent (e.g., —OH, —SH, amino group, imidazole group, indole group, guanidino group, etc.) on the side chain of an amino acid in the molecule is protected with a suitable protecting group (e.g., a $C_{1-6}$ acyl group such as a $C_{1-6}$ alkanoyl group, e.g., formyl group, acetyl group, etc.), or conjugated proteins such as glycoproteins having sugar chains; etc.

As salts of the receptor of the present invention or the partial peptide of the present invention, salts with physiologically acceptable acids (e.g., inorganic acids or organic acids) or bases (e.g., alkali metal salts) may be employed, preferably in the form of physiologically acceptable acid addition salts. Examples of such salts include salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid) and the like.

The ligand (ligand of the present invention) capable of binding specifically to the protein containing the same or substantially the same amino acid sequence as the amino acid sequence represented by SEQ ID NO: 1 or SEQ ID NO: 19 may be any substance so long as it binds specifically to the receptor of the present invention. Examples of the ligand include those having a dissociation constant of 10 μM or less, preferably not greater than 2 μM, more preferably not greater than 1 μM, particularly preferably not greater than 200 nM, and most preferably not greater than 100 nM, in binding to the protein or its salt containing the same or substantially the same amino acid sequence as the amino acid sequence represented by SEQ ID NO: 1 or SEQ ID NO: 19, and the like.

As the ligand of the present invention, for example, lipids or the like are employed. Specifically, phospholipids such as phosphonolipids, etc. are used as well. Preferably, there are used ether phospholipids, phosphono-ether lipids, glycerophospholipids, phosphono-glycerolipids, sphingolipids, sphingophospholipids, phosphonosphingolipids, etc. Among them, preferred are ether phospholipids, phosphono-ether lipids, glycerophospholipids and phosphono-glycerolipids. More preferred are glycerophospholipids.

The ligand of the present invention further includes a mixture of two or more lipids selected from ether phospholipids, phosphono-ether lipids, glycerophospholipids, phosphono-glycerolipids, sphingolipids, sphingophospholipids and phosphonosphingolipids.

Examples of the ether phospholipids, phosphono-ether lipids, glycerophospholipids and phosphono-glycerolipids include Compound (I), etc.

Preferably, Compound (I) is a compound represented by the following formula:

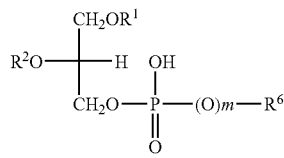

[wherein the symbols have the same significance as described above] or salts thereof.

More preferably, Compound (I) is a compound represented by the following formula:

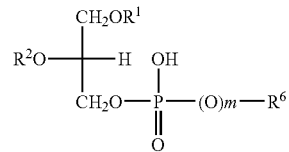

[wherein the symbols have the same significance as described above] or salts thereof.

In each formula, the "hydrocarbon group" in "hydrocarbon group which may optionally have a substituent(s)" shown by $R^1$, $R^2$ or $R^3$ is preferably an alkyl, an alkenyl, an alkynyl, a cycloalkyl, etc. The carbon atom number is preferably 1 to 30.

Examples of the "alkyl" include a $C_{1-30}$ alkyl (e.g., methyl, ethyl, propyl, isopropyl, butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, henicosy, docosyl, tricosyl, tetracosyl, pentacosyl, hexacosyl, heptacosyl, octacosyl, nonacosyl, triacontyl, etc.), and the like. More preferably, the alkyl is a $C_{13-19}$ alkyl such as tridecyl, tetradecyl, pentadecyl, hexadecyl, heptadecyl, octadecyl, nonadecyl, etc.

Examples of the "alkenyl" include a $C_{2-30}$ alkenyl (e.g., vinyl, allyl, isopropenyl, 1-butenyl, 2-butenyl, 3-butenyl, 2-methyl-2-propenyl, 1-methyl-2-propenyl, 2-methyl-1-propenyl, hexenyl, heptenyl, octenyl, nonenyl, decenyl, undecenyl, dodecenyl, tridecenyl, tetradecenyl, tetradecadienyl, pentadecenyl, pentadecadienyl, hexadecenyl, hexadecadienyl, heptadecenyl, heptadecatrienyl, octadecenyl, octadecadienyl, nonadecenyl, nonadecadienyl, nonadecatrienyl, nonadecatatraenyl, icosenyl, icosadienyl, henicosenyl, docosenyl, tricosenyl, tetracosenyl, pentacosenyl, hexacosenyl, heptacosenyl, octacosenyl, nonacosenyl, tricontenyl, etc.) and the like. Preferably, the alkenyl is a $C_{13-19}$ alkenyl.

Examples of the "alkynyl" include a $C_{2-30}$ alkynyl (e.g., ethynyl, propargyl, 1-butynyl, 2-butynyl, 3-butynyl, 1-hexynyl, tetradecynyl, pentadecynyl, hexadecynyl, heptadecynyl, octadecynyl, nonadecynyl, icosynyl, henicosynyl, docosynyl, tricosynyl, tetracosynyl, pentacosynyl, hexacosynyl, heptacosynyl, octacosynyl, nonacosynyl, triacontynyl, etc.) and the like. Preferably, the alkynyl is a $C_{15-17}$ alkynyl.

Examples of the "cycloalkyl" include a $C_{3-6}$ cycloalkyl (e.g., cyclopropyl, cyclobutyl, cyclopentyl, cyclohexyl, etc.) and the like.

The "acyl" shown by $R^1$, $R^2$ or $R^3$ includes groups represented by formula: —CO—$R^8$, —(C=O)—O$R^8$, —(C=O)—N$R^8R^9$, —SO—$R^{10}$ or —$SO_2$—$R^{10}$ [wherein $R^8$ represents hydrogen atom, a hydrocarbon group which may optionally have a substituent(s) or a heterocyclic group which may optionally have a substituent(s); $R^9$ reparesents hydrogen atom or a $C_{1-6}$ alkyl; $R^{10}$ represents a hydrocarbon group which may optionally have a substituent(s) or a heterocyclic group which may optionally have a substituent(s)], etc. Preferably the acyl is a group shown by formula: —CO—$R^8$.

The "hydrocarbon group" in "the hydrocarbon group which may optionally have a substituent(s)," which is represented by $R^8$ or $R^{10}$, includes the above-described "hydrocarbon group" shown by $R^1$, $R^2$ or $R^3$.

In the specification, examples of the "substituent(s)" in the "hydrocarbon group which may optionally have a substituent(s)" include a halogen atom (e.g., fluorine, chlorine, bromine, iodine, etc.), a $C_{1-3}$ alkylenedioxy (e.g., methylenedioxy, ethylenedioxy, etc.), nitro, cyano, a $C_{1-6}$ alkyl which may optionally be halogenated (e.g., methyl, chloromethyl, difluoromethyl, trichloromethyl, trifluoromethyl, ethyl, 2-bromoethyl,2,2,2-trifluoroethyl, pentafluoroethyl, propyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl, 6,6,6-trifluorohexyl, etc.), a $C_{2-6}$ alkenyl, $C_{2-6}$ alkenyl, a $C_{3-6}$ cycloalkyl which may optionally be halogenated (e.g., cyclopropyl, cyclobutyl, cyclopentyl, cyclohexyl, 4,4-dichlorocyclohexyl, 2,2,3,3-tetrafluorocyclopentyl, 4-chlorocyclohexyl, etc.), a $C_{6-14}$ aryl (e.g., phenyl, 1-naphthyl, 2-naphthyl, 2-biphenylyl, 3-biphenylyl, 4-biphenylyl, 2-anthryl, etc.), a $C_{1-8}$ alkoxy which may optionally be halogenated (e.g., methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy, hexyloxy, etc.), hydroxy, a $C_{6-14}$ aryloxy (e.g., phenyloxy, 1-naphthyloxy, 2-naphthyloxy, etc.), a $C_{7-16}$ aralkyloxy (e.g., benzyloxy, phenethyloxy, etc.), mercapto, a $C_{1-6}$ alkylthio which may optionally be halogenated (e.g., methylthio, difluoromethylthio, trifluoromethylthio, ethylthio, propylthio, isopropylthio, butylthio, 4,4,4-trifluorobutylthio, pentylthio, hexylthio, etc.), a $C_{6-14}$ arylthio (e.g., phenylthio, 1-naphthylthio, 2-naphthylthio, etc.), a $C_{7-16}$ aralkylthio (e.g., benzylthio, phenethylthio, etc.), amino, a mono-$C_{1-6}$-alkylamino (e.g., methylamino, ethylamino, etc.), a mono-$C_{6-14}$-arylamino (e.g., phenylamino, 1-naphthylamino, 2-naphthylamino, etc.), a di-$C_{1-6}$-alkylamino (e.g., dimethylamino, diethylamino, ethylmethylamino, etc.), a di-$C_{6-14}$-arylamino (e.g., diphenylamino, etc.), formyl, carboxy, a $C_{1-6}$-alkyl-carbonyl (e.g., acetyl, propionyl, etc.), a $C_{3-6}$ cycloalkyl-carbonyl (e.g., cyclopropylcarbonyl, cyclopentylcarbonyl, cyclohexylcarbonyl, etc.), a $C_{1-6}$-alkoxy-carbonyl (e.g., methoxycarbonyl, ethoxycarbonyl, propoxycarbonyl, tert-butoxycarbonyl, etc.), a $C_{6-14}$ aryl-carbonyl (e.g., benzoyl, 1-naphthoyl, 2-naphthoyl, etc.), a $C_{7-16}$ aralkyl-carbonyl (e.g., phenylacetyl, 3-phenylpropionyl, etc.), a $C_{6-14}$ aryloxy-carbonyl (e.g., phenoxycarbonyl, etc.), a $C_{7-16}$ aralkyloxy-carbonyl (e.g., benzyloxycarbonyl, phenethyloxycarbonyl, etc.), a 5- or 6-membered heterocyclic carbonyl (e.g., nicotinoyl, isonicotinoyl, thenoyl, furoyl, morpholinocarbonyl, thiomorpholinocarbonyl, piperazine-1-ylcarbonyl, pyrrolidin-1-ylcarbonyl, etc.), carbamoyl, a mono-$C_{1-6}$ alkylcarbamoyl (e.g., methylcarbamoyl, ethylcarbamoyl, etc.), a di-$C_{1-6}$ alkyl-carbamoyl (e.g., dimethylcarbamoyl, diethylcarbamoyl, ethylmethylcarbamoyl, etc.), a $C_{6-14}$ aryl-carbamoyl (e.g., phenylcarbamoyl, 1-naphthylcarbamoyl, 2-naphthylcarbamoyl, etc.), a 5-membered or 6-membered heterocyclic carbamoyl (e.g., 2-pyridylcarbamoyl, 3-pyridylcarbamoyl, 4-pyridylcarbamoyl, 2-thienylcarbamoyl, 3-thienylcarbamoyl, etc.). a $C_{1-6}$ alkylsulfonyl (e.g., methylsulfonyl, ethylsulfonyl, etc.), a $C_{6-14}$ arylsulfonyl (e.g., phenylsulfonyl, 1-naphthylsulfonyl, 2-naphthylsulfonyl, etc.), formylamino, a $C_{1-6}$ alkyl-carbonylamino (e.g., acetylamino, etc.), a $C_{6-14}$ aryl-carbonylamino (e.g., benzoylamino, naphthoylamino, etc.), a $C_{1-6}$ alkoxy-carbonylamino (e.g., methoxycarbonyl amino, ethoxycarbonylamino, propoxycarbonylamino, butoxycarbonylamino, etc.), a $C_{1-6}$ alkylsulfonylamino (e.g., methylsulfonylamino, ethylsulfonylamino, etc.), a $C_{6-14}$ arylsulfonylamino (e.g., phenylsulfonylamino, 2-naphthylsulfonylamino, 1-naphthylsulfonylamino, etc.), a $C_{1-6}$ alkyl-carbonyloxy (e.g., acetoxy, propionyloxy, etc.), a $C_{6-14}$ aryl-carbonyloxy (e.g., benzoyloxy, naphthylcarbonyloxy, etc.), a $C_{1-6}$ alkoxycarbonyloxy (e.g., methoxycarbonyloxy, ethoxycarbonyloxy, propoxycarbonyloxy, butoxycarbonyloxy, etc.), a mono-$C_{1-6}$ alkylcarbamoyloxy (e.g., methylcarbamoyloxy, ethylcarbamoyloxy, etc.), a di-$C_{1-6}$ alkylcarbamoyloxy (e.g., dimethylcarbamoyloxy, diethylcarbamoyloxy, etc.), a $C_{6-14}$ aryl-carbamoyloxy (e.g., phenylcarbamoyloxy, naphthylcarbamoyloxy, etc.), nicotinoyloxy, a 5- to 7-membered saturated cyclic amino (e.g., pyrrolidin-1-yl, piperidino, piperazin-1-yl, morpholino, thiomorpholino, tetrahydroazepin-1-yl, etc.), a 5- to 10-membered aromatic heterocyclic group (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl, etc.), sulfo, etc.

The "hydrocarbon group" may have, e.g., 1 to 5, preferably 1 to 3, of the substituents described above at substitutable positions. Where the number of substituent(s) is 2 or more, the respective substituents may be the same or different.

The "heterocylic group" in the "heterocyclic group which may optionally have a substituent(s)," which is represented by $R^8$ or $R^{10}$, includes monovalent groups formed by removing one optional hydrogen atom from a 5- to 14-membered (monocyclic, dicyclic or tricyclic) hetero-ring containing, e.g., 1 or 2 members and 1 to 4 hetero atoms selected from nitrogen atom, sulfur atom and oxygen atom, in addition to carbon atoms, preferably (i) a 5- to 14-membered (preferably 5- to 10-membered) aromatic hetero-ring, (ii) a 5- to 10-membered non-aromatic hetero-ring or (iii) a 7- to 10-membered bridged hetero-ring; etc.

Examples of the "5- to 14-membered (preferably 5- to 10-membered) aromatic hetero-ring" include aromatic hetero-ring such as thiophen, benzo[b]thiophen, benzo[b]furan, benzimidazole, benzoxazole, benzothiazole, benzisothiazole, naphtho[2,3-b]thiophen, furan, pyrrole, imidazole, pyrazole, pyridine, pyrazine, pyrimidine, pyridazine, indole, isoindole, 1H-indazole, purine, 4H-quinolidine, isoquinoline, quinoline, phthalazine, naphthylidine, quinoxaline, quinazoline, cinnoline, carbazole, β-carboline, phenanthridine, acridine, phenazine, thiazole, isothiazole, phenothiazine, isoxazole, furazan, phenoxazine, etc.; or a ring formed by fusing these rings (preferably a mono-ring) with one or more (preferably 1 or 2) aromatic rings (e.g., a benzene ring, etc.); and the like.

Examples of the "5- to 10-membered non-aromatic hetero-ring" described above include pyrrolidine, imidazoline, pyrazolidine, pyrazoline, piperidine, piperazine, morpholine, thiomorpholine, dioxazole, ozadiazoline, thiadiazoline, triazoline, thiadiazole, dithiazole, etc.

Examples of the "7- to 10-membered bridged hetero-ring" include quinuclidine, 7-azabicyclo[2.2.1]heptane, etc.

The "heterocylic group" is preferably a 5- to 14-membered (preferably 5- to 10-membered) (and monocyclic or bicyclic) heterocyclic group containing, in addition to carbon atoms, 1 or 2 members selected from nitrogen atom, sulfur atom and oxygen atom, preferably 1 to 4 heter atoms. Specific examples include aromatic heterocyclic groups such as 2-thienyl, 3-thienyl, 2-furyl, 3-furyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, pyrazinyl, 2-pyrimidinyl, 4-pyrimidinyl, 3-pyrrolyl, 2-imidazolyl, 3-pyridazinyl, 3-isothiazolyl, 3-isoxazolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl, etc.; non-aromatic heterocylic groups such as 1-pyrrolidinyl, 2-pyrrolidinyl, 3-pyrrolidinyl, 2-imidazolinyl, 4-imidazolinyl, 2-pyrazolidinyl, 3-pyrazolidinyl, 4-pyrazolidinyl, piperidino, 2-piperidyl, 3-piperidyl, 4-piperidyl, 1-piperazinyl, 2-piperazinyl, morpholino, thiomorpholino, etc.

Among them, preferred are 5- or 6-membered heterocyclic groups containing, in addition to carbon atoms, e.g., 1 to 3 hetero atoms selected from nitrogen atom, sulfur atom and oxygen atom; etc. Specific examples are 2-thienyl, 3-thienyl, 2-pyridyl, 3-pyridyl, 4-pyridyl, 2-furyl, 3-furyl, pyrazinyl, 2-pyrimidinyl, 3-pyrrolyl, 3-pyridazinyl, 3-isothiazolyl, 3-isoxazolyl, 1-pyrrolidinyl, 2-pyrrolidinyl, 3-pyrrolidinyl, 2-imidazolinyl, 4-imidazolinyl, 2-pyrazolidinyl, 3-pyrazolidinyl, 4-pyrazolidinyl, piperidino, 2-piperidyl, 3-piperidyl, 4-piperidyl, 1-piperazinyl, 2-piperazinyl, morpholino, thiomorpholino, etc.

Examples of the "substituent(s)" in the "heterocylic group which may optionally have a substituent(s)" are the same substituents, etc., as given for the "substituent(s)" in the "hydrocarbon group which may optionally have a substituent(s)," which is represented by $R^8$ or $R^{10}$ described above.

The "heterocyclic group" may have, e.g., 1 to 5, preferably 1 to 3, of the substituents described above at substitutable positions. Where the number of substituent(s) is 2 or more, the respective substituents may be the same or different.

Examples of the "$C_{1-6}$ alkyl" represented by $R^9$ include a $C_{1-6}$ alkyl such as methyl, ethyl, propyl, isopropyl, butyl, isobutyl, sec-butyl, tert-butyl, pentyl, hexyl, etc.

Examples of the "alkyl" in the "alkyl which may have a substituent(s)," which is represented by $R^6$, include a $C_{1-30}$ alkyl (e.g., methyl, ethyl, propyl, isopropyl, butyl, isobutyl, sec-butyl, tert-butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, henicosy, docosyl, tricosyl, tetracosyl, pentacosyl, hexacosyl, heptacosyl, octacosyl, nonacosyl, triacontyl, etc.), and the like. Preferably, the alkyl is a $C_{1-6}$ alkyl, etc.

Examples of the "substituent(s)" in the "alkyl which may optionally have a substituent(s)" represented by $R^6$ include hydroxy, carboxy, amino, an alkylammonio (e.g., trimethylammonio, etc.), etc., in 1 to 30 substituents.

Examples of the "cycloalkyl" in the "cycloalkyl which may optionally have a substituent(s)" represented by $R^6$ include a $C_{3-6}$ cycloalkyl (e.g., cyclopropyl, cyclobutyl, cyclopentyl, cyclohexyl, etc.), and the like.

Examples of the "substituent(s)" in the "cycloalkyl which may optionally have a substituent(s)" represented by $R^6$ include a hydroxy which may have phosphono, carboxy, amino, an alkylammonio (e.g., trimethylammonio, etc.) and the like, in 1 to 30 substituents.

Preferred examples of $R^6$ are the cases in which the compounds represented by $R^6$—OH form, for example, an alcohol (e.g., a $C_{1-6}$ alcohol such as ethanol, etc.), a polyvalent alcohol (e.g., a trivalent alcohol such as glycerol, etc.), a polyvalent alcohol phosphoric acid adduct (e.g., glycerol-3-phosphate, etc.), an aminoalcohol (e.g., a $C_{1-6}$ alcoholamine such as ethanolamine, etc.), an alkylammonioalcohol (e.g., choline, etc.), an amino acid having hydroxy (e.g., serine, threonine, homoserine, 3-hydroxypurine, 4-hydroxypurine, hydroxylysine, tyrosine, etc.; preferably serine), a sugar alcohol (e.g., inositol, etc.), a sugar alcohol phosphoric acid adducat (e.g., inositol monophosphate, inositol diphosphate, inositol triphosphate, etc.), a monosaccharide (e.g.,: glucose, etc.), a monosaccharide phosphoric acid adduct (e.g., glucose 6-phosphate, glucose 1-phosphate, etc.), etc.

Among them, preferred examples are amino acids having hydroxy. In particular, L-form is preferred, most preferably, L-serine, etc.

Each of $R^1$ and $R^2$ is preferably hydrogen atom, an alkyl (e.g., a $C_{14-18}$ alkyl, etc.), an alkenyl (e.g., a $C_{2-3}$ alkenyl, etc.), an acyl (e.g., a $C_{1-30}$ alkyl-carbonyl, a $C_{2-30}$ alkenyl-carbonyl, etc.) and the like. More preferred are an acyl of a $C_{1-30}$ alkyl-carbonyl, a $C_{2-30}$ alkenyl-carbonyl, etc.

$R^3$ is preferably Group (III).

$R^6$ is preferably (a) hydrogen atom or (b) an alkyl or cycloalkyl, which may optionally have a substituent(s) selected from hydroxy, carboxy, amino and an alkylammonio, respectively. Specific examples are a $C_{1-6}$ alkyl, dihydroxypropyl, aminoethyl, trimethylammonioethyl, 2-amino2-carboxyethyl, hexahydroxycyclohexyl, etc.

For m, 1 is preferred.

In Compound (I), the following compounds are preferably used.

Ether phospholipids such as:

(1a) platelet activating factor [Compound (I) wherein $R^1$ is a $C_{16}$ alkyl (hexadecyl) and/or $C_{18}$ alkyl (octadecyl), $R^2$ is acetyl, $R^3$ is Group (III), $R^6$ is trimethylammonioethyl and m is 1], (1b) lyso-platelet activating factor [Compound (I) wherein $R^1$ is hexadecyl and/or octadecyl, $R^2$ is hydrogen atom, $R^3$ is Group (I), $R^6$ is trimethylammonioethyl and m is 1], (1c) plasmalogens [Compound (I) wherein $R^1$ is a 1-alkenyl, $R^2$ is a $C_{1-29}$ alkyl-carbonyl or a $C_{2-29}$ alkenyl-carbonyl (having 1 to 5 double bonds), $R^3$ is Group (III), $R^6$ is trimethylammonioethyl, aminoethyl or 2-amino2-carboxyethyl and m is 1], (1d) lyso-plasmalogens [Compound (I) wherein $R^1$ is a 1-alkenyl, $R^2$ is hydrogen atom, $R^3$ is Group (III), $R^6$ is trimethylammonioethyl, aminoethyl or 2-amino2-carboxyethyl and m is 1], etc.;

Glycerophospholipids such as:

(2a) phosphatidic acids [Compound (I) wherein $R^1$ is a $C_{10-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^2$ is a $C_{10-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^3$ is Group (III), $R^6$ is hydrogen atom, and m is 1], (2b) lysophosphatidic acids [Compound (I) wherein $R^1$ is hydrogen atom or a $C_{10-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^2$ is hydrogen atom, or a $C_{13-23}$ alkyl-carbonyl or a $C_{13-23}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl 5,8,11,14-icosatetraenoyl, docosanoyl, tetracosanoyl, 15-tetracosanoyl, hexacosanoyl, octacosanoyl, etc.), $R^3$ is Group (III), $R^6$ is hydrogen atom, and m is 1 (provided that, when $R^1$ is hydrogen atom, $R^2$ is other than hydrogen atom)], (2c) phosphatidylcholines [Compound (I) wherein $R^1$ is a $C_{10-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^2$ is a $C_{13-23}$ alkyl-carbonyl or a $C_{13-23}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^3$ is Group (III), $R^6$ is trimethylammonioethyl, and m is 1], (2d) lysophosphatidylcholines [Compound (I) wherein $R^1$ is hydrogen atom, or a $C_{10-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^2$ is hydrogen atom, or a $C_{10-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^3$ is Group (III), $R^6$ is trimethylammonioethyl, and m is 1 (provided that, when $R^1$ is hydrogen atom, $R^2$ is other than hydrogen atom)Compound (I)], (2e) phosphatidylethanolamines [Compound (I) wherein $R^1$ is a $C_{10-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8, 11-icosatrienoyl, 5,8,11,14-icosatetraenoyl, docosanoyl, tetracosanoyl, 15-tetracosanoyl, hexacosanoyl, octacosanoyl, etc.), $R^2$ is a $C_{10-28}$ alkyl-carbonyl or a $C_{10-28}$ alkenyl-carbonyl. (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^3$ は Group (III), $R^6$ は aminoethyl, and m is 1], (2f) lyso-phosphatidylehtanolamines [Compound (I) wherein $R^1$ is hydrogen atom, or a $C_{10-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^2$ is hydrogen atom, or a $C_{10-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^3$ is Group (III), $R^6$ is aminoethyl, and m is 1(provided that, when $R^1$ is hydrogen atom, $R^2$ is other than hydrogen atom)], (2g) phosphatidylserines [Compound (I) wherein $R^1$ is a $C_{10-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl,-hexacosanoyl, octacosanoyl, etc.), $R^2$ is a $C_{1-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^3$ is Group (III), $R^6$ is 2-amino2-carboxyethyl, and m is 1], (2h) lysophosphatidylserines [Compound (I) wherein $R^1$ is hydrogen atom, or a $C_{10-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^2$ is hydrogen atom, or a $C_{10-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12, 15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^3$ is Group (III), $R^6$ is 2-amino2-carboxyethyl, and m is 1(provided that, when $R^1$ is hydrogen atom, $R^2$ is other than hydrogen atom)], (2i) phosphatidylinositols [Compound (I) wherein $R^1$ is a $C_{10-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^2$ is a $C_{10-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^3$ is Group (III), $R^6$ is hexahydroxycyclohexyl, and m is 1], (2j) lysophosphatidylionositols [Compound (I) wherein $R^1$ is hydrogen atom,or a $C_{10-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^2$ is hydrogen atom, or a $C_{10-28}$ alkyl-carbonyl or a $C_{10-28}$ alkenyl-carbonyl (having 1 to 5 double bonds) (e.g., decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl, octacosanoyl, etc.), $R^3$ is Group (III), $R^6$ is hexahydroxycyclohexyl, and m is 1(provided that, when $R^1$ is hydrogen atom, $R^2$ is other than hydrogen atom)] and the like.

Among others, preferred compounds are:

(i) phosphatidylserines [Compound (I) wherein $R^1$ is decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl or octacosanoyl; $R^2$ is decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl or octacosanoyl; $R^3$ is Group (UT); $R^6$ is 2-amino2-carboxyethyl, and m is 1], (ii) lysophosphatidylserines [Compound (I) wherein $R^1$ is decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8,11-icosatrienoyl, 5,8,11,14-icosatetraenoyl, docosanoyl, tetracosanoyl, 15-tetracosanoyl, hexacosanoyl or octacosanoyl; $R^2$ is decanoyl, dodecanoyl, tetradecanoyl, hexadecanoyl, 9-hexadecenoyl, octadecanoyl, 9-octadecenoyl, 11-octadecenoyl, 9,12-octadecadienoyl, 9,12,15-octadecatrienoyl, 6,9,12-octadecatrienoyl, 9,11,13-octadecatrienoyl, icosanoyl, 8,11-icosadienoyl, 5,8, 11-icosatrienoyl, 5,8,11,14-icosatetraenoyl, docosanoyl, tetracosanoyl, 15-tetracosanoyl, hexacosanoyl or octacosanoyl; $R^2$ is Group (III), $R^6$ is 2-amino2-carboxyethyl, and m is 1], and the like.

Preferred are the compounds represented by the formula below:

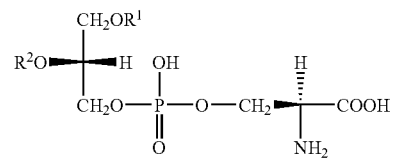

[wherein each symbol has the same significance as described above]. Herein, $R^1$ and $R^2$ are preferably hydrogen atom, an alkyl (e.g., a $C_{14-18}$ alkyl, etc.), an alkenyl (e.g., a $C_{2-3}$ alkenyl, etc.), or an acyl (e.g., a $C_{1-30}$ alkyl-carbonyl, a $C_{2-30}$ alkenyl-carbonyl, etc.) and the like.

Preferred $R^1$ is a $C_{1-30}$ alkyl-carbonyl, or the like. Preferred $R^2$ is hydrogen atom.

Specifically, there are 1-stearoyl-sn-glycero-3-phospho-L-serine, 1-palmitoyl-sn-glycero-3-phospho-L-serine, 1-oleoyl-sn-glycero-3-phospho-L-serine, etc.

As the sphingolipids, sphingophospholipids and phosphono-sphingolipids, there are, for example, Compound (II) and the like.

Compound (II) is preferably the compound represented by the formula below:

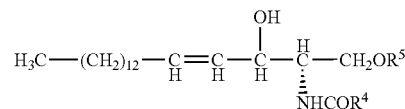

[wherein each symbol has the same significance as described above] or salts thereof.

In the formula described above, the "hydrocarbon group which may optionally have a substituent(s)" represented by $R^4$ is the same as those given for the aforesaid "hydrocarbon group which may optionally have a substituent(s)" represented by $R^1$, $R^2$ or $R^3$.

The "acyl" shown by $R^4$ is the same as the aforesaid "acyl" represented by $R^1$, $R^2$ or $R^3$.

The "hydrocarbon group which may optionally have a substituent(s)" represented by $R^5$ is the same as those given for the aforesaid "hydrocarbon group which may optionally have a substituent(s)" represented by $R^1$, $R^2$ or $R^3$.

The "acyl" shown by $R^5$ is the same as the aforesaid "acyl" represented by $R^1$, $R^2$ or $R^3$.

The "alkyl which may optionally have a substituent(s)" and the "cycloalkyl which may optionally have a substituent(s)" represented by $R^7$ are those given for the aforesaid "alkyl which may optionally have a substituent(s)" and the "cycloalkyl which may optionally have a substituent(s)" represented by $R^6$.

R[4] is preferably hydrogen atom, an acyl (e.g., $C_{1-30}$ alkyl-carbonyl, a $C_{2-30}$ alkenyl-carbonyl, etc.), and the like.

R[5] is preferably hydrogen atom or Group (IV), etc.

R[7] is preferably an alkyl which may optionally have amino.

Preferably, n is 1.

In Compound (II), the following compounds or the like are preferably used.

Sphingolipids such as:

(3a) sphingosines [Compound (II) wherein R[4] is hydrogen atom and R[5] is hydrogen], (3b) ceramides [Compound (II) wherein R[4] is a $C_{2-24}$ alkyl-carbonyl or a $C_{2-24}$ alkenyl-carbonyl (having 1 to 5 double bonds), R[5] is hydrogen atom], etc.; Sphingophospholipids such as:

(4a) sphingomyelins [Compound (IV) wherein R[4] is a $C_{2-24}$ alkyl-carbonyl or a $C_{2-24}$ alkenyl-carbonyl (having 1 to 5 double bonds), R[5] is Group (IV), R[7] is trimethylammonioethyl, and n is 1], (4b) sphingosyl 1-phosphate [Compound (II) wherein R[4] is hydrogen atom, R[5] is Group (IV), R[7] is hydrogen atom, and n is 1], (4c) sphingosylphosphorylcholine [Compound (II) wherein R[4] is hydrogen atom, R[5] is Group (IV), R[7] is trimethylammonioethyl and n is 1], and the like.

The compounds represented by formula (I), the compounds represented by formula (II) and salts thereof, which are labeled, are also included within the ligand of the present invention.

The labeling agent includes radioisotopes (e.g., [$^{3}$H], [$^{125}$I], [$^{14}$C], [$^{32}$P], [$^{33}$P], [$^{35}$S], etc.), fluorescent substances (e.g., fluorescein, etc.), luminescent substances (e.g., luminol, etc.), enzymes (e.g., a peroxidase, etc.), a lanthanide, etc. Among others, radioisotopes are preferred, with particular preference of tritium.

The labeled ligand is preferably the compound represented by formula (I) or salts thereof, which are labeled with radioisotopes, more preferably glycerophospholipids labeled with a radioisotope, further preferably lysophosphatidylserine or phosphatidylserine labeled with a radioisotope (preferably tritium), and much more preferably lysophosphatidylserine labeled with tritium, etc.

Specific examples of the tritium-labeled lysophosphatidylserine include 1-[9,10-$^{3}$H$_{2}$]-stearoyl-sn-glycero-3-phospho-L-serine represented by the formula below.

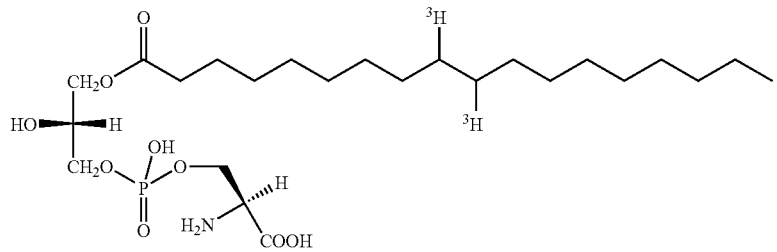

Preferably, the labeled ligand is 1-[9(S), 10(R)—$^{3}$H$_{2}$]-stearoyl-sn-glycero-3-phospho-L-serine represented by the formula below:

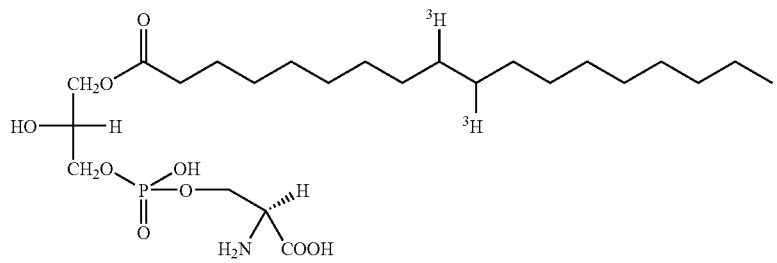

or 1-[9(R),10(S)—$^{3}$H$_{2}$]-stearoyl-sn-glycero-3-phospho-L-serine represented by the formula below, etc.

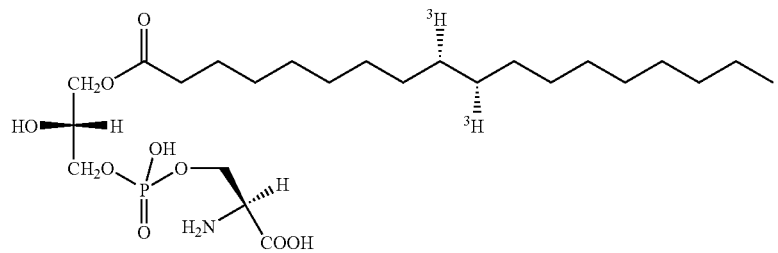

As salts of the compounds represented by formula (I) and salts of the compounds represented by formula (II), there are, for example, metal salts, ammonium salts, salts with organic bases, salts with inorganic acids, salts with organic acids, salts with basic or acidic amino acids, etc. Preferred examples of the metal salts include alkali metal salts such as sodium salts, potassium salts, etc.; alkaline earth meal salts such as calcium salts, magnesium salts, barium salts, etc.; aluminum salts, etc. Preferred examples of the salts with organic bases include salts with trimethylamine, triethylamine, pyridine, picoline, 2,6-lutidine, ethanolamine, diethanolamine, triethanolamine, cyclohexylamine, dicyclohexylamine, N,N-dibenzylethylenediamine, etc. Preferred examples of the salts with inorganic acids include salts with hydrochloric acid, hydrobromic acid, nitric acid, sulfuric acid, phosphoric acid, etc. Preferred examples of the salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, etc. Preferred examples of the salts with basic amino acids include salts with arginine, lysine, ornithine, etc., and preferred examples of the salts with acidic amino acids include salts with aspartic acid, glutamic acid, etc.

Among them, pharmacologically acceptable salts are preferred. For example, where the compounds contain acidic functional groups therein, examples include inorganic salts such as alkali metal salts (e.g., sodium salts, potassium salts, etc.), alkaline earth metal salts (e.g., calcium salts, magnesium salts, barium salts, etc.), ammonium salts, etc., and when the compounds contain basic functional groups therein, examples include salts with inorganic acids such as hydrobromic acid, nitric acid, sulfuric acid, phosphoric acid, etc., salts with organic acids such as acetic acid, phthalic acid, fumaric acid, oxalic acid, tartaric acid, maleic acid, citric acid, succinic acid, methanesulfonic acid, p-toluenesulfonic acid, etc.

The receptor of the present invention and the partial peptide of the present invention can be manufactured from the aforesaid human or warm-blooded animal cells or tissues by methods for purification of polypeptides, which are per se publicly known, or can also be manufactured by culturing transformants transformed by DNAs encoding polypeptides later described. In addition, they can also be manufactured by modifications of peptide synthesis later described. For example, the receptor and partial peptide can also be manufactured by the methods described in, e.g., Genomics, 56, 12–21, 1999, Biochim. Biophys. Acta, 1446, 57–70, 1999, etc. or by modifications of these methods.

Where the receptor and partial peptide are manufactured from human or mammalian tissues or cells, human or mammalian tissues or cells are homogenized, extracted with an acid or the like, and the extract is isolated and purified by a combination of chromatography techniques such as reverse phase chromatography, ion exchange chromatography, and the like.

To synthesize the receptor or partial peptide of the present invention or its salts, commercially available resins that are used for protein synthesis may be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylmethylphenyl acetamidomethyl resin, polyacrylamide resin, 4-(2',4'-dimethoxyphenyl-hydroxymethyl)phenoxy resin, 4-(2',4'-dimethoxyphenyl-Fmoc-aminoethyl) phenoxy resin, etc. Using these resins, amino acids, in which α-amino groups and functional groups on the side chains are appropriately protected, are condensed on the resin in the order of the sequence of the objective polypeptide according to various condensation methods publicly known in the art. At the end of the reaction, the polypeptide is excised from the resin and at the same time, the protecting groups are removed. Then, intramolecular disulfide bond-forming reaction is performed in a highly diluted solution to obtain the objective polypeptide, receptor or partial peptide, or amides thereof.

For condensation of the protected amino acids described above, a variety of activation reagents for polypeptide synthesis may be used, and carbodiimides are particularly employed. Examples of such carbodiimides include DCC, N,N'-diisopropylcarbodiimide, N-ethyl-N'-(3-dimethylaminopropyl)carbodiimide, etc. For activation by these reagents, the protected amino acids in combination with a racemization inhibitor (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents suitable for use to activate the protected amino acids or condense with the resin may be chosen from solvents that are known to be usable for polypeptide condensation reactions. Examples of such solvents are acid amides such as N,N-dimethylformamide, N,N-dimethylacetamide, N-methylpyrrolidone, etc.; halogenated hydrocarbons such as methylene chloride, chloroform, etc.; alcohols such as trifluoroethanol, etc.; sulfoxides such as dimethylsulfoxide, etc.; ethers such as pyridine, dioxane, tetrahydrofuran, etc.; nitriles such as acetonitrile, propionitrile, etc.; esters such as methyl acetate, ethyl acetate, etc.; and appropriate mixtures of these solvents. The reaction temperature is appropriately chosen from the range known to be applicable to polypeptide binding reactions and is usually selected in the range of approximately −20° C. to 50° C. The activated amino acid derivatives are used generally in an excess of 1.5 to 4 times. The condensation is examined using the ninhydrin reaction; when the condensation is insufficient, the condensation can be completed by repeating the condensation reaction without removal of the protecting groups. When the condensation is yet insufficient even after repeating the reaction, unreacted amino acids are acetylated with acetic anhydride or acetylimidazole to cancel any possible adverse affect on the subsequent reaction.

Examples of the protecting groups used to protect the starting amino groups include Z, Boc, t-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc, etc.

A carboxyl group can be protected by, e.g., alkyl esterification (linear, branched or cyclic alkyl esterification of, e.g., methyl, ethyl, propyl, butyl, t-butyl, cyclopentyl, cyclohexyl, cycloheptyl, cyclooctyl, 2-adamantyl, etc.), aralkyl esterification (e.g., benzyl ester, 4-nitrobenzyl ester, 4-methoxybenzyl ester, 4-chlorobenzyl ester, benzhydryl ester, etc.), phenacyl esterification, benzyloxycarbonyl hydrazidation, t-butoxycarbonyl hydrazidation, trityl hydrazidation, or the like.

The hydroxyl group of serine can be protected through, for example, its esterification or etherification. Examples of groups appropriately used for the esterification include a lower ($C_{1-6}$) alkanoyl group, such as acetyl group, an aroyl group such as benzoyl group, and a group derived from carbonic acid such as benzyloxycarbonyl group, ethoxycarbonyl group, etc. Examples of a group appropriately used for the etherification include benzyl group, tetrahydropyranyl group, t-butyl group, etc.

Examples of groups for protecting the phenolic hydroxyl group of tyrosine include Bzl, $Cl_2$-Bzl, 2-nitrobenzyl, Br-Z, t-butyl, etc.

Examples of groups used to protect the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups in the starting material include the corresponding acid anhydrides, azides, activated esters [esters with alcohols (e.g., pentachlorophenol, 2,4,5-trichlorophenol, 2,4-dinitrophenol, cyanomethyl alcohol, p-nitrophenol, HONB, N-hydroxysuccimide, N-hydroxyphthalimide, HOBt)]. As the amino acids in which the amino groups are activated in the starting material, the corresponding phosphoric amides are employed.

To eliminate (split off) the protecting groups, there are used catalytic reduction under hydrogen gas flow in the presence of a catalyst such as Pd-black or Pd-carbon; an acid treatment with anhydrous hydrogen fluoride, methanesulfonic acid, trifluoromethanesulfonic acid, trifluoroacetic acid, or a mixture solution of these acids; a treatment with a base such as diisopropylethylamine, triethylamine, piperidine or piperazine; reduction with sodium in liquid ammonia, etc. The elimination of the protecting group by the acid treatment described above is carried out generally at a temperature of approximately −20° C. to 40° C. In the acid treatment, it is efficient to add a cation scavenger such as anisole, phenol, thioanisole, m-cresol, p-cresol, dimethylsulfide, 1,4-butanedithiol, 1,2-ethanedithiol, etc. Furthermore, 2,4-dinitrophenyl group known as the protecting group for the imidazole of histidine is removed by a treatment with thiophenol. Formyl group used as the protecting group of the indole of tryptophan is eliminated by the aforesaid acid treatment in the presence of 1,2-ethanedithiol, 1,4-butanedithiol, etc. as well as by a treatment with an alkali such as a dilute sodium hydroxide solution, dilute ammonia, etc.

Protection of functional groups that should not be involved in the reaction of the starting materials, protecting groups, elimination of the protecting groups and activation of functional groups involved in the reaction may be appropriately selected from publicly known groups and publicly known means.

In another method for obtaining the receptor or partial peptide of the present invention, for example, the α-carboxyl group of the carboxy terminal amino acid is first protected by amidation; the peptide (polypeptide) chain is then extended from the amino group side to a desired length. Thereafter, a polypeptide, in which only the protecting group of the N-terminal α-amino group of the peptide chain has been eliminated, and a polypeptide, in which only the protecting group of the C-terminal carboxyl group has been eliminated are manufactured. The two polypeptides are condensed in a mixture of the solvents described above. The details of the condensation reaction are the same as described above. After the protected polypeptide obtained by the condensation is purified, all the protecting groups are eliminated by the method described above to give the desired crude polypeptide. This crude polypeptide is purified by various known purification means. Lyophilization of the major fraction gives the amide of the desired receptor or partial peptide.

To prepare the esterified receptor or partial peptide of the present invention or salts thereof, for example, the α-carboxyl group of the carboxy terminal amino acid is condensed with a desired alcohol to prepare the amino acid ester, which is followed by procedures similar to the preparation of the amidated receptor or partial peptide above to give the desired esterified receptor or partial peptide.

The receptor or partial peptide of the present invention can be manufactured by publicly known methods for peptide synthesis, or, in the partial peptide of the receptor, by cleaving the receptor with an appropriate peptidase. For the methods for peptide synthesis, for example, either solid phase synthesis or liquid phase synthesis may be used. That is, the partial peptide or amino acids that can constitute the receptor or partial peptide of the present invention are condensed with the remaining part. Where the product contains protecting groups, these protecting groups are removed to give the desired peptide. Publicly known methods for condensation and elimination of the protecting groups are described in (1) to (5) below.

(1) M. Bodanszky & M. A. Ondetti: Peptide Synthesis, Interscience Publishers, New York (1966)

(2) Schroeder & Luebke: The Peptide, Academic Press, New York (1965)

(3) Nobuo Izumiya, et al.: Peptide Gosei-no-Kiso to Jikken (Basics and experiments of peptide synthesis), published by Maruzen Co. (1975)

(4) Haruaki Yajima & Shunpei Sakakibara: Seikagaku Jikken Koza (Biochemical Experiment) 1, Tanpakushitsu no Kagaku (Chemistry of Proteins) IV, 205 (1977)

(5) Haruaki Yajima ed.: Zoku Iyakuhin no Kaihatsu (A sequel to Development of Pharmaceuticals), Vol. 14, Peptide Synthesis, published by Hirokawa Shoten After completion of the reaction, the receptor or partial peptide of the present invention may be purified and isolated by a combination of conventional purification methods such as solvent extraction, distillation, column chromatography, liquid chromatography and recrystallization to give the partial peptide of the present invention. When the receptor or partial peptide obtained by the above methods is in a free form, it can be converted into an appropriate salt by a publicly known method or its modifications; when the receptor or partial peptide is obtained in a salt form, it can be converted into a free form or other different salt form by a publicly known method or its modifications.

The polynucleotide encoding the receptor or partial peptide of the present invention may be any polynucleotide so long as it contains the base sequence encoding the receptor or partial peptide of the present invention described above. Among others, DNA is preferred and the DNA may be any one of genomic DNA, genomic DNA library, cDNA derived from the cells or tissues described above, cDNA library derived from the cells or tissues described above and synthetic DNA.

The vector used for the library may be any of bacteriophage, plasmid, cosmid, phagemid and the like. In addition, the DNA can be amplified by reverse transcriptase polymerase chain reaction (hereinafter abbreviated as RT-PCR) with total RNA or mRNA fraction prepared from the above-described cells or tissues.

The DNA encoding the receptor of the present invention may be, for example, (1) any one of a DNA containing the base sequence represented by SEQ ID NO: 2, or any DNA having a base sequence hybridizable to a DNA having the base sequence represented by SEQ ID NO: 2 under high stringent conditions and encoding the receptor which has the properties substantially equivalent to those of the protein containing the amino acid sequence represented by SEQ ID NO: 1, (2) any one of a DNA having the base sequence represented by SEQ ID NO: 20, or any DNA having a base sequence hybridizable to a DNA having the base sequence represented by SEQ ID NO: 20 under high stringent conditions and encoding the receptor which has the properties substantially equivalent to those of the protein containing the amino acid sequence represented by SEQ ID NO: 19, etc.

Examples of the DNA that is hybridizable to a DNA having the base sequence represented by SEQ ID NO: 2 under high stringent conditions include DNAs having at least about 70% homology, preferably at least about 80% homology, more preferably at least about 90% homology and most preferably at least about 95% homology, to the base sequence represented by SEQ ID NO: 2.

Examples of the DNA that is hybridizable to a DNA having the base sequence represented by SEQ ID NO: 20 under high stringent conditions include DNAs having at least about 95% homology, preferably at least about 97% homology and more preferably at least about 99% homology, to the base sequence represented by SEQ ID NO: 20.

The hybridization can be carried out by publicly known methods or by a modification thereof, for example, according to the method described in Molecular Cloning, 2nd ed. (J. Sambrook et al. Cold Spring Harbor. Lab. Press, 1989). A commercially available library can also be used according to the instructions of the attached manufacturer's protocol. The hybridization can be carried out preferably under high stringent conditions.

The high stringent conditions used herein are, for example, those in a sodium concentration at about 19 to 40 mM, preferably about 19 to 20 mM at a temperature of about 50 to 70° C., preferably about 60 to 65° C. In particular, hybridization conditions in a sodium concentration at about 19 mM at a temperature of about 65° C. are most preferred.

More specifically, as the DNA encoding the receptor containing the amino acid sequence represented by SEQ:ID NO: 1, there may be employed a DNA containing the base sequence represented by SEQ ID NO: 2, etc. As the DNA encoding the receptor containing the amino acid sequence represented by SEQ ID NO: 19, there may be employed a DNA containing the base sequence represented by SEQ ID NO: 20, etc.

The DNA encoding the partial peptide of the present invention may be any DNA so long as it contains the base sequence encoding the partial peptide of the receptor of the present invention. The DNA may also be any of genomic DNA, genomic DNA library, cDNA derived from the cells and tissues described above, cDNA library derived from the cells and tissues described above and synthetic DNA. Specifically, there are employed a DNA having a part of base sequence of a DNA having the base sequence represented by SEQ ID NO: 2 or SEQ ID NO: 20, or a DNA having a base sequence hybridizable to the base sequence represented by SEQ ID NO: 2 or SEQ ID NO: 20 under high stringent conditions and containing a part of DNA encoding the receptor having the activities substantially equivalent to those of the protein containing the amino acid sequence represented by SEQ ID NO: 1 or, SEQ ID NO: 19, etc.

The DNA hybridizable to the base sequence represented by SEQ ID NO: 2 or SEQ ID NO: 20 has the same significance as described above.

Methods for the hybridization and the high stringent conditions that can be used are the same as those described above.

The polypeptide (e.g., DNA) encoding the receptor or partial peptide of the present invention may be labeled by methods publicly known. As the labeling agent, there are radioisotopes, fluorescent substances (e.g., fluorescein, etc.), luminescent substances, enzymes, biotin, lanthanides, etc.

For cloning of DNAs that completely encode the receptor or partial peptide of the present invention, the DNA can be either amplified by PCR using synthetic DNA primers containing a part of the base sequence of the receptor or partial peptide of the present invention, or the DNA inserted into an appropriate vector can be screened by hybridization with a labeled DNA fragment or synthetic DNA that encodes a part or entire region of the receptor or partial peptide of the present invention. The hybridization can be carried out, for example, according to the method described in Molecular Cloning, 2nd (J. Sambrook et al., Cold Spring. Harbor Lab. Press, 1989). Where the hybridization is carried out using commercially available library, the procedures may be conducted in accordance with the protocol described in the attached instructions.

Conversion of the base sequence of DNA can be effected by publicly known methods such as the ODA-LA PCR method, the Gapped duplex method, the Kunkel method, etc., or its modifications, using a publicly known kit available as Mutan™-super Express Km (manufactured by Takara Shuzo Co., Ltd.) or Mutan™-K (manufactured by Takara Shuzo Co., Ltd.), etc.

The cloned DNA encoding the receptor can be used as it is, depending upon purpose or, if desired, after digestion with a restriction enzyme or after addition of a linker thereto. The DNA may contain ATG as a translation initiation codon at the 5' end thereof and TAA, TGA or TAG as a translation termination codon at the 3' end thereof. These translation initiation and termination codons may also be added by using an appropriate synthetic DNA adapter.

The expression vector for the receptor or partial peptide of the present invention can be manufactured, for example, by (a) excising the desired DNA fragment from the DNA encoding the receptor or partial peptide of the present invention, and then (b) ligating the DNA fragment with an appropriate expression vector downstream a promoter in the vector.

Examples of the vector include plasmids derived form *E. coli* (e.g., pBR322, pBR325, pUC12, pUC13), plasmids derived from *Bacillus subtilis* (e.g., pUB110, pTP5, pC194), plasmids derived from yeast (e.g., pSH19, pSH15), bacteriophages such as λ phage, etc., animal viruses such as retrovirus, vaccinia virus, baculovirus, etc. as well as pA1-11, pXT1, pRc/CMV, pRc/RSV, pcDNA I/Neo, etc.

The promoter used in the present invention may be any promoter if it matches well with a host to be used for gene expression. In the case of using animal cells as the host, examples of the promoter include SRα promoter, SV40 promoter, LTR promoter, CMV promoter, HSV-TK promoter, etc.

Among them, it is preferred to use CMV (cytomegalovirus) promoter, SRα promoter, etc. Where the host is bacteria of the genus *Escherichia*, preferred examples of the promoter include trp promoter, lac promoter, recA promoter, λP$_L$ promoter, lpp promoter, T7 promoter, etc. In the case of using bacteria of the genus *Bacillus* as the host, preferred example of the promoter are SPO1 promoter, SPO2 promoter, penP promoter, etc. When yeast is used as the host, preferred examples of the promoter are PHO5 promoter, PGK promoter, GAP promoter, ADH promoter, etc. When insect cells are used as the host, preferred examples of the promoter include polyhedrin prompter, P10 promoter, etc.

In addition to the foregoing examples, the expression vector may further optionally contain an enhancer, a splicing signal, a poly A addition signal, a selection marker, SV40 replication origin (hereinafter sometimes abbreviated as SV40ori), etc. Examples of the selection marker include dihydrofolate reductase (hereinafter sometimes abbreviated as dhfr) gene [methotrexate (MTX) resistance], ampicillin resistant gene (hereinafter sometimes abbreviated as Amp$^r$), neomycin resistant gene (hereinafter sometimes abbreviated as Neo$^r$, G418 resistance), etc. In particular, when dhfr gene is used as the selection marker using dhfr gene-deficient Chinese hamster cells, selection can also be made on a thymidine free medium.

If necessary, a signal sequence that matches with a host is added to the N-terminus of the receptor of the present invention. Examples of the signal sequence that can be used are PhoA signal sequence, OmpA signal sequence, etc. when bacteria of the genus *Escherichia* is used as the host; α-amylase signal sequence, subtilisin signal sequence, etc. when bacteria of the genus *Bacillus* is used as the host; MFα signal sequence, SUC2 signal sequence, etc. when yeast is used as the host; and insulin signal sequence, α-interferon signal sequence, antibody molecule signal sequence, etc. when animal cells are used as the host, respectively.

Using the vector containing the DNA encoding the receptor or partial peptide of the present invention thus constructed, transformants can be manufactured.

Examples of the host, which may be employed, are bacteria belonging to the genus *Escherichia*, bacteria belonging to the genus *Bacillus*, yeast, insect cells, insects and animal cells, etc.

Specific examples of the bacteria belonging to the genus *Escherichia* include *Escherichia coli* K12 DH1 [Proc. Natl. Acad. Sci. U.S.A., 60; 160 (1968)], JM103 [Nucleic Acids Research, 9, 309 (1981)], JA221 [Journal of Molecular Biology, 120, 517 (1978)], HB101 [Journal of Molecular Biology, 41, 459 (1969)], C600 [Genetics, 39, 440 (1954)], etc.

Examples of the bacteria belonging to the genus *Bacillus* include *Bacillus subtilis* MI114 [Gene, 24, 255 (1983)], 207–21 [Journal of Biochemistry, 95, 87 (1984)], etc.

Examples of yeast include *Saccharomyces cereviseae* AH22, AH22R⁻, NA87-11A, DKD-5D, 20B-12, *Schizosaccharomyces pombe* NCYC1913, NCYC2036, *Pichia pastoris* KM71, etc.

Examples of insect cells include, for the virus AcNPV, *Spodoptera frugiperda* cell (Sf cell), MG1 cell derived from mid-intestine of Trichoplusia ni, High Five™ cell derived from egg of Trichoplusia ni, cells derived from *Mamestra brassicae*, cells derived from Estigmena acrea, etc.; and for the virus BmNPV, *Bombyx mori* N cell (BmN cell), etc. is used. Examples of the Sf cell which can be used are Sf9 cell (ATCC CRL1711), Sf21 cell (both cells are described in Vaughn, J. L. et al., In Vivo, 13, 213–217 (1977), etc.

As the insect, for example, a larva of *Bombyx mori* can be used [Maeda et al., Nature, 315, 592 (1985)].

Examples of animal cells include monkey cell COS-7, Vero, Chinese hamster cell CHO (hereinafter referred to as CHO cell), dhfr gene-deficient Chinese hamster cell CHO (hereinafter simply referred to as CHO (dhfr) cell), mouse L cell, mouse AtT-20, mouse myeloma cell, rat GH 3, human FL cell, etc.

Bacteria belonging to the genus *Escherichia* can be transformed, for example, by the method described in Proc. Natl. Acad. Sci. U.S.A., 69, 2110 (1972), Gene, 17, 107 (1982), etc.

Bacteria belonging to the genus *Bacillus* can be transformed, for example, by the method described in Molecular & General Genetics, 168, 111 (1979), etc.

Yeast can be transformed, for example, by the method described in Methods in Enzymology, 194, 182–187 (1991), Proc. Natl. Acad. Sci. U.S.A., 75, 1929 (1978), etc.

Insect cells or insects can be transformed, for example, according to the method described in Bio/Technology, 6, 47–55(1988), etc.

Animal cells can be transformed, for example, according to the method described in Saibo Kogaku (Cell Engineering), extra issue 8, Shin Saibo Kogaku Jikken Protocol (New Cell Engineering Experimental Protocol), 263–267 (1995) (published by Shujunsha), or Virology, 52, 456 (1973).

Thus, the transformants transformed with the expression vectors containing the DNAs encoding the receptor or partial peptide can be obtained.

Where the host is bacteria belonging to the genus *Escherichia* or the genus *Bacillus*, the transformant can be appropriately cultured in a liquid medium which contains materials required for growth of the transformant such as carbon sources, nitrogen sources, inorganic materials, and the like. Examples of the carbon sources include glucose, dextrin, soluble starch, sucrose, etc.; examples of the nitrogen sources include inorganic or organic materials such as ammonium salts, nitrate salts, corn steep liquor, peptone, casein, meat extract, soybean cake, potato extract, etc.; and, examples of the inorganic materials are calcium chloride, sodium dihydrogenphosphate, magnesium chloride, etc. In addition, yeast extracts, vitamins, growth promoting factors etc. may also be added to the medium. Preferably, pH of the medium is adjusted to about 5 to about 8.

A preferred example of the medium for culturing the bacteria belonging to the genus *Escherichia* is M9 medium supplemented with glucose and Casamino acids [Miller, Journal of Experiments in Molecular Genetics, 431–433, Cold Spring Harbor Laboratory, New York, 1972]. If necessary, a chemical such as 3β-indolylacrylic acid can be added to the medium thereby to activate the promoter efficiently.

Where the bacteria belonging to the genus *Escherichia* are used as the host, the transformant is usually cultivated at about 15 to 43° C. for about 3 to 24 hours. If necessary, the culture may be aerated or agitated.

Where the bacteria belonging to the genus *Bacillus* are used as the host, the transformant is cultured generally at about 30 to 40° C. for about 6 to 24 hours. If necessary, the culture can be aerated or agitated.

Where yeast is used as the host, the transformant is cultivated, for example, in Burkholder's minimal medium [Bostian, K. L. et al., Proc. Natl. Acad. Sci. U.S.A., 77, 4505 (1980)] or in SD medium supplemented with 0.5% Casamino acids [Bitter, G. A. et al., Proc. Natl. Acad. Sci. U.S.A., 81, 5330 (1984)]. Preferably, pH of the medium is adjusted to about 5 to 8. In general, the transformant is cultivated at about 20 to 35° C. for about 24 to 72 hours. If necessary, the culture can be aerated or agitated.

Where insect cells or insects are used as the host, the transformant is cultivated in, for example, Grace's Insect Medium (Grace, T. C. C., Nature, 195, 788 (1962)) to which an appropriate additive such as immobilized 10% bovine serum is added. Preferably, pH of the medium is adjusted to about 6.2 to about 6.4. Normally, the transformant is cultivated at about 27° C. for about 3 days to about 5 days and, if necessary, the culture can be aerated or agitated.

Where animal cells are employed as the host, the transformant is cultured in, for example, MEM medium containing about 5 to 20% fetal bovine serum [Science, 122, 501 (1952)], DMEM medium [Virology, 8, 396 (1959)], RPMI 1640 medium [The Journal of the American Medical Association, 199, 519 (1967)], 199 medium [Proceeding of the Society for the Biological Medicine, 73, 1 (1950)], etc. Preferably, pH of the medium is adjusted to about 6 to about 8. The transformant is usually cultivated at about 30° C. to about 40° C. for about 15 to 60 hours and, if necessary, the culture can be aerated or agitated.

As described above, the receptor or partial peptide of the present invention can be produced in the transformant, on the cell membrane of the transformant, or outside of the transformant.

The receptor or partial peptide of the present invention can be separated and purified from the culture described above by the following procedures.

When the receptor or partial peptide of the present invention is extracted from the bacteria or cells, the bacteria or cell is collected after culturing by a publicly known method and suspended in an appropriate buffer. The bacteria or cell is then disrupted by publicly known methods such as ultrasonication, a treatment with lysozyme and/or freeze-thaw cycling, followed by centrifugation, filtration, etc. Thus, the crude extract of the polypeptide can be obtained. The buffer used for the procedures may contain a protein modifier such as urea or guanidine hydrochloride, or a surfactant such as Triton X-100™, etc. When the polypeptide is secreted in the culture broth, the supernatant can be separated, after completion of the cultivation, from the bacteria or cell to collect the supernatant by a publicly known method.

The receptor or partial peptide contained in the supernatant or the extract thus obtained can be purified by appropriately combining the publicly known methods for separation and purification. Such publicly known methods for separation and purification include a method utilizing difference in solubility such as salting out, solvent precipitation, etc.; a method mainly utilizing difference in molecular weight such as dialysis, ultrafiltration, gel filtration, SDS-polyacrylamide gel electrophoresis, etc.; a method utilizing difference in electric charge such as ion exchange chromatography, etc.; a method utilizing difference in specific affinity such as affinity chromatography, etc.; a method utilizing difference in hydrophobicity such as reverse phase high performance liquid chromatography, etc.; a method utilizing difference in isoelectric point such as isoelectrofocusing electrophoresis; and the like.

When the receptor or partial peptide thus obtained is in a free form, it can be converted into the salt by publicly known methods or modifications thereof. On the other hand, when the receptor or partial peptide is obtained in the form of a salt, it can be converted into the free form or in the form of a different salt by publicly known methods or modifications thereof.

The receptor or partial peptide produced by the recombinant can be treated, prior to or after the purification, with an appropriate protein-modifying enzyme so that the polypeptide can be appropriately modified to partially remove the polypeptide. Examples of the protein-modifying enzyme include trypsin, chymotrypsin, arginyl endopeptidase, protein kinase, glycosidase and the like.

The ligand capable of binding specifically to the receptor of the present invention can be used as it is when commercially available, or can be extracted or manufactured by publicly known methods or its modifications The antibodies to the protein containing the same or substantially the same amino acid sequence represented by SEQ ID NO: 1 or SEQ ID NO: 19, its partial peptide, or salts thereof (hereinafter sometimes simply referred to as the antibody of the present invention) may be any of polyclonal and monoclonal antibodies, as long as they are capable of recognizing the antibodies to the receptor of the present invention. As the antibodies to the receptor of the present invention, there are antibodies which inactivate signal transduction of the receptor, antibodies which activate signal transduction of the receptor, etc.

The antibodies to the receptor of the present invention can be produced by publicly known methods of producing an antibody or antiserum, using the receptor of the present invention as an antigen.

[Preparation of Monoclonal Antibody]

(a) Preparation of Monoclonal Antibody-Producing Cells

The receptor of the present invention is administered to warm-blooded animals either solely or together with carriers or diluents to the site where the production of antibody is possible by the administration. In order to potentiate the antibody productivity upon the administration, complete Freund's adjuvants or incomplete Freund's adjuvants may be administered. The administration is usually carried out once every about 2 to about 6 weeks and about 2 to about 10 times in total. Examples of the applicable warm-blooded animals are monkeys, rabbits, dogs, guinea pigs, mice, rats, sheep, goats and fowl, with the use of mice and rats being preferred.

In the preparation of monoclonal antibody-producing cells, a warm-blooded animal, e.g., mice, immunized with an antigen wherein the antibody titer is noted is selected, then spleen or lymph node is collected after 2 to 5 days from the final immunization and antibody-producing cells contained therein are fused with myeloma cells from homozoic or heterozoic animal to give monoclonal antibody-producing hybridomas. Measurement of the antibody titer in antisera may be carried out, for example, by reacting a labeled polypeptide, which will be described later, with the antiserum followed by assaying the binding activity of the labeling agent bound to the antibody. The fusion may be carried out, for example, by the known method by Koehler and Milstein [Nature, 256, 495, (1975)]. Examples of the fusion accelerator are polyethylene glycol (PEG), Sendai virus, etc., of which PEG is preferably employed.

Examples of the myeloma cells are those collected from warm-blooded animals such as NS-1, P3U1, SP2/0, AP-1, etc. In particular, P3U1 is preferably employed. A preferred ratio of the count of the antibody-producing cells used (spleen cells) to the count of myeloma cells is within a range of approximately 1:1 to 20:1. When PEG (preferably, PEG 1000 to PEG 6000) is added in a concentration of approximately 10 to 80% followed by incubation at 20 to 40° C., preferably at 30 to 37° C. for 1 to 10 minutes, an efficient cell fusion can be carried out.

Various methods can be used for screening of monoclonal antibody-producing hybridomas. Examples of such methods include a method which comprises adding the supernatant of a hybridoma to a solid phase (e.g., a microplate) adsorbed with the polypeptide (protein) as an antigen directly or together with a carrier, adding an anti-immunoglobulin antibody (where mouse cells are used for the cell fusion, anti-mouse immunoglobulin antibody is used) labeled with a radioactive substance or an enzyme or protein A and detecting the monoclonal antibody bound to the solid phase, and a method which comprises adding the supernatant of hybridoma to a solid phase adsorbed with an anti-immunoglobulin antibody or protein A, adding the polypeptide labeled with a radioactive substance or an enzyme and detecting the monoclonal antibody bound to the solid phase, or the like.

The monoclonal antibody can be screened according to publicly known methods or their modifications. In general, the screening can be performed in a medium for animal cells supplemented with HAT (hypoxanthine, aminopterin and thymidine). Any screening and growth medium can be employed as far as the hybridoma can grow there. For example, RPMI 1640 medium containing 1 to 20%, preferably 10 to 20% fetal bovine serum, GIT medium (Wako Pure Chemical Industries, Ltd.) containing 1 to 10% fetal bovine serum, a serum free medium for cultivation of a hybridoma (SFM-101, Nissui Seiyaku Co., Ltd.) and the like, can be used for the screening and growth medium. The culture is carried out generally at 20 to 40° C., preferably at 37° C., for about 5 days to about 3 weeks, preferably 1 to 2 weeks, normally in 5% $CO_2$. The antibody titer of the culture supernatant of a hybridoma can be determined as in the assay for the antibody titer in antisera described above.

(b) Purification of Monoclonal Antibody

Separation and purification of a monoclonal antibody can be carried out by publicly known methods, such as separation and purification of immunoglobulins [for example, salting-out, alcohol precipitation, isoelectric point precipitation, electrophoresis, adsorption and desorption with ion exchangers (e.g., DEAE), ultracentrifugation, gel filtration, or a specific purification method which comprises collecting only an antibody with an activated adsorbent such as an antigen-binding solid phase, Protein A or Protein G and dissociating the binding to obtain the antibody.]

[Preparation of Polyclonal Antibody]

The polyclonal antibody of the present invention can be manufactured by publicly known methods or modifications thereof. For example, a warm-blooded animal is immunized with an immunogen (polypeptide antigen) per se, or a complex of immunogen and a carrier protein is formed and a warm-blooded animal is immunized with the complex in a manner similar to the method described above for the manufacture of monoclonal antibodies. The product containing the antibody to the receptor of the present invention is collected from the immunized animal followed by separation and purification of the antibody.

In the complex of immunogen and carrier protein used to immunize a warm-blooded animal, the type of carrier protein and the mixing ratio of carrier to hapten may be any type and in any ratio, as long as the antibody is efficiently produced to the hapten immunized by crosslinking to the carrier. For example, bovine serum albumin, bovine thyroglobulin or hemocyanin is coupled to hapten in a carrier-to-hapten weight ratio of approximately 0.1 to 20, preferably about 1 to 5.

A variety of condensation agents can be used for the coupling of carrier to hapten. Glutaraldehyde, carbodiimide, maleimide activated ester and activated ester reagents containing thiol group or dithiopyridyl group are used for the coupling.

The condensation product is administered to warm-blooded animals either solely or together with carriers or diluents to the site that can produce the antibody by the administration. In order to potentiate the antibody productivity upon the administration, complete Freund's adjuvant or incomplete Freund's adjuvant may be administered. The administration is usually made once every about 2 to 6 weeks and about 3 to 10 times in total.

The polyclonal antibody can be collected from the blood, ascites, etc., preferably from the blood of warm-blooded animal immunized by the method described above.

The polyclonal antibody titer in antiserum can be assayed by the same procedure as that for the determination of serum antibody titer described above. The separation and purification of the polyclonal antibody can be carried out, following the method for the separation and purification of immunoglobulins performed as in the separation and purification of monoclonal antibodies described hereinabove.

The polynucleotide (e.g., DNA) containing a complementary or substantial complementary base sequence to a polynucleotide (e.g., DNA) encoding the protein containing the same or substantially the same amino acid sequence represented by SEQ ID NO: 1 or SEQ ID NO: 19, its partial peptide or a salt thereof can be any polynucleotide (antisense polynucleotide), so long as it contains a base sequence complementary or substantially complementary to the polynucleotide, or a part of the base sequence and capable of suppressing expression of the polynucleotide.

Specific examples of the polynucleotide include antisense DNAs (hereinafter these DNAs are sometimes simply referred to as the antisense DNA of the present invention) containing a base sequence complementary or substantially complementary to polynucleotides (e.g., DNAs) encoding the receptor of the present invention (hereinafter these DNAs are sometimes simply referred to as the DNA of the present invention) or a part of the base sequence, and can be any antisense DNA, so long as it contains the complementary or substantially complementary base sequence to the DNA of the present invention, or a part of the base sequence and capable of suppressing expression of the DNA.

The base sequence substantially complementary to the DNA of the present invention includes, for example, a base sequence having at least about 70% homology, preferably at least about 80% homology, more preferably at least about 90% homology and most preferably at least about 95% homology, to the entire base sequence or to its partial base sequence (i.e., complementary strand to the DNA of the present invention) of the DNA of the present invention, and the like. Especially in the entire base sequence of the complementary strand to the DNA of the present invention, preferred is an antisense DNA having at least about 70% homology, preferably at least about 80% homology, more preferably at least about 90% homology and most preferably at least about 95% homology, to the complementary strand of the base sequence which encodes the N-terminal region of the receptor of the present invention (e.g., the base sequence near the initiation codon, etc.). These antisense DNAs can be manufactured using DNA synthesizers publicly known.

Specific examples include an antisense polynucleotide containing the entire or part of a base sequence complementary or substantially complementary to the base sequence of DNA containing the base sequence represented by SEQ ID NO: 20, or an antisense polynucleotide containing the entire or part of a base sequence complementary or substantially complementary to the base sequence of DNA containing the base sequence represented by SEQ ID NO: 2, etc. Preferably, the antisense polynucleotide is an antisense polynucleotide containing the entire or part of a base sequence complementary to a base sequence of DNA containing the base sequence represented by SEQ ID NO: 20, or an antisense polynucleotide containing the entire or part of a base sequence complementary to a base sequence of DNA containing the base sequence represented by SEQ ID NO: 2, etc.

The antisense polynucleotide is generally constituted by bases of about 10 to about 40, preferably about 15 to about 30.

To prevent digestion with a hydrolase such as nuclease, etc., the phosphoric acid residue (phosphate) of each nucleotide that constitutes the antisense DNA may be substituted with chemically modified phosphoric acid residues, e.g., phosphorothioate, methyl phosphonate, phosphorodithionate, etc. These antisense polynucleotides may be synthesized using a publicly known DNA synthesizer, etc.

According to the present invention, the antisense polynucleotide (nucleic acid) that can inhibit replication or expression of a gene for the receptor of the present invention can be designed and synthesized based on the base sequence information of the cloned DNA or DNA encoding the protein, which amino acids were determined. Such a polynucleotide (nucleic acid) can hybridize to RNA of a gene for the receptor of the present invention to inhibit the synthesis or function of said RNA or is capable of regulating/controlling the expression of the gene for the receptor of the present invention via interaction with RNA associated with the receptor of the present invention. The polynucleotides complementary to the selected sequences of RNA associated with the receptor of the present invention and polynucleotides specifically hybridizable to RNA associated with the receptor of the present invention are useful in regulating/controlling the in vivo and in vitro expression of the gene for the receptor of the present invention, and are useful for the treatment or diagnosis of diseases, etc. The term "corresponding" is used to mean homologous to or complementary to a particular sequence of the nucleotide including the gene, base sequence or nucleic acid. The term "corresponding" between nucleotides, base sequences or nucleic acids and peptides (proteins) usually refer to amino acids of a peptide (protein) under the order derived from the sequence of nucleotides (nucleic acids) or their complements. In the receptor genes, the 5' end hairpin loop, 5' end 6-base-pair repeats, 5' end untranslated region, polypeptide translation initiation codon, receptor coding region, ORF translation termination codon, 3' end untranslated region, 3' end palindrome region, and 3' end hairpin loop, may be selected as preferred target regions, though any other region may be selected as a target in the protein genes.

The relationship between the targeted nucleic acids and the polynucleotides complementary to at least a part of the target region, specifically the relationship between the target nucleic acids and the polynucleotides hybridizable to the target region, can be denoted to be "antisense" to the polynucleotides in the said target region. Examples of the antisense polynucleotides include polynucleotides containing 2-deoxy-D-ribose, polynucleotides containing D-ribose, any other type of polynucleotides which are N-glycosides of a purine or pyrimidine base, or other polymers containing non-nucleotide backbones (e.g., commercially available protein nucleic acids and synthetic sequence-specific nucleic acid polymers) or other polymers containing nonstandard linkages (provided that the polymers contain nucleotides having such a configuration that allows base pairing or base stacking, as is found in DNA or RNA), etc. The antisense polynucleotides may be double-stranded DNA, single-stranded DNA, double-stranded RNA, single-stranded RNA or a DNA:RNA hybrid, and may further include unmodified polynucleotides (or unmodified oligonucleotides), those with publicly known types of modifications, for example, those with labels known in the art, those with caps, methylated polynucleotides, those with substitution of one or more naturally occurring nucleotides by their analogue, those with intramolecular modifications of nucleotides such as those with uncharged linkages (e.g., methyl phosphonates, phosphotriesters, phosphoramidates, carbamates, etc.) and those with charged linkages or sulfur-containing linkages (e.g., phosphorothioates, phosphorodithioates, etc.), those having side chain groups such as proteins (nucleases, nuclease inhibitors, toxins, antibodies, signal peptides, poly-L-lysine, etc.), saccharides (e.g., monosaccharides, etc.), those with intercalators (e.g., acridine, psoralen, etc.), those containing chelators (e.g., metals, radioactive-metals, boron, oxidative metals, etc.), those containing alkylating agents, those with modified linkages (e.g., $\alpha$ anomeric nucleic acids, etc.), and the like. Herein the terms "nucleoside", "nucleotide" and "nucleic acid" are used to refer to moieties that contain not only the purine and pyrimidine bases, but also other heterocyclic bases, which have been modified. Such modifications may include methylated purines and pyrimidines, acylated purines and pyrimidines and other heterocyclic rings. Modified nucleotides and modified nucleotides also include modifications on the sugar moiety, wherein, for example, one or more hydroxyl groups may optionally be substituted with a halogen atom(s), an aliphatic group(s), etc., or may be converted into the corresponding functional groups such as ethers, amines, or the like.

The antisense polynucleotide (nucleic acid) of the present invention is RNA, DNA or a modified nucleic acid (RNA, DNA). Specific examples of the modified nucleic acid are, but not limited to, sulfur and thiophosphate derivatives of nucleic acids and those resistant to degradation of polynucleoside amides or oligonucleoside amides. The antisense nucleic acids of the present invention can be modified preferably based on the following design, that is, by increasing the intracellular stability of the antisense nucleic acid, increasing the cell permeability of the antisense nucleic acid, increasing the affinity of the nucleic acid to the targeted sense strand to a higher level, or minimizing the toxicity, if any, of the antisense nucleic acid.

Many of such modifications are known in the art, as disclosed in J. Kawakami, et al., Pharm. Tech. Japan, Vol. 8, pp. 247, 1992; Vol. 8, pp. 395, 1992; S. T. Crooke, et al. ed., Antisense Research and Applications, CRC Press, 1993; etc.

The antisense polynucleotide of the present invention may contain altered or modified sugars, bases or linkages. The antisense polynucleotide may also be provided in a specialized form such as liposomes, microspheres, or may be applied to gene therapy, or may be provided in combination with attached moieties. Such attached moieties include polycations such as polylysine that act as charge neutralizers of the phosphate backbone, or hydrophobic moieties such as lipids (e.g., phospholipids, cholesterols, etc.) that enhance the interaction with cell membranes or increase uptake of the nucleic acid. Preferred examples of the lipids to be attached are cholesterols or derivatives thereof (e.g., cholesteryl chloroformate, cholic acid, etc.). These moieties may be attached to the nucleic acid at the 3' or 5' ends thereof and may also be attached thereto through a base, sugar, or intramolecular nucleoside linkage. Other moieties, may be capping groups specifically placed at the 3' or 5' ends of the nucleic acid to prevent degradation by nucleases such as exonuclease, RNase, etc. Such capping groups include, but are not limited to, hydroxyl protecting groups known in the art, including glycols such as polyethylene glycol, tetraethylene glycol and the like.

The inhibitory action of the antisense nucleotide can be examined using the transformant of the present invention, the gene expression system of the present invention in, vivo and in vitro, or the translation system of the receptor of the present invention in vivo and in vitro. The nucleic acid can be applied to cells by a variety of publicly known methods.

Hereinafter description is made on (i) the receptor of the present invention, (ii) the polynucleotide encoding the receptor of the present invention (the polynucleotide of the present invention), (iii) the antibody to the receptor of the present invention (the antibody of the present invention), (iv) the antisense polynucleotide of the receptor of the present invention (e.g., the antisense DNA of the present invention), (v) the ligand capable of binding specifically to the receptor of the present invention (the ligand of the present invention), etc.

[1] Screening of Drug Candidate Compounds for Diseases

The ligand of the present invention possesses the histamine release activity on rat mast cells stimulated by antigen or concanavalin A, the activity of releasing histamine by synergistically acting on rat mast cells together with nerve growth factor (NGF), the growth regulating activity on human T cells, the activity of potentiating the differentiation-inducing ability of NGF on PC12 cells, the blood coagulation inhibitory activity, the platelet agglutination response inhibitory activity, etc.

Using the receptor of the present invention, or using the ligand-receptor assay system using the expression system of the receptor of the present invention in its recombinant form, compounds (e.g., peptides, proteins, non-peptide compounds, synthetic compounds, fermentation products, etc.) or salts thereof that change the binding properties of the receptor of the present invention to the ligand of the present invention can be efficiently screened.

The compounds or salts thereof include (i) compounds that have the cell-stimulating activities (e.g., the activities of promoting arachidonic acid release, acetylcholine release, intracellular $Ca^{2+}$ release, intracellular cAMP production, intracellular cGMP production, inositol phosphate production, changes in cell membrane potential, phosphorylation of intracellular proteins, activation of c-fos, pH reduction, GTPγS binding activity, activation of cAMP-dependent protein kinase, activation of cGMP-dependent protein kinase, activation of phospholipid-dependent protein kinase, activation of microtubule-associated protein kinase (MAP kinase), etc.) mediated by the receptor of the present invention (agonists), (ii) compounds that do not have the cell-stimulating activities described above (antagonists), (iii) compounds that promote the binding of the receptor of the present invention to the ligand of the present invention, (iv) compounds that inhibit the binding of the receptor of the present invention to the ligand of the present invention, and the like.

Specifically, comparison is made between (i) when the ligand of the present invention is brought in contact with the receptor of the present invention, and (ii) when the ligand of the present invention and a test compound are brought in contact with the receptor of the present invention. The comparison is effected, e.g., by determining the amount of the ligand of the present invention bound to the receptor of the present invention, the cell stimulating activities, etc.

Specifically, the screening method of the present invention includes the receptor-binding assay system such as:

(a) a method of screening a compound or its salt that changes the binding properties of the ligand of the present invention to the receptor of the present invention, which comprises assaying the binding amounts of the ligand of the present invention to the receptor of the present invention, when the ligand of the present invention is brought in contact with the receptor of the present invention and when the ligand of the present invention and a test compound are brought in contact with the receptor of the present invention, and comparing the binding amounts;

(b) a method of screening a compound or its salt that changes the binding properties of the ligand of the present invention to the receptor of the present invention, which comprises assaying the binding amounts of the ligand of the present invention to a cell containing the receptor of the present invention or a membrane fraction of the cell, when the ligand of the present invention is brought in contact with the cell containing the receptor of the present invention or its membrane fraction and when the ligand of the present invention and a test compound are brought in contact with the cell containing the receptor of the present invention or its membrane fraction, and comparing the binding amounts; and, (c) a method of screening as described in (b) above, wherein the receptor of the present invention is the receptor of the present invention expressed on a cell membrane by culturing a transformant containing a DNA encoding the receptor of the present invention;

(d) a method of screening as described in (a) through (c) above, wherein the ligand of the present invention is a labeled ligand; etc.; and, the cell stimulating assay system such as:

(e) a method of screening a compound or its salt that changes the binding properties of the ligand of the present invention to the receptor of the present invention, which comprises assaying the cell-stimulating activities mediated by the receptor of the present invention, when the ligand of the present invention is brought in contact with the receptor of the present invention and when the ligand of the present invention and a test compound are brought in contact with the receptor of the present invention, and comparing the activities;

(f) a method of screening a compound or its salt that changes the binding properties of the ligand of the present invention to the receptor of the present invention, which comprises assaying the cell-stimulating activities mediated by the receptor of the present invention, when the ligand of the present invention is brought in contact with a cell containing the receptor of the present invention or a membrane fraction of the cell, and when the ligand of the present invention and a test compound are brought in contact with the cell or its membrane fracation containing the receptor of the present invention;

(g) a method of screening as described in (f) above, wherein the receptor of the present invention is the receptor of the present invention expressed on a cell membrane by culturing a transformant containing a DNA encoding the receptor of the present invention; etc.

The screening method of the present invention will be described below more specifically.

As the receptor of the present invention, membrane fractions from human or warm-blooded animal organs are preferably employed. However, it is very difficult to obtain human-derived organs among others, and the receptor of the present invention, etc. expressed abundantly by use of recombinants are suitable for use in the screening.

In the manufacture of the receptor of the present invention, the methods of manufacturing the receptor of the present invention described above may be used.

Where a cell containing the receptor of the present invention or a membrane fraction of the cell is used in the screening method of the present invention, the procedures later described apply to the method.

When the cell containing the receptor of the present invention is used in the screening method of the present invention, the cell may be fixed with glutaraldehyde, formalin, etc. The fixation may be carried out by a publicly known method.

The cell containing the receptor of the present invention refers to a host cell in which the receptor of the present invention is expressed. Examples of such a host cell include *Escherichia coli, Bacillus subtilis*, yeast, insect cells, animal cells, etc. The host cells can be prepared in a manner similar to the above-stated method.

The membrane fraction refers to a fraction that abundantly contains cell membranes prepared by publicly known methods after disrupting cells. Examples of the cell disruption include cell squashing using a Potter-Elvehjem homogenizer, disruption using a Waring blender or Polytron (manufactured by Kinematica Inc.), disruption by ultrasonication, disruption by cell spraying via a thin nozzle under increasing pressure using a French press, etc., and the like. Cell membranes are fractionated mainly by fractionation using a centrifugal force such as for fractionation centrifugation, density gradient centrifugation, etc. For example, cell disruption fluid is centrifuged at a low rate (500 rpm to 3,000 rpm) for a short period of time (normally about 1 minute to about 10 minutes), the resulting supernatant is then centrifuged at a higher rate (15,000 rpm to 30,000 rpm) normally for 30 minutes to 2 hours. The precipitate thus obtained is used as the membrane fraction. The membrane fraction is rich in the receptor of the present invention expressed and membrane components such as cell-derived phospholipids, membrane proteins, or the like.

The amount of the receptor of the present invention contained in the cells containing the receptor of the present invention or in the membrane fraction is preferably $10^3$ to $10^8$ molecules per cell, more preferably $10^5$ to $10^7$ molecules per cell. As the amount of expression increases, the ligand binding activity per unit of membrane fraction (specific activity) increases so that not only the highly sensitive screening system can be constructed but also large quantities of samples can be assayed with the same lot.

To perform the screening methods of the receptor-binding assay system, the cell stimulating assay system, etc. described above, for example, a fraction of the receptor of the present invention and the ligand of the present invention (a labeled form of the ligand of the present invention), etc. are used. The fraction of the receptor of the present invention is preferably a fraction of a naturally occurring form of the receptor of the present invention or a fraction of the receptor of the present invention in recombinant type having an equivalent activity. Herein, the term equivalent activity is intended to mean the ligand binding activities, etc. which are equivalent. As the labeled ligand, there may be used, for example, ligands, which are labeled with radioisotopes (e.g., [$^3$H], [$^{125}$I], [$^{14}$C], [$^{32}$P], [$^{33}$P], [$^{35}$S], etc.), fluorescent substances (e.g., fluorescein, etc.), luminescent substances (e.g., luminol, etc.), enzymes (e.g., a peroxidase, etc.), a lanthanide, etc.

More specifically, for screening the compound that changes the binding properties of the ligand of the present invention to the receptor of the present invention, a receptor preparation is prepared by suspending cells containing the receptor of the present invention or a membrane fraction of the cells in a buffer appropriate for use in the screening method. Any buffer can be used so long as it does not interfere the ligand-receptor binding, including a phosphate buffer or a Tris-HCl buffer, having pH of 4 to 10 (preferably pH of 6 to 8), etc. For the purpose of minimizing non-specific binding, a surfactant such as CHAPS, Tween-80™ (Kao-Atlas Inc.), digitonin, deoxycholate, etc., may optionally be added to the buffer. Further for the purpose of suppressing the degradation of the receptor of the present invention with a protease, a protease inhibitor such as PMSF, leupeptin, E-64 (manufactured by Peptide Institute, Inc.), pepstatin, etc. may also be added. A given amount (5,000 cpm to 500,000 cpm) of the labeled ligand of the present invention is added to 0.01 ml to 10 ml of the receptor solution, in which $10^{-10}$ M to $10^{-7}$ M of a test compound is co-present. To determine the amount of non-specific binding (NSB), a reaction tube charged with an unlabeled form of the ligand of the present invention in a large excess is also provided. The reaction is carried out at approximately 0° C. to 50° C., preferably 4° C. to 37° C. for 20 minutes to 24 hours, preferably 30 minutes to 3 hours. After completion of the reaction, the reaction mixture is filtrated through glass fiber filter paper, etc. and washed with an appropriate volume of the same buffer. The residual radioactivity on the glass fiber filter paper is then measured by means of a liquid scintillation counter or γ-counter. When nonspecific binding (NSB) is subtracted from the count ($B_0$) where any antagonizing substance is absent and the resulting count ($B_0$-NSB) is made 100%, the test compound showing the specific binding amount (B-NSB) of, e.g., 50% or less may be selected as a candidate compound.

In addition, the compounds that bind to the receptor of the present invention can also be screened utilizing the surface plasmon sensor technology,.

Specifically, the receptor of the present invention is immobilized on the sensor chip surface of Biacore 3000 (Biacore) and the solution of a test compound in phosphate buffered saline (PBS), etc. is poured onto the chip surface. Changes on the surface plasmon are measured so that the test compound bound to the receptor of the present invention is screened. For example, the test compound showing the measurement data of 5 resonance units or more in changes at the surface plasmon is screened as a substance having the binding properties to the receptor of the present invention.

The screening methods of the cell stimulating assay system described above can be performed by assaying the cell stimulating activities mediated by the receptor of the present invention (e.g., the activities of promoting or suppressing arachidonic acid release, acetylcholine release, intracellular Ca$^{2+}$ release, intracellular cAMP production, intracellular cGMP production, inositol phosphate production, change in cell membrane potential, phosphorylation of intracellular proteins, activation of c-fos, pH reduction, GTPγS binding activity, activation of cAMP-dependent protein kinase, activation of cGMP-dependent protein kinase, activation of phospholipid-dependent protein kinase, activation of microtubule-associated protein kinase (MAP kinase), etc.) by publicly known methods, or using assay kits commercially available. Specifically, the cells containing the receptor of the present invention are first cultured on a multiwell plate, etc. Prior to screening, the medium is replaced with fresh medium or with an appropriate non-cytotoxic buffer, followed by incubation for a given period of time in the presence of a test compound, etc. Subsequently, the cells are extracted or the supernatant is recovered and the resulting product is quantified by appropriate procedures. Where it is difficult to detect the production of the cell-stimulating activity indicator (e.g., arachidonic acid, etc.) due to degradation enzyme contained in the cells, an inhibitor against such degradation enzyme may be added prior to the assay. For detecting the activity such as the cAMP production suppression, the baseline production in the cells is increased by forskolin or the like and the suppressing effect on the increased baseline production can be detected.

For screening through the assay of the cell stimulating activities, appropriate cells, in which the receptor of the present invention is expressed, are required. The cells, in which the receptor of the present invention is expressed, are desirably the aforesaid cell line in which the receptor of the present invention is expressed, etc.

Examples of the test compounds include peptides, proteins, non-peptide compounds, synthetic compounds, fermentation products, cell extracts, plant extracts, animal tissue extracts, etc.

The screening methods of the cell stimulating assay system described above are described in (1) through (12) below, more specifically.

(1) When the receptor-expressed cell is stimulated by the receptor agonist, G protein in the cell is activated and GP binds thereto. This phenomenon is observed as well in a membrane fraction of the receptor-expressed cell. Usually, GTP is hydrolyzed to change to GDP; when GTPγS is previously added in the reaction solution, GTPγS binds to G protein as GTP does, but does not undergo hydrolysis so that the state of GTP bound to the G protein-containing cell membrane is maintained. When labeled GTPγS is used, the cell stimulating activities of the receptor agonist-expressed cell can be assayed by determining GTPγS remained on the cell membrane.

Utilizing this reaction, the stimulating activities of the ligand of the present invention on the receptor of the present invention-expressed cell can-be assayed, and the compound that changes the binding properties of the ligand of the present invention to the receptor of the present invention can be screened.

This method is carried out using the membrane fraction containing the receptor of the present invention. In the assay method, the substance showing the activity of promoting GTPγS binding onto the membrane fraction of the receptor of the present invention is an agonist.

Specifically, the compound that changes the binding properties of the ligand of the present invention to the receptor of the present invention is screened by assaying the GTPγS binding-promoting activities on the cell membrane fraction of the receptor of the present invention in the presence of labeled GTPγS, when the ligand of the present invention is brought in contact with the cell membrane fraction of the receptor of the present invention and when the ligand of the present invention and a test compound are brought in contact with the cell membrane fraction of the receptor of the present invention, and comparing the activities.

According to this method, a test compound showing the activity of suppressing the GTPγS binding-promoting activities on the cell membrane fraction of the receptor of the present invention by the ligand of the present invention can be selected as a candidate substance capable of competitive inhibition.

On the other hand, when a test compound alone is brought into contact with the cell membrane fraction of the receptor of the present invention, the agonist can be screened as well by assaying the GTPγS binding-promoting activities in the cell membrane fraction of the receptor of the present invention.

A specific example of the screening method is described below.

The cell membrane fraction containing the receptor of the present invention, prepared according to a publicly known method, is diluted in membrane dilution buffer (50 mM Tris, 5 mM MgCl$_2$, 150 mM NaCl, 1μM GDP, 0.1% BSA; pH 7.4). The dilution ratio varies depending on expression level of the receptor. After an aliquot of 0.2 ml is dispensed in Falcon 2053, the ligand of the present invention or the ligand of the present invention and a test compound is/are added thereto and [$^{35}$S] GTPγS is further added thereto in a final concentration of 200 pM. After keeping warm at 25° C. for an hour, 1.5 ml of ice-chilled wash buffer (50 mM Tris,5 mM MgCl$_2$, 150 mM NaCl, 0.1% BSA,0.05% CHAPS; pH 7.4) is added to the mixture followed by filtering glass filter paper GF/F. After keeping warm at 65° C. for 30 minutes and drying, the radioactivity of [$^{35}$S] GTPγS bound to the membrane fraction and remained on the filter paper is counted with a liquid scintillation counter. The radioactivity at the experimental site added only with the ligand of the present invention is made 100% and the radioactivity at the experimental site not added with the ligand of the present invention is made 0%, to calculate an effect of the test compound on the GTPγS binding promoting activity by the ligand of the present invention. When the GTPγS binding promoting activity becomes, e.g., 50% or less, the test compound can be selected as a candidate substance capable of competitive inhibition.

(2) In the cell where the receptor of the present invention, intracellular cAMP product is inhibited by stimulation of the ligand of the present invention. Utilizing this reaction, the stimulating activities of the ligand of the present invention on the cell where the receptor of the present invention is expressed are assayed so that the compound capable of changing the binding properties of the ligand of the present invention to the receptor of the present invention can be screened.

Specifically, the compound that changes the binding properties of the ligand of the present invention to the receptor of the present invention is screened by assaying the intracellular cAMP production inhibitory activities on the cell, in the presence of a substance for increasing the intracellular cAMP level, when the ligand of the present invention is brought in contact with a cell wherein the receptor of the present invention is expressed and when the ligand of the present invention and a test compound are brought in contact with the cell wherein the receptor of the present invention is expressed, and comparing the activities.

As the substance which increases the intracellular cAMP level, there are used, e.g., forskolin, calcitonin, etc.

The cAMP production level in the cell where the receptor of the present invention is expressed can be measured by the RIA system using anti-cAMP antibody obtained by immunization of mouse, rat, rabbit, goat, bovine, etc. and [$^{125}$I]-labeled cAMP (both commercially available), or the EIA system using anti-cAMP antibody in combination with labeled cAMP. Furthermore, quantification by SPA (Scintillation Proximity Assay) using beads containing an anti-cAMP antibody-immobilized scintillant using protein A or the antibody to IgG of the animal used for anti-cAMP antibody production, etc., and [$^{125}$I]-labeled cAMP is also possible (the kit available from Amersham Pharmacia Biotech, Inc. is used).

In this method, a test compound showing the activity of inhibiting the cAMP production inhibitory activity by the ligand of the present invention in the cells where the receptor of the present invention is expressed can be selected as a candidate substance capable of competitive inhibition.

On the other hand, when a test compound alone is brought into contact with the cells where the receptor of the present invention is expressed, a compound showing an agonist activity can be screened by inspecting the cAMP production inhibitory activity.

A specific example of the screening method is described below.

Cells (e.g., animal cells such as CHO cells, etc.) where the receptor of the present invention is expressed is plated in a 24-well plate in $5 \times 10^4$ cells/well, followed by incubation for 48 hours. The cells are washed with Hanks' buffer (pH 7.4) containing 0.2 mM 3-isobutylmethylxanthine, 0.05% BSA and 20 mM HEPES (hereinafter simply referred to as the reaction buffer). Subsequently, 0.5 ml of the reaction buffer is added to the cells, which is kept warm in an incubator for 30 minutes. After the reaction buffer is removed and 0.25 ml of fresh reaction buffer is added to the cells, 0.25 ml of the reaction buffer containing 2 μM forskolin, added with 1 μM of the ligand of the present invention or 1 μM of the ligand of the present invention and a test compound is added to the cell, followed by reacting at 37° C. for 24 minutes. By adding 100 μl of 20% perchloric acid, the reaction is terminated. Then, the mixture is allowed to stand on ice for an hour to extract intracellular cAMP. The cAMP level in the extract is measured using cAMP EIA Kit (Amersham Pharmacia Biotech, Inc.). The cAMP level produced by forskolin stimulation is made 100% and the cAMP level inhibited by the addition of 1 μM of the ligand of the present invention is made 0%, and the effect of the test compound on the cAMP production inhibitory activity by the ligand of the present invention is calculated. A test compound, which inhibits the activity of the ligand of the present invention to show the cAMP production activity of, e.g., 50% or more can be selected as a candidate substance capable of competitive inhibition.

Also when the cell where the receptor of the present invention is expressed and which shows the property of increasing intracellular cAMP level by stimulation of the receptor of the present invention is used, the compound that changes the binding properties of the ligand of the present invention to the receptor of the present invention can be screened by assaying the intracellular cAMP production promoting activities on the cell, when the ligand of the present invention is brought in contact with a cell wherein the receptor of the present invention is expressed and when the ligand of the present invention and a test compound are brought in contact with the cell wherein the receptor of the present invention is expressed, and comparing the activities.

In this method, a test compound showing the activity of inhibiting the cAMP production promoting activity by the ligand of the present invention in the cell where the receptor of the present invention is expressed can be selected as a candidate substance capable of competitive inhibition.

On the other hand, when a test compound alone is brought into contact with the cell where the receptor of the present invention is expressed, a compound showing an agonist activity can be screened by inspecting the cAMP producing activity.

The cAMP production producing activity is assayed by the method described above, through quantification of cAMP produced by adding the ligand of the present invention or the ligand of the present invention and a test compound to the cell where the receptor of the present invention is expressed, without adding forskolin in the screening method described above.

(3) The compound that changes the binding properties of the ligand of the present invention to the receptor of the present invention can be screened by assaying the stimulating activity of the ligand of the present invention on the cell where the receptor of the present invention is expressed, using a CRE-reporter gene vector.

A DNA containing CRE (cAMP response element) is inserted into a reporter gene of the vector at the upstream to acquire the CRE-reporter gene vector. In the cell where the CRE-reporter gene vector-transfected receptor of the present invention is expressed, stimulation accompanied by increased cAMP induces expression of the reporter gene medicated by CRE and subsequent production of the gene product (protein) by the reporter gene. That is, changes of the cAMP level in the CRE-reporter gene vector-transfected cell can be detected by assaying the enzyme activity of the reporter gene protein.

Specifically, the compound that changes the binding properties of the ligand of the present invention to the receptor of the present invention is screened by assaying the enzyme activities of the reporter gene protein in the presence of a substance for increasing the intracellular cAMP level, when the ligand of the present invention is brought in contact with a cell wherein the CRE-reporter gene vector-transfected receptor of the present invention is expressed and when the ligand of the present invention and a test compound are brought in contact with the cell wherein the receptor of the present invention with a CRE-reporter gene vector transfected is expressed, and comparing the activities As the substance which increases the intracellular cAMP level, there are used, e.g., forskolin, calcitonin, etc.

As the vector, for example, PicaGene Basic Vector, PicaGene Enhancer Vector (Toyo Ink Mfg. Co., Ltd.), etc. are employed. A CRE-containing DNA is inserted into a multicloning site at the upstream of reporter gene of the vector described above, e.g., a luciferase gene, which is made the CRE-reporter gene vector.

In this method, a test compound which recovers the enzyme activity suppression of the reporter gene protein by the ligand of the present invention can be selected as a candidate substance capable of competitive inhibition.

On the other hand, the agonist can be screened as well by contacting a test compound alone with the cell where the receptor of the present invention is expressed and assaying the suppression of luminescence level increased by forskolin stimulation as in the ligand of the present invention.

A specific example of this screening method is described below, in which luciferase is utilized as the reporter gene.

The cells where the CRE-reporter gene (luciferase)-transfected receptor of the present invention is expressed are plated on a 24-well plate in $5 \times 10^3$ cells/well, followed by cultivation for 48 hours. The cells are washed with Hanks' buffer (pH 7.4) containing 0.2 mM 3-isobutyl-methylxanthine, 0.05% BSA and 20 mM HEPES (hereinafter merely referred to as the reaction buffer). Subsequently, 0.5 ml of the reaction buffer is added to the cells, which is kept warm in an incubator for 30 minutes. After the reaction buffer is removed and 0.25 ml of fresh reaction buffer is added to the cells, 0.25 ml of the reaction buffer containing 2 µM forskolin, added with 1 µM of the ligand of the present invention or 1 µM of the ligand of the present invention and a test compound is added to the cells, followed by reacting at 37° C. for 24 minutes. The cells are dissolved in a cell lysis agent for PicaGene (Toyo Ink Mfg. Co., Ltd.) and a luminescence substrate (Toyo Ink Mfg. Co., Ltd.) is added to the lysate. The luminescence by luciferase is measured with a luminometer, a liquid scintillation counter or a top counter. The luminescence level by luciferase is measured when the ligand of the present invention is added solely and when 1 µM of the ligand of the present invention and a test compound are added, and comparison is made.

The ligand of the present invention suppresses the increase in luminescent level by luciferase, based on forskolin stimulation. The compound that recovers the suppression can be selected as a candidate substance capable of competitive inhibition.

As the reporter gene, for example, genes of alkaline phosphatase, chloramphenicol acetyltransferase, β-galactosidase, etc. may be employed. The enzyme activities of these reporter gene proteins are assayed by publicly known methods, or using assay kits commercially available. The alkaline phosphatase activity can be assayed using, e.g., Lumi-Phos 530 manufactured by Wako Pure Chemical Industries Co., Ltd.; the chloramphenicol acetyltransferase activity using, e.g.: FAST CAT chloramphenicol Acetyltransferase Assay Kit manufactured by Wako Pure Chemical Industries Co., Ltd.; and the β-galactosidase activity using, e.g., Aurora Gal-XE manufactured by Wako Pure Chemical Industries Co., Ltd.

(4) The cell where the receptor of the present invention is expressed releases arachidonic acid metabolite at the outside of the cell by stimulation of the ligand of the present invention. Utilizing this reaction, the stimulating activities of the ligand of the present invention on the cell where the receptor of the present invention is expressed are assayed, whereby the compound that changes the binding properties of the ligand of the present invention to the receptor of the present invention can be screened.

Labeled arachidonic acid is previously taken up into the cell where the receptor of the present invention is expressed. Thus, the arachidonic acid metabolite releasing activity can be assayed by measuring the labeled arachidonic acid metabolite released at the outside of the cell.

Specifically, the compound that changes the binding properties of the ligand of the present invention to the receptor of the present invention is screened by assaying the arachidonic acid metabolite-releasing activities, when the ligand of the present invention is brought in contact with the cell where the receptor of the present invention containing labeled arachidonic acid is expressed and when the ligand of the present invention and a test compound are brought in contact with the cell where the receptor of the present invention containing labeled arachidonic acid is expressed, and comparing the activities In this method, a test compound which inhibits the arachidonic acid metabolite-releasing enzyme activity by the ligand of the present invention can be selected as a candidate substance capable of competitive inhibition.

Also, a test compound alone is brought into contact with the cell where the receptor of the present invention is expressed and the arachidonic acid metabolite-releasing activity in the cell where the receptor of the present invention is expressed is examined by publicly known methods. Thus, the compound showing the agonist activity can be screened as well.

A specific example of the screening method is described below.

The cells where the receptor of the present invention is expressed are plated on a 24-well plate in $5 \times 10^4$ cells/well. After incubation for 24 hours, [$^3$H] arachidonic acid is added to the cells in 0.25 µCi/well and 16 hours after, the cells are washed with Hanks' buffer (pH 7.4) containing 0.05%. BSA and 20 mM HEPES (hereinafter merely referred to as the reaction buffer). Subsequently, 500 µl of the reaction buffer containing the ligand of the present invention in a final concentration of 10 µM or the ligand of the present invention in a final concentration of 10 µM and a test compound is added to each well. After incubating at 37° C. for 60 minutes, 400 µl of the reaction solution is added to a scintillator and the amount of [$^3$H] arachidonic acid metabolite released into the reaction solution is determined by a scintillation counter.

The amount of free [$^3$H] arachidonic acid metabolite released when 500 µl of the reaction buffer alone is added (neither the ligand of the present invention nor the test compound is added) is made 0%, and the amount of free [$^3$H] arachidonic acid metabolite released when the reaction buffer containing 10 µM of the ligand of the present invention is added (no test compound is added) is made 100%; the amount of free [$^3$H] arachidonic acid metabolite released when a test compound is added is calculated.

When the arachidonic acid metabolite-releasing activity becomes, e.g., 50% or less, the test compound can be selected as a candidate substance capable of competitive inhibition.

(5) In the cells where the receptor of the present invention is expressed, intracellular Ca level increases by stimulation of the ligand of the present invention. Utilizing this reaction, the stimulating activities of the ligand of the present invention on the cells where the receptor of the present invention is expressed are assayed, whereby the compound that changes the binding properties of the ligand of the present invention to the receptor of the present invention can be screened.

Specifically, the compound that changes the binding properties of the ligand of the present invention to the receptor of the present invention is screened by assaying the intracellular calcium level increasing activities, when the ligand of the present invention is brought, in contact with the cell where the receptor of the present invention is expressed and when the ligand of the present invention and a test compound are brought in contact with the cell where the receptor of the present invention is expressed, and comparing the activities. The assay is carried out by publicly known methods.

In this method, a test compound which suppresses an increase of the intracellular calcium level increasing activity by the ligand of the present invention can be selected as a candidate substance capable of competitive inhibition.

On the other hand, the agonist can be screened as well by measuring an increase of fluorescence intensity by the addition of a test compound alone.

A specific example of the screening method is described below.

The cells where the receptor of the present invention is expressed are inoculated on a sterilized cover glass for microscopy. vTwo days after, the culture medium is replaced by HBSS in which 4 mM Fura-2 AM (Dojin Kagaku Kenkyusho) is suspended, and the mixture is allowed to stand at room temperature for 2 hours and 30 minutes. After washing with HBSS, the cover glass is set on a cuvette, and an increased ratio of fluorescence intensity at 505 nm is measured with a fluorescence spectrophotometer at excited wavelengths of 340 nm and 380 nm, when the ligand of the present invention or the ligand of the present invention and a test compound is/are added.

Also, FLIPR (manufactured by Molecular Device Co.) may be used as described below. Fluo-3 AM (manufactured by Dojin Kagaku Kenkyusho) is added to a suspension of the cells where the receptor of the present invention is expressed, thereby to incorporate Fluo-3 AM into the cells. The supernatant is washed several times through centrifugation and the cells are inoculated on a 96-well plate. After setting on the FLIPR device, the ligand of the present invention or the ligand of the present invention and a test compound is/are added as in Fura-2, and comparison is made.

Furthermore, the compound that changes the binding properties of the ligand of the present invention to the receptor of the present invention can also be screened by co-expressing a gene (e.g., aequorin, etc.) for the protein that emits light in response to increased Ca ions in the cell where the receptor of the present invention is expressed and utilizing the luminescence emitted by conformational switch of the gene protein (e.g., aequorin,. etc.) to the Ca-bound protein.

The cells where the receptor of the present invention is co-expressed together with a gene for protein emitting light in response to an increase of intracellular Ca ions are plated on a 96-well plate, and the ligand of the present invention or the ligand of the present invention and a test compound is/are added thereto, as described above. Thus, an increase in the ratio of fluorescence intensity is measured using a fluorometer; followed by comparison.

The test compound that inhibits the increase in the ratio of fluorescence intensity by the ligand of the present invention can be selected as a candidate substance capable of competitive inhibition.

(6) When a receptor agonist is added to a receptor-expressed cell, the intracellular inositol triphosphate level increases. By utilizing the intracellular inositol triphosphate producing activity of the ligand of the present invention in the cell where the receptor of the present invention is expressed, the compound that changes the binding properties of the ligand of the present invention to the receptor of the present invention can be screened.

Specifically, the compound that changes the binding properties of the ligand of the present invention to the receptor of the present invention can be screened by assaying the inositol triphosphate producing activities in the presence of labeled inositol, when the ligand of the present invention is brought in contact with the cell wherein the receptor of the present invention is expressed and when the ligand of the present invention and a test compound are brought in contact with the cell wherein the receptor of the present invention is expressed, and comparing the activities. The assay is carried out by publicly known methods.

In this method, a test compound which suppresses the inositol triphosphate producing activity can be selected as a candidate substance capable of competitive inhibition.

On the other hand, the agonist can be screened as well by contacting a test compound alone with the cell where the receptor of the present invention is expressed and measuring an increase in the inositol triphosphate production.

A specific example of the screening method is described below.

The cells where the receptor of the present invention is expressed are plated on a 24-well plate followed by incubation for a day. Then, myo-[2-$^3$H] inositol (2.5 μCi/well) is added to each well. In this medium the cells are incubated for a day and thoroughly washed in a medium free of radioactive inositol. After the ligand of the present invention or the ligand of the present invention and a test compound is/are added, the reaction is terminated by adding 10% perchloric acid. The reaction mixture is neutralized with 1.5 M potassium hydroxide and 60 mM HEPES solution and then passed through a column packed with 0.5 ml of AG1×8 resin (Bio-Rad). After washing with 5 mM sodium tetraborate. ($Na_2BO_3$) and 60 mM ammonium formate ($HCOONH_4$), the radioactivity eluted with 1M ammonium formate and 0.1M formic acid is measured with a liquid scintillation counter. When the radioactivity without adding the ligand of the present invention is made 0% and the radioactivity added with the ligand of the present invention is made 100%, an effect of the test compound on the binding of the ligand of the present invention to the receptor of the present invention is calculated.

A test compound which reduces the inositol triphosphate production activity to, e.g., 50% or less, can be selected as a candidate substance capable of competitive inhibition.

(7) The compound that changes the binding properties of the ligand of the present invention to the receptor of the present invention can be screened by assaying the stimulating activity of the ligand of the present invention on the cell where the receptor of the present invention is expressed, using a TRE-reporter gene vector.

A DNA containing TRE (TPA response element) is inserted into a reporter gene of the vector at the upstream to acquire the TRE-reporter gene vector. In the cell where the TRE-reporter gene vector-transfected receptor of the present invention is expressed, stimulation accompanied by increased intracellular calcium level induces expression of the reporter gene medicated by TRE and subsequent production of the gene product (protein) by the reporter gene. That is, changes of the calcium level in the TRE-reporter gene vector-transfected cell can be detected by assaying the enzyme activity of the reporter gene protein.

Specifically, the compound that changes the binding properties of the ligand of the present invention to the receptor of the present invention is screened by assaying the enzyme activities of the reporter gene protein, when the ligand of the present invention is brought in contact with a cell wherein the TRE-reporter gene vector-transfected receptor of the present invention is expressed and when the ligand of the present invention and a test compound are brought in contact with the cell wherein the receptor of the present invention with a TRE-reporter gene vector transfected is expressed, and comparing the activities As the vector, for example, PicaGene Basic Vector, PicaGene Enhancer Vector (Toyo Ink Mfg. Co., Ltd.), etc. are employed. A TRE-containing DNA is inserted into a multicloning site at the upstream of reporter gene of the vector described above, e.g., a luciferase gene, which is made the TRE-reporter gene vector.

In this method, a test compound which suppresses the enzyme activity of the reporter gene protein by the ligand of the present invention can be selected as a candidate substance capable of competitive inhibition.

On the other hand, the agonist can be screened as well by contacting a test compound alone with the cell where the receptor of the present invention is expressed and assaying the increased luminescence level as in the ligand of the present invention.

A specific example of this screening method is described below, in which luciferase is utilized as the reporter gene.

The cells where the TRE-reporter gene (luciferase)-transfected receptor of the present invention is expressed are plated on a 24-well plate in $5 \times 10^3$, cells/well followed by incubation for 48 hours. After the cells are washed with Hanks' buffer (pH 7.4) containing 0.05% BSA and 20 mM HEPES, 10 nM of the ligand of the present invention or 10 nM of the ligand of the present invention and a test compound is/are added to the cells, followed by reacting at 37° C. for 60 minutes. The cells are dissolved in a cell lysis agent for PicaGene (Toyo Ink Mfg. Co., Ltd.) and a luminescence substrate (Toyo Ink Mfg. Co., Ltd.) is added to the lysate. The luminescence by luciferase is measured with a luminometer, a liquid scintillation counter or a top counter. The amount of luminescence by luciferase is measured when the ligand of the present invention is added solely and when 10 nM of the ligand of the present invention and a test compound is/are added, and comparison is made.

In response to the increased intracellular calcium, the amount of luminescence by luciferase increases. The compound that suppresses the increase can be selected as a candidate substance capable of competitive inhibition.

As the reporter gene, for example, genes of alkaline phosphatase, chloramphenicol acetyltransferase, β-galactosidase, etc. may be employed. The enzyme activities of these reporter gene proteins are assayed by publicly known methods, or using assay kits commercially available. The alkaline phosphatase activity can be assayed using, e.g., Lumi-Phos 530 manufactured by Wako Pure Chemical Industries Co., Ltd.; the chloramphenicol-acetyltransferase activity using, e.g., FAST CAT chloramphenicol Acetyltransferase Assay Kit manufactured by Wako Pure Chemical Industries Co., Ltd.; and the β-galactosidase activity using, e.g., Aurora Gal-XE manufactured by Wako Pure Chemical Industries Co., Ltd.

(8) In the cell where the ligand of the present invention is expressed, MAP kinase is activated by stimulation of the ligand of the present invention. Utilizing the reaction, the compound that changes the binding properties of the ligand of the present invention to the receptor of the present invention can be screened by assaying the stimulation activities of the ligand of the present invention on the cell where the receptor of the present invention is expressed.

Specifically, the compound that changes the binding properties of the ligand of the present invention to the receptor of the present invention can be screened by assaying the cell growth, when the ligand of the present invention is brought in contact with a cell wherein the receptor of the present invention is expressed and when the ligand of the present invention and a test compound are brought in contact with the cell wherein the receptor of the present invention is expressed, and comparing the cell growth.

The growth of the cell where the receptor of the present invention is expressed is determined by measuring, e.g., the MAP kinase activity, the thymidine uptake activity, the cell count, etc.

In a specific example, the MAP kinase activity is assayed as follows. The ligand of the present invention or the ligand of the present invention and a test compound is/are added to the cell where the receptor of the present invention is expressed; immunoprecipitation is carried out using an anti-MAP kinase antibody to obtain a MAP kinase fraction from a cell lysate; then using, e.g., MAP Kinase Assay Kit manufactured by Wako Pure Chemical Industries Co., Ltd. and $\gamma$-[$^{32}$P]-ATP, the MAP kinase activity is assayed; and comparison is made.

The thymidine uptake activity can be assayed by plating on a 24-well plate the cell where the ligand of the present invention is expressed, followed by incubation. After the ligand of the present invention or the ligand of the present invention and a test compound is/are added to the cells, radioactively labeled thymidine (e.g., [methyl-$^3$H]-thymidine, etc.) is added thereto. Then the cells are lysed and by counting the radioactivity of the labeled thymidine taken up into the cells with a liquid scintillation counter, the thymidine uptake activity is assayed and comparison is made.

To determine the cell count, the cells where the ligand of the present invention is expressed are plated on a 24-well plate. After the ligand of the present invention or the ligand of the present invention and a test compound is/are added to the cells, MTT (3-(4,5-dimethyl-2-thiazolyl)-2,5-diphenyl-2H-tetrazolium bromide) is added thereto. MTT taken up into the cells changes to MTT formazan, which absorption is measured at 570 nm, after cell lysis with isopropanol rendered acidic with hydrochloric acid. Then, comparison is made.

In this method, a test compound which suppresses the growth of the cell where the receptor of the present invention is expressed can be selected as a candidate substance capable of competitive inhibition.

On the other hand, the agonist can also be screened by contacting a test compound alone with the cell where the receptor of the present invention is expressed and measuring the cell growth activity as in the ligand of the present invention.

A specific example of the screening method utilizing the thymidine uptake activity is described below.

The cells where the ligand of the present invention is expressed are plated on a 24-well plate in 5000 cells/well followed by incubation for one day. Next, the cells are incubated in a serum-free medium for 2 days to bring the cells under starvation. The ligand of the present invention or the ligand of the present invention and a test compound is/are added to the cells. After incubation for 24 hours, [methyl-$^3$H] thymidine is added in 0.015 MBq/well followed by incubation for 6 hours. After washing the cells with PBS, methanol is added to the cells. The mixture is allowed to stand for 10 minutes. Next, 5% trichloroacetic acid is added and the mixture is allowed to stand for 15 minutes. The immobilized cells are washed 4 times with distilled water. After cell lysis with 0.3 N sodium hydroxide solution, the radioactivity in the lysate is measured with a liquid scintillation counter.

The compound that suppresses the increase in the radioactivity by the addition of the ligand of the present invention can be selected as a candidate substance capable of competitive inhibition.

(9) In the cell where the ligand of the present invention is expressed, the potassium channel is activated by stimulation of the ligand of the present invention so that K ions present within the cells are effluxed outside of the cells. Utilizing the reaction, the compound that changes the binding properties of the ligand of the present invention to the receptor of the present invention can be screened by assaying the stimulating activities of the ligand of the present invention on the cell where the receptor of the present invention is expressed.

Rb ions (rubidium ions) in the related elements to K ions flow out of the cells through the potassium channel without being discriminated from K ions. Thus, radioactive isotope Rb ([$^{86}$Rb]) is added to the cells to permit intracellular uptake of the isotope. Then, the efflux of $^{86}$Rb that flows out by stimulation of the ligand of the present invention is measured to assay the stimulating activities of the ligand of the present invention on the cells where the receptor of the present invention is expressed.

Specifically, the compound that changes the binding properties of the ligand of the present invention to the receptor of the present invention can be screened by assaying the efflux activities of $^{86}$Rb in the presence of $^{86}$Rb, when the ligand of the present invention is brought in contact with the cell wherein the receptor of the present invention is expressed and when the ligand of the present invention and a test compound are brought in contact with the cell wherein the receptor of the present invention is expressed, and comparing the cell activities.

In this method, a test compound which suppresses an increase of the efflux activity of $^{86}$Rb by stimulation of the ligand of the present invention can be selected as a candidate substance capable of competitive inhibition.

On the other hand, the agonist can be screened as well by contacting a test compound alone with the cell where the receptor of the present invention is expressed and measuring the increase in the efflux activity of $^{86}$Rb.

A specific example of the screening method is described below.

The cells where the ligand of the present invention are plated on a 24-well plate followed by incubation for 2 days. The cells are then kept warm for 2 hours in a medium containing 1 mCi/ml of $^{86}$RbCl. The medium is thoroughly washed to completely remove $^{86}$RbCl in the outer liquid. The ligand of the present invention or the ligand of the present invention and a test compound is/are added to the cells. The outer liquid is recovered 30 minutes later and the radioactivity is counted with a γ counter, and comparison is made.

The test compound which suppresses the increase in the efflux activity of $^{86}$Rb by stimulation of the ligand of the present invention can be selected as a candidate substance capable of competitive inhibition.

(10) The cell where the ligand of the present invention is expressed reacts with the ligand of the present invention so that the extracellular pH changes. Utilizing this reaction, the compound that changes the binding properties of the ligand of the present invention to the receptor of the present invention can be screened by assaying the stimulating activities of the ligand of the present invention on the cell where the receptor of the present invention is expressed.

Specifically, the compound that changes the binding properties of the ligand of the present invention to the receptor of the present invention is screened by measuring the extracellular pH changes, when the ligand of the present invention is brought in contact with the cell wherein the receptor of the present invention is expressed and when the ligand of the present invention and a test compound are brought in contact with the cell wherein the receptor of the present invention is expressed, and comparing the changes.

The extracellular pH change is measured using, e.g., a Cytosensor device (Molecular Device Co.).

In this method, a test compound which suppresses the extracellular pH change by the ligand of the present invention can be selected as a candidate substance capable of competitive inhibition.

On the other hand, the agonist can be screened as well by contacting a test compound alone with the cell where the receptor of the present invention is expressed and measuring the extracellular pH change, as in the ligand of the present invention.

A specific example of the screening method is described below.

The cells where the receptor of the present invention is expressed are incubated overnight in a capsule for the Cytosensor device, which is set in a chamber of the device to reflux 0.1% BSA-containing RPMI 1640 medium (manufactured by Molecular Device Co.) until the extracellular pH becomes stable. After the pH becomes stable, a medium containing the ligand of the present invention or the ligand of the present invention and a test compound is refluxed on the cells. The pH change in the medium caused by the reflux is measured, and comparison is made.

The test compound which suppresses the extracellular pH change by the ligand of the present invention can be selected as a candidate substance capable of competitive inhibition.

(11) In yeast (*Saccharomyces Cerevisiae*), the sex pheromone receptor STe2 of haploid α-mating type (MATα) is coupled to G protein Gpa1 and activates MAP kinase in response to the sex pheromone α-mating factor, whereby Far1 (cell-cycle arrest) and the transcription activator Ste12 are activated. Ste12 induces expression of various proteins (e.g., FUS1 which takes part in mating). On the other hand, the regulatory factor Sst2 functions to inhibit the foregoing process. In this system, an attempt has been made by preparing the receptor gene-transfected yeast, stimulating by the receptor agonist to activate the signal transduction system in the yeast cells, and using the growth, etc. resulting therefrom as an indicator (Trends in Biotechnology, 15, 487–494, 1997). Utilizing the receptor gene-transfected yeast system, the compound that changes the binding properties of the ligand of the present invention to the receptor of the present invention can be screened.

A specific example is shown below.

Ste2 in MATα yeast and the gene encoding Gpa1 are removed and instead, a gene for the receptor of the present invention and a gene encoding the Gpa1-Gai2 fused protein are introduced. The gene encoding Far is removed to cause no cell-cycle arrest and the gene encoding Sst is removed to increase the sensitivity in response to the ligand of the present invention. Furthermore, FUS1-HIS3 gene, which is FUS1 ligated with histidine biosynthesis gene HIS3, is introduced. The foregoing genetic recombinant engineering can be performed by the method described in, e.g., Molecular and Cellular Biology, 15, 6188–6195, 1995), using the receptor of the present invention in place of somatostatin receptor type 2 (SSTR2) gene.

The thus constructed transformant yeast is responsive to the ligand of the present invention in a high sensitivity so that MAP kinase is activated and a histidine biosynthesis enzyme is synthesized. Thus, the transformant becomes capable of growing in a histidine-deficient medium.

Accordingly, the compound that changes the binding properties of the ligand of the present invention to the receptor of the present invention can be screened by incubating the yeast described above where the receptor of the present invention is expressed (MATα yeast in which the Ste2 gene and the Gpa1 gene are removed, the receptor gene of the present invention and the gene encoding the Gpa1-Gai2 fused protein are introduced, the Far gene and the Sst gene are removed, and the FUS1-HIS3 gene is introduced) in a histidine-deficient medium, contacting the ligand of the present invention or the ligand of the present invention and a test compound with the yeast, measuring the growth of the yeast, and comparing the growth.

In this method, a test compound which suppresses growth of the yeast can be selected as a candidate substance capable of competitive inhibition.

On the other hand, the agonist can be screened as well by contacting a test compound alone with the yeast where the receptor of the present invention is expressed, and measuring growth of the yeast, as in the ligand of the present invention.

A specific example of the screening method is described below.

The yeast described above where the receptor of the present invention is expressed is incubated overnight in complete synthesis medium and added to a histidine-free soft agar medium in a concentration of $2 \times 10^4$ cells/ml. Then, the yeast is plated on a square Petri dish of 9×9 cm. After the agar is solidified, a sterilized filter paper impregnated with the ligand of the present invention or the ligand of the present invention and a test compound is put on the agar surface, followed by incubation at 30° C. for 3 days. An effect of the test compound is examined by comparing the growth of the yeast at the periphery of the filter paper with the case of using the sterilized filter paper impregnated with the ligand of the present invention alone. Alternatively, the assay can be made by previously adding the ligand of the present invention to a histidine-free agar medium, impregnating the sterilized, filter paper with a test compound alone to incubate the yeast and monitoring that growth of the yeast over the entire surface of the Petri dish is affected at the periphery of the filter paper.

The compound that suppresses the growth of the yeast can be selected as a candidate substance capable of competitive inhibition.

(12) When the receptor gene RNA of the present invention is injected into *Xenopus laevis* oocytes and stimulated by the ligand of the present invention, the intracellular calcium ion level increases to cause calcium-activated chloride current. This can be taken as fluctuation in membrane potential (same as in the case where fluctuation occurs in the potassium ion level gradient). Utilizing the above reaction in the *Xenopus laevis* oocytes induced by the ligand of the present invention, the compound that changes the binding properties of the ligand of the present invention to the receptor of the present invention can be screened by assaying the stimulating activities of the ligand of the present invention on the cell where the receptor of the present invention is expressed.

Specifically, the compound that changes the binding properties of the ligand of the present invention to the receptor of the present invention is screened by measuring the changes in cell membrane potential when the ligand of the present invention is brought in contact with the *Xenopus laevis* oocytes where RNA of a gene for the receptor of the present invention is transfected and when the ligand of the present invention and a test compound are brought in contact with the *Xenopus laevis* oocytes where RNA of a gene for the receptor of the present invention is transfected, and comparing the changes.

In this method, a test compound which suppresses the changes in cell membrane potential can be selected as a candidate substance capable of competitive inhibition.

On the other hand, the agonist can be screened as well by contacting a test compound alone with the *Xenopus laevis* oocytes where the receptor gene RNA of the present invention is transfected, and measuring the changes in cell membrane potential as in the ligand of the present invention.

A specific example of the screening method is described below.

A female individual of *Xenopus laevis* anesthetized by immersing in ice water is anatomized for taking out oocytes. The oocyte clusters are treated with collagenase (0.5 mg/ml) dissolved in an MBS solution (88 mM NaCl, 1 mM KCl, 0.41 mM $CaCl_2$, 0.33 mM $Ca(NO_3)_2$, 0.82 mM $MgSO_4$, 2.4 mM $NaHCO_3$, 10 mM HEPES; pH 7.4) at 19° C. for 1 to 6 hours at 150 rpm, until the oocytes are separated one from another. Washing is performed 3 times by replacing the MBS solution for the outer liquid followed by microinjection of cRNA (50 ng/50 nl) added with poly(A)$^+$ of the receptor of the present invention using a micromanipulator.

The receptor gene mRNA of the present invention may be prepared from tissues or cells, or transcribed from plasmids in vitro. The receptor gene mRNA of the present invention is incubated in the MBS solution at 20° C. for 3 days and placed in a hole of a voltage clamp device, which is continuously perfused with Ringer's solution, and impaled with a glass microelectrode for voltage clamp and a glass microelectrode for recording, in which (−) electrode is placed outside the oocytes. When the holding potential stabilizes, Ringer's solution containing the ligand of the present invention or the ligand of the present invention and a test compound is perfused to record changes in potential. An effect of the test compound can be measured by comparing the changes in cell membrane potential in the *Xenopus laevis* oocytes where the receptor gene RNA of the present invention is transfected with the case when the Ringer's solution containing the ligand of the present invention alone.

The compound that suppresses the changes in cell membrane potential can be selected as a candidate substance capable of competitive inhibition.

In the system described above, the changes in potential can be monitored more easily when the variations in potential increase. Therefore, polyA-added RNA of various G protein genes may be introduced. Also, the amount of luminescence, not the changes in membrane potential, can be measured by co-injecting polyA-added RNA of a gene for the protein (e.g., aequorin, etc.) that emits light in the presence of calcium.

The kit for screening the compound or its salt that changes the binding properties of the ligand of the present invention to the receptor of the present invention comprises the receptor of the present invention or the cell or its membrane fraction containing the receptor of the present invention, and the ligand of the present invention.

Examples of the screening kit of the present invention are given below:

1. Reagent for Screening (1) Assay Buffer and Wash Buffer

Hanks' Balanced Salt Solution (manufactured by Gibco Co.) supplemented with 0.05% bovine serum albumin (Sigma Co.).

The solution is sterilized by filtration through a 0.45 μm filter and stored at 4° C. Alternatively, the solution may be prepared at use.

(2) Preparation of the Receptor of the Present Invention

CHO cells where the receptor of the present invention is expressed are subcultured in a 12-well plate at the rate of $5 \times 10^5$ cells/well and then cultured at 37° C. under 5% $CO_2$ and 95% air for 2 days.

(3) Labeled Ligand

The ligand of the present invention labeled with commercially available [$^3$H], [$^{125}$I], [$^{14}$C], [$^{35}$S], etc. is dissolved in a suitable solvent or buffer. The solution is stored at 4° C. or −20° C., which is diluted to 1 µM with an assay buffer at use.

(4) Standard Ligand Solution

The ligand of the present invention is dissolved in PBS supplemented with 0.1% bovine serum albumin (manufactured by Sigma, Inc.) in a concentration of 1 mM, and the solution is stored at −20° C.

2. Assay Method (1) Cells are cultured in a 12-well tissue culture plate to express the receptor of the present invention. After washing the cells twice with 1 ml of the assay buffer, 490 µl of the assay buffer is added to each well.

(2) After 5 µl of a test compound solution of 10-3 to 10-10 M is added, 5 µl of a labeled form of the ligand of the present invention is added to the system followed by reacting at room temperature for an hour. To determine the amount of the non-specific binding, the ligand of the present invention of $10^{-3}$ M is added in an amount of 5 µl, instead of the test compound.

(3) The reaction mixture is removed and washed 3 times with 1 ml each of the wash buffer. The labeled polypeptide of the present invention bound to the cells is dissolved in 0.2N NaOH-1% SDS and mixed with 4 ml of a liquid scintillator A (manufactured by Wako Pure Chemical Industries, Ltd.).

(4) Radioactivity is measured using a liquid scintillation counter (manufactured by Beckmann) and PMB (percent of the maximum binding) is calculated in accordance with the following equation 1:

$$PMB = [(B-NSB)/(B_0-NSB)] \times 100$$

wherein:
PMB: percent of the maximum binding
B: value when a sample is added
NSB: non-specific binding
$B_0$: maximum binding The compound or its salt, which is obtainable by the screening method or the screening kit of the present invention, is the compound that changes the binding properties of the ligand of the present invention compound to the receptor of the present invention, or the compound that promotes or inhibits the activities of the receptor of the present invention. Specifically, these compounds include (i) the compounds or salts thereof that have the cell-stimulating activities mediated by the receptor of the present invention (the receptor agonists of the present invention), (ii) the compounds that do not have the cell-stimulating activities described above (the receptor antagonists of the present invention), (iii) the compounds that promote the binding of the receptor of the present invention to the ligand of the present invention, (iv) the compounds that inhibit the binding of the receptor of the present invention to the ligand of the present invention, and the like. Examples of these compounds include those selected from peptides, proteins, non-peptide compounds, synthetic compounds, fermentation products, cell extracts, plant extracts, animal tissue extracts, plasma, etc. These compounds may be novel or publicly known compounds.

The same salts given for the receptor of the present invention above apply to the salts of these compounds.

Evaluation of whether the compound is the receptor agonist or antagonist of the present invention described above is determined by, e.g., (i) or (ii) below.

(i) According to the screening methods (1) to (3) described above, the binding assay is carried out to obtain the compound that changes the binding properties of the ligand of the present invention to the receptor of the present invention (especially, the compound that inhibits the binding). It is then determined if the compound has the above cell-stimulating activities mediated by the receptor of the present invention. The compound or its salt that has the cell-stimulating activities is the receptor agonist of the present invention (agonist), whereas the compound having no such activities or its salt is the receptor antagonist of the present invention (antagonist).

(ii) (a) A test compound is brought in contact with a cell containing the receptor of the present invention, and the aforesaid cell-stimulating activities mediated by the receptor of the present invention are assayed. The compound or its salt that has the cell-stimulating activities is the receptor agonist of the present invention.

(b) The cell-stimulating activities mediated by the ligand of the present invention are assayed when the receptor of the present invention is brought in contact with the cell containing the receptor of the present invention and when the ligand of the present invention and a test compound are brought in contact with the cell containing the receptor of the present invention, and comparison is made. The compound or its salt that can reduce the cell-stimulating activities by the compound that activates the receptor of the present invention is the receptor antagonist of the present invention.

As stated above, the ligand of the present invention possesses the histamine release activity on rat mast cells stimulated by antigen or concanavalin A, the activity of releasing histamine by synergistically acting on rat mast cells together with nerve growth factor (NGF), the growth regulating activity on human T cells, the activity of potentiating the differentiation-inducing ability of NGF on PC12 cells, the blood coagulation inhibitory activity, the platelet agglutination response inhibitory activity, etc.

Thus, the receptor agonist of the present invention exhibits the actions similar to the physiological activities (e.g., the activity potentiating effect on the nerve growth factor, etc.) possessed by the ligand of the present invention, and are useful as safe and low-toxic pharmaceuticals such as agents for the prevention/treatment of, for example, nerve growth factor activity potentiators, neurodegenerative diseases (e.g., Alzheimer's diseases, Parkinson's disease, Down's syndrome, amyotrophic lateral sclerosis, prion disease, Creutzfeldt-Jakob disease, Huntington's chorea, diabetic neuropathy, multiple sclerosis, etc.), and the like.

The receptor antagonist of the present invention exhibits the actions similar to the physiological activities (e.g., the histamine releasing activity, etc.) possessed by the ligand of the present invention, and are useful as histamine release inhibitors or safe and low-toxic pharmaceuticals such as agents for the prevention/treatment of, immune diseases [e.g., inflammatory diseases (e.g., pituitary tumor, thyroiditis, peritonitis, Crohn's disease, ulcerative colitis, erythema nodosum, chronic articular rheumatism, systemic lupus erythematosus, etc.), allergy, asthma, secretory otitis media, Meniere's disease, allergic conjunctivitis, contact dermatitis, allergic rhinitis, anaphylaxis, urticaria, myasthenia gravis, glomerulonephritis, Sjögren's syndrome, insulin resistant diabetes, atopic dermatitis, leukocyte abnormality, etc.), edema, acid indigestion, and the like.

The compounds that promote the binding of the receptor of the present invention to the ligand of the present invention are useful as safe and low-toxic pharmaceuticals, such as agents for the prevention/treatment of, for example, nerve growth factor activity potentiators, neurodegenerative diseases (e.g., Alzheimer's diseases, Parkinson's disease, Down's syndrome, amyotrophic lateral sclerosis, prion disease, Creutzfeldt-Jakob disease, Huntington's chorea, diabetic neuropathy, multiple sclerosis, etc.), and the like.

The compounds that inhibit the binding of the receptor of the present invention to the ligand of the present invention are useful as histamine release inhibitors or safe and low-toxic pharmaceuticals such as agents for the prevention/treatment of, immune diseases [e.g., inflammatory diseases (e.g., pituitary tumor, thyroiditis, peritonitis, Crohn's disease, ulcerative colitis, erythema nodosum, chronic articular rheumatism, systemic lupus erythematosus, etc.), allergy, asthma, secretory otitis media, Meniere's disease, allergic conjunctivitis, contact dermatitis, allergic rhinitis, anaphylaxis, urticaria, myasthenia gravis, glomerulonephritis, Sjögren's syndrome, insulin resistant diabetes, atopic dermatitis, leukocyte abnormality, etc.), edema, acid indigestion, and the like.

Also, the present invention provides the method of screening the compound or its salts that promote or inhibit expression of a gene for the receptor of the present invention, which comprises using the polynucleotide of the present invention encoding the receptor of the present invention, etc.

Specifically, the compound or its salts that promote or inhibit expression of a gene for the receptor of the present invention is screened by comparing the case (i) where a cell capable of producing the receptor of the present invention is cultured, with the case (ii) where a mixture of the cell capable of producing the receptor of the present invention and a test compound is cultured.

In the screening method described above, the expression level of the gene for the receptor of the present invention (specifically, the amount of the receptor of the present invention or the amount of mRNA encoding the receptor of the present invention, etc.) is measured in the cases (i) and (ii), and comparison is made.

Examples of the test compounds include peptides, proteins, non-peptide compounds, synthetic compounds, fermentation products, cell extracts, plant extracts, animal tissue extracts, etc. These compounds may be novel compounds or publicly known compounds.

To perform the screening method described above, the cells capable of producing the polypeptide of the present invention or the receptor of the present invention are suspended in a buffer suitable for the screening, and the suspension is prepared. Any buffer can be used so long as it does not interfere the activities of the receptor of the present invention, including a phosphate buffer or a borate buffer, having pH of about 4 to about 10 (preferably pH of about 6 to about 8), etc.

As the cells capable of producing the receptor of the present invention, there are employed, e.g., the aforesaid host (transformant) transformed by a vector containing the DNA encoding the receptor of the present invention. Preferably, animal cells such as CHO cells, etc. are used as the host. For the screening, the transformant, in which the protein of the present invention has been expressed on the cell membrane, e.g., by culturing through the procedure described above, is preferably employed.

The amount of the protein of the receptor of the present invention can be determined by publicly known methods, e.g., by measuring the aforesaid polypeptide or receptor present in the cell extract, etc., using the antibody of the present invention, in accordance with methods like western blot analysis, ELISA, etc., or their modifications.

The expression level of the gene for the receptor of the present invention invention can be determined by publicly known methods, e.g., in accordance with methods including Northern blotting, reverse transcription-polymerase chain reaction (RT-PCR), real time PCR monitoring system (manufactured by ABI, TaqMan polymerase chain reaction), etc., or their modifications.

For example, when a test compound that promotes the expression of the gene for the receptor of the present invention in the case (ii) described above by at least about 20%, preferably at least 30%, more preferably at least about 50%, as compared to the case (i) above, the test compound can be selected to be a compound or its salt that promotes the expression of the gene for the receptor of the present invention.

For example, when a test compound inhibits the expression of the gene for the receptor of the present invention in the case (ii) described above by at least about 20%, preferably at least 30%, more preferably at least about 50%, as compared to, the case (i) above, the test compound can be selected to be a compound or its salt that inhibits the expression of the gene for the receptor of the present invention.

The compound or its salt that promotes the expression of the gene for the receptor of the present invention (increases the expression level) can be used as safe and low-toxic pharmaceuticals, such as agents for the prevention/treatment of, for example, nerve growth factor activity potentiators, neurodegenerative diseases (e.g., Alzheimer's diseases, Parkinson's disease, Down's syndrome, amyotrophic lateral sclerosis, prion disease, Creutzfeldt-Jakob disease, Huntington's chorea, diabetic neuropathy, multiple sclerosis, etc.), and the like, as in the receptor of the present invention.

The compound or its salt that inhibits the expression of the gene for the receptor of the present invention can suppress the physiological activities of the ligand of the present invention on the receptor of the present invention, and is thus useful as histamine release inhibitors or safe and low-toxic pharmaceuticals such as agents for the prevention/treatment of, for example, histamine release inhibitors, immune diseases [e.g., inflammatory diseases (e.g., pituitary tumor, thyroiditis, peritonitis, Crohn's disease, ulcerative colitis, erythema nodosum, chronic articular rheumatism, systemic lupus erythematosus, etc.), allergy, asthma, secretory otitis media, Meniere's disease, allergic conjunctivitis, contact dermatitis, allergic rhinitis, anaphylaxis, urticaria, myasthenia gravis, glomerulonephritis, Sjögren's syndrome, insulin resistant diabetes, atopic dermatitis, leukocyte abnormality, etc.), edema, acid indigestion, and the like.

The compounds or its salts, which are obtained using the screening methods or screening kits of the present invention are the compounds selected from peptides, proteins, non-peptide compounds, synthetic compounds, fermentation products, cell extracts, plant extracts, animal tissue extracts, plasma, etc. and the compounds that change the binding properties of the receptor of the present invention to the ligand of the present invention, the compounds that promote or inhibit the activities or functions of the receptor of the present invention, the the compounds that promote or inhibit expression (increase or decrease the expression level) of the gene for the receptor of the present invention, etc.

The same examples given as the salts of the receptor of the present invention described above apply to the salts of these compounds.

When the compounds or salts thereof obtained by the screening methods or screening kits of the present invention are used as the aforesaid pharmaceuticals (as agents for the prevention/treatment, etc.), the use can be performed in a conventional manner.

The compounds or salts thereof can be used orally, for example, in the form of tablets which may be sugar coated, if necessary, capsules, elixirs, microcapsules etc., or parenterally in the form of injectable preparations such as a sterile solution and a suspension in water or with other pharmaceutically acceptable liquid. These preparations can be manufactured by mixing the compounds or salts thereof with a physiologically acceptable known carrier, a flavoring agent, an excipient, a vehicle, an antiseptic agent, a stabilizer, a binder, etc. in a unit dosage form required in a generally accepted manner that is applied to making pharmaceutical preparations. The active ingredient in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch, gelatin, alginic acid, etc., a lubricant such as magnesium stearate, a sweetening agent such as sucrose, lactose and saccharin, and a flavoring agent such as peppermint, akamono oil or cherry, etc. When the unit dosage is in the form of capsules, liquid carriers such as oils and fats may further be used together with the additives described above. A sterile composition for injection may be formulated according to a conventional manner used to make pharmaceutical compositions, e.g., by dissolving or suspending the active ingredients in a vehicle such as water for injection with a naturally occurring vegetable oil such as sesame oil and coconut oil, etc. to prepare the pharmaceutical composition.

Examples of an aqueous medium for injection include physiological saline and an isotonic solution containing glucose and other auxiliary agents (e.g., D-sorbitol, D-mannitol, sodium chloride, etc.) and may be used in combination with an appropriate dissolution aid such as an alcohol (e.g., ethanol or the like), a polyalcohol (e.g., propylene glycol and polyethylene glycol), a nonionic surfactant (e.g., polysorbate 80™ and HCO-50), etc. Examples of the oily medium include sesame oil and soybean oil, which may also be used in combination with a dissolution aid such as benzyl benzoate and benzyl alcohol. The prophylactic/therapeutic agent described above may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus-prepared liquid for injection is normally filled in an appropriate ampoule.

Since the thus obtained pharmaceutical preparation is safe and low toxic, the preparation can be administered to human or warm-blooded animal (e.g., mouse, rat, rabbit, sheep, swine, bovine, horse, fowl, cat, dog, monkey, chimpanzee, etc.).

The dose of the compounds or salts thereof may vary depending upon the action, target disease, subject to be administered, route of administration, etc.

For example, the compound is orally administered to the patient (as 60 kg body weight) with allergy in a dose of about 0.1 to 100 mg, preferably about 1.0 to 50 mg and more preferably about 1.0 to 20 mg per day. In parenteral administration, when the compound is administered to the patient (as 60 kg) with allergy in the form of injectable preparations, it is advantageous to administer intravenously in a daily dose of about 0.01 to about 30 mg, preferably about 0.1 to about 20 mg and more preferably about 0.1 to about 10 mg. For other animal species, the corresponding dose as converted per 60 kg weight can be administered.

[2] Agents for the Prevention/Treatment for Various Diseases Associated with the the Receptor of the Present Invention The receptor of the present invention has the binding activity, etc. to the ligand of the present invention having the activities described above.

Accordingly, where the receptor of the present invention or the polynucleotide (e.g., DNA) of the present invention involves abnormalities or deficiencies, it is highly likely for one to suffer from, e.g., nerve growth factor activity potentiators, neurodegenerative diseases (e.g., Alzheimer's diseases, Parkinson's disease, Down's syndrome, amyotrophic lateral sclerosis, prion disease, Creutzfeldt-Jakob disease, Huntington's chorea, diabetic neuropathy, multiple sclerosis, etc.), or the like. Thus, the receptor of the present invention or the polynucleotide (e.g., DNA) of the present invention can be used as safe and low-toxic pharmaceuticals such as agents for the prevention/treatment of, for example, nerve growth factor activity potentiators, neurodegenerative diseases (e.g., Alzheimer's diseases, Parkinson's disease, Down's syndrome, amyotrophic lateral sclerosis, prion disease, Creutzfeldt-Jakob disease, Huntington's chorea, diabetic neuropathy, multiple sclerosis, etc.), or the like.

When a patient has a reduced level of, or deficient in the receptor of the present invention in his or her body, the receptor of the present invention and the polynucleotide of the present invention can provide the role of the receptor of the present invention sufficiently or properly for the patient, (a) by administering the polynucleotide of the present invention to the patient to express the polypeptide of the present invention in the body, (b) by inserting the polynucleotide of the present invention into a cell, expressing the receptor of the present invention and then transplanting the cell to the patient, or (c) by administering the receptor of the present invention to the patient, or the like.

When the polynucleotide of the present invention is used as the preventive/therapeutic agents described above, the polynucleotide is administered directly to human or warm-blooded animal; alternatively, the polynucleotide is inserted into an appropriate vector such as retrovirus vector, adenovirus vector, adenovirus-associated virus vector, etc. and then administered to human or other warm-blooded animal in a conventional manner. The polynucleotide of the present invention may also be administered as intact polynucleotide, or with adjuvants to assist its uptake by gene gun or through a catheter such as a catheter with a hydrogel.

Where the receptor of the present invention is used as the aforesaid agents for the prevention/treatment, the receptor is advantageously used on a purity level of at least 90%, preferably at least 95%, more preferably at least 98% and most preferably at least 99%.

The receptor of the present invention can be used orally, for example, in the form of tablets which may be sugar coated if necessary and desired, capsules, elixirs, microcapsules etc., or parenterally in the form of injectable preparations such as a sterile solution and a suspension in water or with other pharmaceutically acceptable liquid. These preparations can be manufactured by mixing the receptor of the present invention with a physiologically acceptable known carrier, a flavoring agent, an excipient, a vehicle, an antiseptic agent, a stabilizer, a binder, etc. in a unit dosage form required in a generally accepted manner that is applied to making pharmaceutical preparations. The active ingredient in the preparation is controlled in such a dose that an appropriate dose is obtained within the specified range given.

Additives miscible with tablets, capsules, etc. include a binder such as gelatin, corn starch, tragacanth and gum arabic, an excipient such as crystalline cellulose, a swelling agent such as corn starch; gelatin, alginic acid, etc., a lubricant such as magnesium stearate, a sweetening agent such as sucrose, lactose and saccharin, and a flavoring agent such as peppermint, akamono oil or cherry, etc. When the unit dosage is in the form of capsules, liquid carriers such as oils and fats may further be used together with the additives described above. A sterile composition for injection may be formulated according to a conventional manner used to make pharmaceutical compositions, e.g., by dissolving or suspending the active ingredients in a vehicle such as water for injection with a naturally occurring vegetable oil such as sesame oil and coconut oil, etc. to prepare the pharmaceutical composition.

Examples of an aqueous medium for injection include physiological saline and an isotonic solution containing glucose and other auxiliary agents (e.g., D-sorbitol, D-mannitol, sodium chloride, etc.) and may be used in combination with an appropriate dissolution aid such as an alcohol (e.g., ethanol or the like), a polyalcohol (e.g., propylene glycol and polyethylene glycol), a nonionic surfactant (e.g., polysorbate 80™ and HCO-50), etc. Examples of the oily medium include sesame oil and soybean oil, which may also be used in combination with a dissolution aid such as benzyl benzoate and benzyl alcohol. The prophylactic/therapeutic agent described above may further be formulated with a buffer (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant, etc. The thus-prepared liquid for injection is normally filled in an appropriate ampoule.

The vector in which the polynucleotide (e.g., DNA) of the present invention is inserted may also be prepared into pharmaceutical preparations in a manner similar to the procedures above. Such preparations are generally used parenterally.

Since the thus obtained pharmaceutical preparation is safe and low toxic, the preparation can be administered to human or warm-blooded animal (e.g., rat, mouse, guinea pig, rabbit, fowl, sheep, swine, bovine, horse, cat, dog, monkey, etc.).

The dose of the receptor of the present invention varies depending on target disease, subject to be administered, route for administration, etc.; for example, when the receptor of the present invention is orally administered for the treatment of Alzheimer's disease, the polypeptide is administered to an adult (as 60 kg) normally in a dose of about 0.1 mg to about 100 mg, preferably about 1.0 to about 50 mg, and more preferably about 1.0 to about 20 mg per day. In parenteral administration, the single dose of the receptor varies depending on subject to be administered, target disease, etc. but when the receptor of the present invention is administered to an adult (as 60 kg body weight) for the treatment of Alzheimer's disease in the form of injectable preparations, it is advantageous to administer the polypeptide or the receptor to the affected area at a daily dose of about 0.01 to about 30 mg, preferably about 0.1 to about 20 mg, and more preferably about 0.1 to about 10 mg. For other animal species, the corresponding dose as converted per 60 kg can be administered.

[3] Quantification of the Receptor of the Present Invention

The antibody to the receptor of the present invention (hereinafter sometimes simply referred to as the antibody (ies) of the present invention) is capable of specifically recognizing the receptor of the present invention, and can thus be used for quantification of the receptor of the present invention in a sample fluid, in particular, for quantification by sandwich immunoassay.

That is, the present invention provides:

(i) a method for quantification of the receptor of the present invention in a sample fluid, which comprises competitively reacting the antibody of the present invention with a sample fluid and a labeled form of the receptor of the present invention, and measuring the ratio of the labeled receptor of the present invention bound to said antibody; and, (ii) a method for quantification of the receptor of the present invention in a sample fluid, which comprises simultaneously or continuously reacting the sample fluid with the antibody of the present invention and a labeled form of another antibody of the present invention immobilized on an insoluble carrier; and measuring the activity of the labeling agent on the immobilized carrier.

In the method (ii) described above, it is preferred that one antibody is capable of recognizing the N-terminal region of the receptor of the present invention, while another antibody is capable of recognizing the C-terminal region of the receptor of the present invention.

The monoclonal antibody to the receptor of the present invention may be used to quantify the receptor of the present invention. Moreover, the receptor of the present invention may also be detected by means of a tissue staining, etc. For these purposes, the antibody molecule per se may be used, or $F(ab')_2$, Fab' or Fab fractions of the antibody molecule may be used as well.

The method of quantifying the receptor of the present invention using the antibody of the present invention is not particularly limited, and any method may be used so far as it relates to a method, in which the amount of an antibody, antigen or antibody-antigen complex can be detected by a chemical or a physical means, depending on or corresponding to the amount of antigen (e.g., the amount of polypeptide) in a sample fluid to be assayed, and then calculated using a standard curve prepared by a standard solution containing the known amount of antigen. Advantageously used are, for example, nephrometry, competitive method, immunometric method and sandwich method; in terms of sensitivity and specificity, the sandwich method, which will be described later, is particularly preferred.

Examples of labeling agents, which are employed for the assay method using the same, are radioisotopes, enzymes, fluorescent substances, luminescent substances, etc. Examples of radioisotopes are $[^{125}I]$, $[^{131}I]$, $[^{3}H]$, $[^{14}C]$, etc. Preferred examples of enzymes are those that are stable and have a high specific activity, which include β-galactosidase, β-glucosidase, alkaline phosphatase, peroxidase, malate dehydrogenase, etc. Examples of fluorescent substances are fluorescamine, fluorescein isothiocyanate, etc. Examples of luminescent substances are luminol, a luminol derivative, luciferin, lucigenin, etc. Furthermore, a biotin-avidin system may be used as well for binding an antibody or antigen to a labeling agent.

In the immobilization of antigens or antibodies, physical adsorption may be used. Alternatively, chemical binding that is conventionally used for immobilization of proteins, enzymes, etc. may be used as well. Examples of the carrier include insoluble polysaccharides such as agarose, dextran, cellulose, etc.; synthetic resins such as polystyrene, polyacrylamide, silicone, etc.; or glass; and the like.

In the sandwich method, a sample fluid is reacted with an immobilized form of the monoclonal antibody of the present invention (primary reaction), then reacted with a labeled form of the monoclonal antibody of the present invention (secondary reaction) and the activity of the labeling agent on the insoluble carrier is assayed; thus, the amount of the receptor in a sample fluid can be determined. The primary and secondary reactions may be carried out in a reversed order, simultaneously or sequentially with intervals. The type of the labeling agent and the method of immobilization may be the same as those described hereinabove. In the immunoassay by the sandwich method, it is not always necessary that the antibody used for the labeled antibody and for the solid phase should be one type or one species but a mixture of two or more antibodies may also be used for the purpose of improving the assay sensitivity, etc.

In the method of assaying the receptor of the present invention by the sandwich method according to the present invention, preferred monoclonal antibodies of the present invention used for the primary and the secondary reactions are antibodies, which binding sites to the receptor of the present invention are different from each other. Thus, the antibodies used in the primary and secondary reactions are those wherein, when the antibody used in the secondary reaction recognizes the C-terminal region of the receptor of the present invention, the antibody recognizing the site other than the C-terminal regions, e.g., recognizing the N-terminal region, is preferably used in the primary reaction.

The monoclonal antibody of the present invention may be used in an assay system other than the sandwich method, such as the competitive method, the immunometric method or the nephrometry.

In the competitive method, an antigen in a sample fluid and a labeled antigen are competitively reacted with an antibody, then an unreacted labeled antigen (F) and a labeled antigen bound to the antibody (B) are separated (i.e., B/F separation) and the labeled amount of either B or F is measured to determine the amount of the antigen in the sample fluid. In the reactions for such a method, there are a liquid phase method in which a soluble antibody is used as the antibody and the B/F separation is effected by polyethylene glycol, while a second antibody to the antibody is used, and a solid phase method in which an immobilized antibody is used as the first antibody or a soluble antibody is used as the first antibody, while an immobilized antibody is used as the second antibody.

In the immunometric method, an antigen in a sample fluid and an immobilized antigen are competitively reacted with a given amount of a labeled antibody followed by separating the solid phase from the liquid phase; or an antigen in a sample fluid and an excess amount of labeled antibody are reacted, then an immobilized antigen is added to bind an unreacted labeled antibody to the solid phase and the solid phase is separated from the liquid phase. Thereafter, the labeled amount of any of the phases is measured to determine the antigen amount in the sample fluid.

In the nephrometry, the amount of insoluble sediment, which is produced as a result of the antigen-antibody reaction in a gel or in a solution, is measured. Even when the amount of an antigen in a sample fluid is small and only a small amount of the sediment is obtained, a laser nephrometry utilizing laser scattering can be suitably used.

In applying each of those immunoassays to the assay method of the present invention, any special conditions, operations, etc. are not required. The assay system for the receptor of the present invention may be constructed in addition to conditions or operations conventionally used for each of the methods, taking technical consideration by one skilled in the art into account. For the details of such conventional technical means, a variety of reviews, reference books, etc. may be referred to.

For example, Hiroshi Irie (ed.): "Radioimmunoassay" (published by Kodansha, 1974); Hiroshi Irie (ed.): "Radioimmunoassay; Second Series" (published by Kodansha, 1979); Eiji Ishikawa, et al. (ed.): "Enzyme Immunoassay" (published by Igaku Shoin, 1978); Eiji Ishikawa, et al. (ed.): "Enzyme Immunoassay" (Second Edition) (published by Igaku Shoin, 1982); Eiji Ishikawa, et al. (ed.): "Enzyme Immunoassay" (Third Edition) (published by Igaku Shoin, 1987); "Methods in Enzymology" Vol. 70 (Immuochemical Techniques (Part A)); ibid., Vol. 73 (Immunochemical Techniques (Part B)); ibid., Vol. 74 (Immunochemical Techniques (Part C)); ibid., Vol. 84 (Immunochemical Techniques (Part D: Selected Immunoassays)); ibid., Vol. 92 (Immunochemical Techniques (Part E: Monoclonal Antibodies and General Immunoassay Methods)); ibid., Vol. 121 (Immunochemical Techniques (Part I: Hybridoma Technology and Monoclonal Antibodies)) (all published by Academic Press); etc.

As described above, the receptor of the present invention can be quantified with high sensitivity, using the antibody of the present invention.

Furthermore, when an increased level of the receptor of the present invention is detected by quantifying the level of the receptor of the present invention using the antibody of the present invention, it can be diagnosed that one suffers from, e.g., immune diseases [e.g., inflammatory diseases (e.g., pituitary tumor, thyroiditis, peritonitis, Crohn's disease, ulcerative colitis, erythema nodosum, chronic articular rheumatism, systemic lupus erythematosus, etc.), allergy, asthma, secretory otitis media, Meniere's disease, allergic conjunctivitis, contact dermatitis, allergic rhinitis, anaphylaxis, urticaria, myasthenia gravis, glomerulonephritis, Sjögren's syndrome, insulin resistant diabetes, atopic dermatitis, leukocyte abnormality, etc.), edema, acid indigestion, or the like; or it is highly likely for one to suffer from these disease in the future. Also, when a decreased level of the receptor of the present invention is detected, it can be diagnosed that one suffers from, e.g., neurodegenerative diseases (e.g., Alzheimer's diseases, Parkinson's disease, Down's syndrome, amyotrophic lateral sclerosis, prion disease, Creutzfeldt-Jakob disease, Huntington's chorea, diabetic neuropathy, multiple sclerosis, etc.), or the like; or it is highly likely for one to suffer from these disease in the future.

The antibody of the present invention may also be employed to detect the receptor of the present invention present in a sample fluid such as body fluids, tissues, etc. The antibody may further be used for the preparation of an antibody column used to purify the receptor of the present invention, detect the receptor of the present invention in each fraction upon purification, analysis of the behavior of the receptor of the present invention in the cells under investigation.

[4] Gene Diagnostic Agent

By using the polynucleotide (DNA) of the present invention, e.g., as a probe, abnormality (gene abnormality) of the DNA or mRNA encoding the receptor of the present invention in human or warm-blooded animal (e.g., rat, mouse, guinea pig, rabbit, fowl, sheep, swine, bovine, horse, cat, dog, monkey, etc.) can be detected. Thus, the polynucleotide is useful as a gene diagnostic agent for the damage to the DNA or mRNA, mutation, a decreased expression or an increased expression, or overexpression of the DNA or mRNA.

The gene diagnosis described above using the DNA of the present invention can be performed by, for example, the publicly known Northern hybridization assay or the PCR-SSCP assay (Genomics, 5, 874–879 (1989); Proceedings of the National Academy of Sciences of the United States of America, 86, 2766–2770 (1989)), etc.

For example, when overexpression of the receptor of the present invention is detected, it can be diagnosed that one is likely to suffer from, for example, immune diseases [e.g., inflammatory diseases (e.g., pituitary tumor, thyroiditis, peritonitis, Crohn's disease, ulcerative colitis, erythema nodosum, chronic articular rheumatism, systemic lupus erythematosus, etc.), allergy, asthma, secretory otitis media, Meniere's disease, allergic conjunctivitis, contact dermatitis, allergic rhinitis, anaphylaxis, urticaria, myasthenia gravis, glomerulonephritis, Sjögren's syndrome, insulin resistant diabetes, atopic dermatitis, leukocyte abnormality, etc.), edema, acid indigestion, etc.; or it is highly likely for one to suffer from diseases in the future. Also, when reduced expression of the receptor of the present invention is detected, it can be diagnosed that one is likely to suffer from, for example, diseases (e.g., Alzheimer's diseases, Parkinson's disease, Down's syndrome, amyotrophic lateral sclerosis, prion disease, Creutzfeldt-Jakob disease, Huntington's chorea, diabetic neuropathy, multiple sclerosis, etc.), etc.; or it is highly likely for one to suffer from diseases in the future.

[5] Pharmaceutical Composition Comprising Antisense DNA

The antisense polynucleotide (e.g., antisense DNA) that binds complementarily to the polynucleotide (e.g., DNA) to inhibit expression of the polynucleotide (e.g., DNA) is useful as low-toxic and safe pharmaceuticals such as agents for the prevention/treatment of, for example, immune diseases [e.g., inflammatory diseases (e.g., pituitary tumor, thyroiditis, peritonitis, Crohn's disease, ulcerative colitis, erythema nodosum, chronic articular rheumatism, systemic lupus erythematosus, etc.), allergy, asthma, secretory otitis media, Meniere's disease, allergic conjunctivitis, contact dermatitis, allergic rhinitis, anaphylaxis, urticaria, myasthenia gravis, glomerulonephritis, Sjögren's syndrome, insulin resistant diabetes, atopic dermatitis, leukocyte abnormality, etc.), edema, acid indigestion, and the like.

When the antisense DNA described above is used, the antisense DNA alone may be administered, or the DNA is inserted into an appropriate vector such as retrovirus vector, adenovirus vector, adenovirus-associated virus vector, etc. and then administered in a conventional manner. The antisense DNA may also be administered as intact DNA, or with adjuvants to assist its uptake by gene gun or through a catheter such as a catheter with a hydrogel.

In addition, the antisense DNA may also be employed as an oligonucleotide probe for diagnosis to examine the presence of the DNA of the present invention in tissues or cells and states of its expression.

As in the antisense polynucleotide described above, the double-stranded RNA containing a part of the RNA encoding the receptor of the present invention, the ribozyme containing a part of the RNA encoding the receptor of the present invention and the like can suppress the expression of the polynucleotide of the present invention and can suppress the in vivo function of the receptor of the present invention or the polynucleotide of the present invention. Thus, they are useful as low toxic and safe pharmaceuticals such as agents for the prevention/treatment of diseases, for example, immune diseases [e.g., inflammatory diseases (e.g., pituitary tumor, thyroiditis, peritonitis, Crohn's disease, ulcerative colitis, erythema nodosum, chronic articular rheumatism, systemic lupus erythematosus, etc.), allergy, asthma, secretory otitis media, Meniere's disease, allergic conjunctivitis, contact dermatitis, allergic rhinitis, anaphylaxis, urticaria, myasthenia gravis, glomerulonephritis, Sjögren's syndrome, insulin resistant diabetes, atopic dermatitis, leukocyte abnormality, etc.), edema, acid indigestion, or the like.

The double-stranded RNA can be designed based on a sequence of the polynucleotide of the present invention and manufactured by modifications of publicly known methods (e.g., Nature, 411, 494, 2001).

The ribozyme can be designed based on a sequence of the polynucleotide of the present invention and manufactured by modifications of publicly known methods (e.g., TRENDS in Molecular Medicine, 7, 221, 2001). For example, the ribozyme can be manufactured by ligating a publicly known ribozyme to a part of the RNA encoding the receptor of the present invention. A part of the RNA encoding the receptor of the present invention includes an adjacent portion to a cleavage site on the RNA of the present invention, which may be cleaved by a publicly known ribozyme (RNA fragment).

Where the double-stranded RNA or ribozyme described above can be used as the agent for the prevention/treatment described above, the RNA or ribozyme can be prepared into pharmaceutical preparations, which are provided for administration, as in the antisense polynucleotide.

[6] Pharmaceutical Composition Comprising the Antibody of the Present Invention

The antibody to the receptor of the present invention is low toxic and safe pharmaceuticals such as agents for the prevention/treatment of diseases, for example, immune diseases [e.g., inflammatory diseases (e.g., pituitary tumor, thyroiditis, peritonitis, Crohn's disease, ulcerative colitis, erythema nodosum, chronic articular rheumatism, systemic lupus erythematosus, etc.), allergy, asthma, secretory otitis media, Meniere's disease, allergic conjunctivitis, contact dermatitis, allergic rhinitis, anaphylaxis, urticaria, myasthenia gravis, glomerulonephritis, Sjögren's syndrome, insulin resistant diabetes, atopic dermatitis, leukocyte abnormality, etc.), edema, acid indigestion, and the like.

The antibody of the present invention having the effect to neutralize the receptor of the present invention (inactivate signal transduction) can be used as drugs for the prevention/treatment of diseases, for example, immune diseases [e.g., inflammatory diseases (e.g., pituitary tumor, thyroiditis, peritonitis, Crohn's disease, ulcerative colitis, erythema nodosum, chronic articular rheumatism, systemic lupus erythematosus, etc.), allergy, asthma, secretory otitis media, Meniere's disease, allergic conjunctivitis, contact dermatitis, allergic rhinitis, anaphylaxis, urticaria, myasthenia gravis, glomerulonephritis, Sjögren's syndrome, insulin resistant diabetes, atopic dermatitis, leukocyte abnormality, etc.), edema, acid indigestion, and the like. The antibody of the present invention to activate the signal transduction of the receptor of the present invention can be used as lox toxic and safe pharmaceuticals, including agents for the prevention/treatment of, for example, neurodegenerative diseases (e.g., Alzheimer's diseases, Parkinson's disease, Down's syndrome, amyotrophic lateral sclerosis, prion disease, Creutzfeldt-Jakob disease, Huntington's chorea, diabetic neuropathy, multiple sclerosis, etc.), and the like.

The pharmaceuticals described above containing the antibody of the present invention can be administered to human or warm-blooded animal (e.g., rat, rabbit, sheep, swine, bovine, cat, dog, monkey, etc.) orally or parenterally, directly as a liquid preparation, or as a pharmaceutical composition in an appropriate preparation form. The dose varies depending on subject to be administered, target disease, conditions, route for administration, etc.; when it is used for the treatment/prevention of the adult patient with, e.g., atopic dermatitis, the antibody of the present invention is advantageously administered to the patient through intravenous injection, normally in a single dose of approximately 0.01 to 20 mg/kg body weight, preferably about 0.1 to about 10 mg/kg body weight, and more preferably about 0.1 to about 5 mg/kg body weight, approximately 1 to 5 times, preferably approximately 1 to 3 times, per day. For other parenteral administration and oral administration, the corresponding dose may be administered. When the conditions are extremely serious, the dose may be increased depending on the conditions.

The antibody of the present invention may be administered directly as it is or as an appropriate pharmaceutical composition. The pharmaceutical composition used for the administration described above contains a pharmacologically acceptable carrier with the aforesaid compounds or salts thereof, a diluent or excipient. Such a composition is provided in the preparation suitable for oral or parenteral administration.

That is, examples of the composition for oral administration include solid or liquid preparations, specifically, tablets (including dragees and film-coated tablets), pills, granules, powdery preparations, capsules (including soft capsules), syrup, emulsions, suspensions, etc. Such a composition is manufactured by publicly known methods and contains a vehicle, a diluent or excipient conventionally used in the field of pharmaceutical preparations. Examples of the vehicle or excipient for tablets are lactose, starch, sucrose, magnesium stearate, etc.

Examples of the composition for parenteral administration that can be used are injections, suppositories, etc. and the injections include the form of intravenous, subcutaneous, transcutaneous, intramuscular and drip injections, etc. Such injections are prepared by publicly known methods, e.g., by dissolving, suspending or emulsifying the aforesaid antibody or its salts in a sterile aqueous or oily liquid medium. For the aqueous medium for injection, for example, physiological saline and isotonic solutions containing glucose and other adjuvant, etc. are used. Appropriate dissolution aids, for example, alcohol (e.g., ethanol), polyalcohol (e.g., propylene glycol or polyethylene glycol), nonionic surfactant [e.g., polysorbate 80, HCO-50 (polyoxyethylene (50 mol) adduct of hydrogenated castor oil)] may be used in combination. For the oily solution, for example, sesame oil, soybean oil and the like are used, and dissolution aids such as benzyl benzoate, benzyl alcohol, etc. may be used in combination. The thus-prepared liquid for injection is normally filled in an appropriate ampoule. The suppository used for rectal administration is prepared by mixing the aforesaid antibody or its salts with conventional suppository base.

The oral or parenteral pharmaceutical composition described above is advantageously prepared in a unit dosage form suitable for the dose of the active ingredient. Examples of such unit dosage form include tablets, pills, capsules, injections (ampoules), suppositories, etc. It is preferred that the antibody described above is contained generally in a dose of 5 to 500 mg per unit dosage form, 5 to 100 mg especially for injections and 10 to 250 mg for other preparations.

Each composition described above may further contain other active components unless formulation with the antibody described above causes any adverse interaction.

[7] DNA Transgenic Animal

The present invention provides a non-human mammal bearing an exogenous DNA encoding the receptor of the present invention (hereinafter merely referred to as the exogenous DNA of the present invention) or its variant DNA (sometimes simply referred to as the exogenous variant DNA of the present invention).

Thus, the present invention provides:

(1) a non-human mammal bearing the exogenous DNA or its variant DNA;

(2) the mammal according to (1), wherein the non-human mammal is a rodent;

(3) the mammal according to (2), wherein the rodent is mouse or rat; and, (4) a recombinant vector bearing the exogenous DNA of the present invention or its variant DNA and capable of being expressed in the mammal.

The non-human mammal bearing the exogenous DNA of the present invention or its variant DNA (hereinafter simply referred to as the DNA transgenic animal of the present invention) can be prepared by transfecting a desired DNA into an unfertilized egg, a fertilized egg, a spermatozoon, a germinal cell containing a primordial germinal cell thereof, or the like, preferably in the embryogenic stage in the development of a non-human mammal (more preferably in the single cell or fertilized cell stage and generally before the 8-cell phase), by standard means, such as the calcium phosphate method, the electric pulse method, the lipofection method, the agglutination method, the microinjection method, the particle gun method, the DEAE-dextran method etc. Also, it is possible to transfect the exogenous, DNA of the present invention into a somatic cell, a living organ, a tissue cell, or the like by the DNA transfection methods, and utilize the transformant for cell culture, tissue culture, etc. In addition, these cells may be fused with the above-described germinal cell by a publicly known cell fusion method to prepare the transgenic animal of the present invention.

Examples of the non-human mammal that can be used include bovine, swine, sheep, goats, rabbits, dogs, cats, guinea pigs, hamsters, mice, rats, and the like. Above all, preferred are rodents, especially mice (e.g., C57BL/6 strain, DBA2 strain, etc. for a pure line and for a cross line, B6C3F$_1$ strain, BDF$_1$ strain B6D2F$_1$ strain, BALB/c strain, ICR strain, etc.) or rats (Wistar, SD, etc.), since they are relatively short in ontogeny and life cycle from a standpoint of preparing model animals for human disease.

"Mammals" in a recombinant vector that can be expressed in the mammals include the aforesaid non-human mammals and human.

The exogenous DNA of the present invention refers to the DNA of the present invention that is once isolated/extracted from mammals, not the DNA of the present invention inherently possessed by the non-human mammals.

The mutant DNA of the present invention includes mutants resulting from variation (e.g., mutation, etc.) in the base sequence of the original DNA of the present invention, specifically DNAs resulting from base addition, deletion, substitution with other bases, etc. and further including abnormal DNA.

The abnormal DNA is intended to mean such a DNA that expresses the abnormal receptor of the present invention and exemplified by the DNA that expresses a polypeptide to suppress the functions of the normal receptor of the present invention.

The exogenous DNA of the present invention may be any one of those derived from a mammal of the same species as, or a different species from, the mammal as the target animal. In transfecting the DNA of the present invention, it is generally advantageous to use the DNA as a DNA construct in which the DNA is ligated downstream a promoter capable of expressing the DNA in the target animal. For example, in the case of transfecting the human DNA of the present invention, a DNA transgenic mammal that expresses the DNA of the present invention to a high level, can be prepared by microinjecting a DNA construct (e.g., vector, etc.) ligated with the human DNA of the present invention into a fertilized egg of the target non-human mammal downstream various promoters, which are capable of expressing the DNA derived from various mammals (e.g., rabbits, dogs, cats, guinea pigs, hamsters, rats, mice, etc.) bearing the DNA of the present invention highly homologous to the human DNA.

As expression vectors for the receptor of the present invention, there are *Escherichia coli*-derived plasmids, *Bacillus subtilis*-derived plasmids, yeast-derived plasmids, bacteriophages such as λ phage, retroviruses such as Moloney leukemia virus, etc., and animal viruses such as vaccinia virus, baculovirus, etc. Of these vectors, *Escherichia coli*-derived plasmids, *Bacillus subtilis*-derived plasmids, or yeast-derived plasmids, etc. are preferably used.

Examples of these promoters for regulating the DNA expression include (1) promoters for the DNA derived from viruses (e.g., simian virus, cytomegalovirus, Moloney leukemia virus, JC virus, breast cancer virus, poliovirus, etc.), and (2) promoters derived from various mammals (human, rabbits, dogs, cats, guinea pigs, hamsters, rats, mice, etc.), for example, promoters of albumin, insulin II, uroplakin II, elastase, erythropoietin, endothelin, muscular creatine kinase, glial fibrillary acidic protein, glutathione S-transferase, platelet-derived growth factor β, keratins K1, K10 and K14, collagen types I and II, cyclic AMP-dependent protein kinase βI subunit, dystrophin, tartarate-resistant alkaline phosphatase, atrial natriuretic factor, endothelial receptor tyrosine kinase (generally abbreviated as Tie2), sodium-potassium adenosine triphosphorylase (Na,K-ATPase), neurofilament light chain, metallothioneins I and IIA, metalloproteinase I tissue inhibitor, MHC class I antigen (H-2L), H-ras, renin, dopamine β-hydroxylase, thyroid peroxidase (TPO), polypeptide chain elongation factor 1α (EF-1α), β actin, α and β myosin heavy chains, myosin light chains 1 and 2, myelin base protein, thyroglobulins, Thy-1, immunoglobulins, H-chain variable region (VNP), serum amyloid component P, myoglobin, troponin C, smooth muscle a actin, preproencephalin A, vasopressin, etc. Among others them, cytomegalovirus promoters, human polypeptide elongation factor 1α (EF-1α) promoters, human and chicken β actin promoters etc., which protein can highly express in the whole body are preferred.

It is preferred that the vectors described above have a sequence for terminating the transcription of the desired messenger RNA in the DNA transgenic animal (generally called a terminator); for example, a sequence, of each DNA derived from viruses and various mammals. SV40 terminator of the simian virus, etc. are preferably used.

In addition, for the purpose of increasing the expression of the desired exogenous DNA to a higher level, the splicing signal and enhancer region of each DNA, a portion of the intron of an eukaryotic DNA may also be ligated at the 5' upstream of the promoter region, or between the promoter, region and the translational region, or at the 3' downstream of the translational region, depending upon purposes.

The translational region for the normal receptor of the present invention can be acquired as a whole or a part of DNA derived from liver, kidney, thyroid cell or fibroblast of human or various mammals (e.g., rabbits, dogs, cats, guinea pigs, hamsters, rats, mice, etc.) or of the genomic DNA from various commercially available genomic DNA libraries, or using as a starting material complementary DNA prepared by a publicly known method from RNA derived from liver, kidney, thyroid cell or fibroblast. Also, an exogenous abnormal DNA can produce a translational region, which is obtained by point mutagenesis variation of the translational region in a normal polypeptide obtained from the cells or tissues described above.

The said translational region can be prepared by a conventional DNA engineering technique, in which the DNA is ligated downstream the aforesaid promoter and if desired, upstream the translation termination site, as a DNA construct capable of being expressed in the transgenic animal.

The exogenous DNA of the present invention is transfected at the fertilized egg cell stage in a manner such that the DNA is certainly present in all the germinal cells and somatic cells of the target mammal. The fact that the exogenous DNA of the present invention is present in the germinal cells of the animal prepared by DNA transfection means that all offspring of the prepared animal will maintain the exogenous DNA of the present invention in all of the germinal cells and somatic cells thereof. The offspring of the animal that inherits the exogenous DNA of the present invention also have the exogenous DNA in all of the germinal cells and somatic cells thereof.

The non-human mammal in which the normal exogenous DNA of the present invention has been transfected can be passaged as the DNA-bearing animal under ordinary rearing environment, by confirming that the exogenous DNA is stably retained by mating.

By the transfection of the exogenous DNA of the present invention at the fertilized egg cell stage, the DNA is retained to be excess in all of the germinal and somatic cells. The fact that the exogenous DNA of the present invention is excessively present in the germinal cells of the prepared animal after transfection means that the exogenous DNA of the present invention is excessively present in all of the germinal cells and somatic cells thereof. The offspring of the animal that inherits the exogenous DNA of the present invention have excessively the exogenous DNA of the present invention in all of the germinal cells and somatic cells thereof.

By acquiring a homozygotic animal having the transfected DNA in both of homologous chromosomes and mating a male and female of the animal, all offspring can be passaged to retain the DNA.

In a non-human mammal bearing the normal DNA of the present invention, the normal DNA of the present invention has expressed to a high level, and may eventually develop the hyperfunction of the receptor of the present invention by promoting the function of endogenous normal DNA. Therefore, the animal can be utilized as a pathologic model animal for such a disease. Specifically, using the normal DNA transgenic animal of the present invention, it is possible to elucidate the mechanism of the hyperfunction of the receptor of the present invention and the pathological mechanism of the disease associated with the receptor of the present invention and to determine how to treat the disease.

Furthermore, since a mammal transfected the exogenous normal DNA of the present invention exhibits an increasing symptom of the receptor of the present invention librated, the animal can be used in tests for screening agents for the prevention/treatment of the disease associated with the receptor of the present invention [e.g., inflammatory diseases (e.g., pituitary tumor, thyroiditis, peritonitis, Crohn's disease, ulcerative colitis, erythema nodosum, chronic articular rheumatism, systemic lupus erythematosus, etc.), allergy, asthma, secretory otitis media, Meniere's disease, allergic conjunctivitis, contact dermatitis, allergic rhinitis, anaphylaxis, urticaria, myasthenia gravis, glomerulonephritis, Sjögren's syndrome, insulin resistant diabetes, atopic dermatitis, leukocyte abnormality, etc.), edema, acid indigestion, and the like].

On the other hand, non-human mammal having the exogenous abnormal DNA of the present invention can be passaged under normal breeding conditions as the DNA-bearing animal by confirming the, stable retaining of the exogenous DNA via crossing. Further, the exogenous DNA to be subjected can be utilized as a starting material by inserting the DNA into the plasmid described above. The DNA construct with promoter can be prepared by conventional DNA engineering techniques. The transfection of the abnormal DNA of the present invention at the fertilized egg cell stage is preserved to be present in all of the germinal and somatic cells of the mammals to be subjected. The fact that the abnormal DNA of the present invention is present in the germinal cells of the animal after DNA transfection means that all of the offspring of the prepared animal have the abnormal DNA of the present invention in all of the germinal and somatic cells. Such an offspring passaged the exogenous DNA of the present invention contains the abnormal DNA of the present invention in all of the germinal and somatic cells. A homozygous animal having the introduced DNA on both of homologous chromosomes can be acquired and then by mating these male and female animals, all the offspring can be bled to have the DNA.

Since non-human mammal having the abnormal DNA of the present invention may express the abnormal DNA of the present invention at a high level, the animal may be the function inactivation type inadaptability to the receptor of the present invention by inhibiting the function of the endogenous normal DNA and can be utilized as its disease model animal. For example, using the abnormal DNA-transgenic animal of the present invention, it is possible to elucidate the mechanism of inadaptability to the receptor of the present invention and to perform to study a method for treatment of this disease.

In a more specific availability, the transgenic animal of the present invention expressing the abnormal DNA of the present invention to a high level is also expected to serve as an experimental model for the elucidation of the mechanism of the functional inhibition (dominant negative effect) of normal polypeptide or receptor by the abnormal polypeptide of the present invention or the abnormal receptor of the present invention in the function inactive type inadaptability to the receptor of the present invention.

A mammal bearing the abnormal exogenous DNA of the present invention is also expected to serve for screening a candidate drug for the treatment of the function inactive type inadaptability to the receptor of the present invention, since the receptor of the present invention is increased in such an animal in its free form.

Other potential applications of two kinds of the transgenic animals described above include:

(1) use as a cell source for tissue culture;

(2) elucidation of the relation to a polypeptide or receptor that is specifically expressed or activated by the receptor of the present invention, by direct analysis of DNA or RNA in tissue of the DNA transgenic animal of the present invention or by analysis of the polypeptide or receptor tissue expressed by the DNA;

(3) research in the function of cells derived from tissues that are cultured usually only with difficulty, using cells of tissue bearing the DNA cultured by a standard tissue culture technique;

(4) screening of a drug that enhances the functions of cells using the cells described in (3) above; and, (5) isolation and purification of the variant polypeptide or receptor of the present invention and preparation of an antibody thereto.

Furthermore, clinical conditions of diseases associated wit the receptor of the present invention [neurodegenerative diseases (e.g., Alzheimer's diseases, Parkinson's disease, Down's syndrome, amyotrophic lateral sclerosis, prion disease, Creutzfeldt-Jakob disease, Huntington's chorea, diabetic neuropathy, multiple sclerosis, etc.), and the like], including the function inactive type inadaptability to the receptor of the present invention can be determined using the DNA transgenic animal of the present invention. Also, pathological findings on each organ in a disease model associated with the receptor of the present invention can be obtained in more detail, leading to the development of a new method for treatment as well as the research and therapy of any secondary diseases associated with the disease.

It is also possible to obtain a free DNA-transfected cell by withdrawing each organ from the DNA transgenic animal of the present invention, mincing the organ and digesting with a proteinase such as trypsin, etc., followed by establishing the line of culturing or cultured cells. Furthermore, the DNA transgenic animal of the present invention can serve as identification of cells capable of producing the receptor of the present invention, and as studies on association with apoptosis, differentiation or proliferation or on the mechanism of signal transduction in these properties to inspect any abnormality therein. Thus, the DNA transgenic animal can provide an effective research material to elucidate the receptor of the present invention and its function and effect.

To develop a therapeutic, drug for the treatment of diseases associated with the receptor of the present invention, including the function inactive type inadaptability to the receptor of the present invention, using the DNA transgenic animal of the present invention, an effective and rapid method for screening can be provided by, using the method for inspection and the method for quantification, etc. described above. It is also possible to investigate and develop a method for DNA therapy for the treatment of diseases associated with the receptor of the present invention, using the DNA transgenic animal of the present invention or a vector capable of expressing the exogenous DNA of the present invention.

[8] Knockout Animal

The present invention provides a non-human mammal embryonic stem cell bearing the DNA of the present invention inactivated and a non-human mammal deficient in expressing the DNA of the present invention.

Thus, the present invention provides:

(1) a non-human embryonic stem cell in which the DNA of the present invention is inactivated;

(2) an embryonic stem cell according to (1), wherein the DNA is inactivated by introducing a reporter gene (e.g., β-galactosidase gene derived from *Escherichia coli*);

(3) an embryonic stem cell according to (1), which is resistant to neomycin;

(4) an embryonic stem cell according to (1), wherein the non-human mammal is a rodent;

(5) an embryonic stem cell according to (4), wherein the rodent is mouse;

(6) a non-human mammal deficient in expressing the DNA of the present invention, wherein the DNA of the present invention is inactivated;

(7) a non-human mammal according to (5), wherein the DNA is inactivated by inserting a reporter gene (e.g., β-galactosidase derived from *Escherichia coli*) therein and the reporter gene is capable of being expressed under control of a promoter for the DNA of the present invention;

(8) a non-human mammal according to (6), which is a rodent;

(9) a non-human mammal according to (8), wherein the rodent is mouse; and,

(10) a method for screening a compound or its salt that promotes or inhibits the promoter activity for the DNA of the present invention, which comprises administering attest compound to the mammal of (7) and detecting expression of the reporter gene.

The non-human mammal embryonic stem cell in which the DNA of the present invention is inactivated refers to a non-human mammal embryonic stem cell that suppresses the ability of the non-human mammal to express the DNA by artificially mutating the DNA of the present invention, or the DNA has no substantial ability to express the receptor of the present invention (hereinafter sometimes referred to as the knockout DNA of the present invention) by substantially inactivating the activity of the receptor of the present invention encoded by the DNA (hereinafter merely referred to as ES cell).

As the non-human mammal, the same examples as described above apply.

Techniques for artificially mutating the DNA of the present invention include deletion of a part or all of the DNA sequence and insertion of or substitution with other DNA, by genetic engineering. By these variations, the knockout DNA of the present invention may be prepared, for example, by shifting the reading frame of a codon or by disrupting the function of a promoter or exon.

Specifically, the non-human mammal embryonic stem cell in which the DNA of the present invention is inactivated (hereinafter merely referred to as the ES cell with the DNA of the present invention inactivated or the knockout ES cell of the present invention) can be obtained by, for example, isolating the DNA of the present invention the desired non-human mammal has, inserting a reporter gene, etc. including a neomycin resistant gene or a hygromycin resistant gene, or a reporter gene such as lacZ (β-galactosidase gene) or cat (chloramphenicol acetyltransferase gene), etc. into its exon site thereby to disable the functions of exon; or by inserting a DNA sequence which terminates gene transcription (e.g., polyA additional signal, etc.) in the intron between exons thereby to inhibit the synthesis of complete messenger RNA to eventually destroy the gene, tranfecting a DNA strand having the thus constructed DNA strand (hereinafter simply referred to as targeting vector) to a chromosome of the subject animal by, e.g., homologous recombination. The thus obtained ES cells are analyzed by the southern hybridization analysis using a DNA sequence on or near the DNA of the present invention as a probe, or by PCR analysis using a DNA sequence on the targeting vector and another DNA sequence near the DNA of the present invention, which is not included in the targeting vector as primers, thereby to screen the knockout ES cell of the present invention.

The parent ES cells to inactivate the DNA of the present invention by homologous recombination, etc. may be the strain already established as described above, or may be originally established by the publicly known method by Evans and Kaufman with modifications. For example, in the case of mouse ES cells, currently it is common practice to use ES cells of the 129 strain. However, since their immunological background is obscure, the C57BL/6 mouse or the $BDF_1$ mouse ($F_1$ hybrid between C57BL/6 and DBA/2), wherein the low ovum availability per C57BL/6 in the C57BL/6 mouse has been improved by crossing with DBA/2, may be preferably used, instead of obtaining a pure line of ES cells with the clear immunological genetic background and for other purposes. The $BDF_1$ mouse is advantageous in that, when a pathologic model mouse is generated using ES cells obtained therefrom, the genetic background can be changed to that of the C57BL/6 mouse by backcrossing with the C57BL/6 mouse, since its background is of the C57BL/6 mouse, in addition to the advantages that the ovum availability per animal is high and ova are robust.

In establishing ES cells, blastocytes at 3.5 days after fertilization are commonly used. In the present invention, embryos are preferably collected at the 8-cell stage, after culturing until the blastocyte stage, the embryos are used to efficiently obtain a large number of early stage embryos.

Although the ES cells used may be of either sex, male ES cells are generally more convenient for generation of a germ cell line chimera and are therefore preferred. It is also desirable that sexes are identified as soon as possible to save painstaking culture time.

Methods for sex identification of the ES cell include the method in which a gene in the sex-determining region on the Y-chromosome is amplified by the PCR process and detected. When this method is used, one colony of ES cells (about 50 cells) is sufficient for sex-determination analysis, which karyotype analysis, for example G-banding method, requires about $10^6$ cells; therefore, the first selection of ES cells at the early stage of culture can be based on sex identification, and male cells can be selected early, which saves a significant amount of time at the early stage of culture.

Second selection can be achieved by, for example, the number of chromosome confirmation by the G-banding method. It is usually desirable that the chromosome number of the obtained ES cells be 100% of the normal number. However, when it is difficult to obtain the cells having the normal number of chromosomes due to physical operation etc. in cell establishment, it is desirable that the ES cell be again cloned to a normal cell (e.g., in mouse cells having the number of chromosomes being 2n=40) after the gene of the ES cells is rendered knockout.

Although the embryonic stem cell line thus obtained shows a very high growth potential, it must be subcultured with great care, since it tends to lose its ontogenic capability.

For example, the embryonic stem cell line is cultured at about 37° C. in a carbon dioxide incubator (preferably about 5% carbon dioxide and about 95% air, or about 5% oxygen, about 5% carbon dioxide and 90% air) in the presence of LEF (1-10000 U/ml) on appropriate feeder cells such as STO fibroblasts, treated with a trypsin/EDTA solution (normally about 0.001 to about 0.5% trypsin/about 0.1 to about 5 mM EDTA, preferably about 0.1% trypsin/1 mM EDTA) at the time of passage to obtain separate single cells, which are then seeded on freshly prepared feeder cells. This passage is normally conducted every 1 to 3 other days; it is desirable that cells be observed at passage and cells found to be morphologically abnormal in culture, if any, be abandoned.

Where ES cells are allowed to reach a high density in mono-layers or to form cell aggregates in suspension under appropriate conditions, they will spontaneously differentiate to various cell types, for example, pariental and visceral muscles, cardiac muscle or the like [M. J. Evans and M. H. Kaufman, Nature, 292, 154, 1981; G. R. Martin, Proc. Natl. Acad. Sci. U.S.A., 78, 7634, 1981; T. C. Doetschman et al., Journal of Embryology Experimental Morphology, 87, 27, 1985]. The cells deficient in expression of the DNA of the present invention, which are obtainable from the differentiated ES cells of the present invention, are useful for studying the receptor of the present invention from an aspect of cell biology.

The non-human mammal deficient in expression of the DNA of the present invention can be identified from a normal animal by measuring the mRNA amount in the subject animal by a publicly known method, and indirectly comparing the levels of expression.

As the non-human mammal, the same examples supra apply.

With respect to the non-human mammal deficient in expression of the DNA of the present invention, the DNA of the present invention can be made knockout by transfecting a targeting vector, prepared as described above, to non-human mammal embryonic stem cells or oocytes thereof, and conducting homologous recombination in which a targeting vector DNA sequence, wherein the DNA of the present invention is inactivated by the transfection, is replaced with the DNA of the present invention on a chromosome of a non-human mammal embryonic stem cell or embryo thereof.

The cells with the DNA of the present invention knockout can be identified by the Southern hybridization analysis using a DNA sequence on or near the DNA of the present invention as a probe, or by PCR analysis using as primers a DNA sequence on the targeting vector and another DNA sequence, which is not included in the targeting vector. When non-human mammalian embryonic stem cells are used, a cell line wherein the DNA of the present invention is inactivated by homologous recombination is cloned; the resulting cloned cell line is injected to, e.g., a non-human mammalian embryo or blastocyst, at an appropriate stage such as the 8-cell stage. The resulting chimeric embryos are transplanted to the uterus of the pseudopregnant non-human mammal. The resulting animal is a chimeric animal composed of both cells having the normal locus of the DNA of the present invention and those having an artificially mutated locus of the DNA of the present invention.

When some germ cells of the chimeric animal have a mutated locus of the DNA of the present invention, an individual, which entire tissue is composed of cells having a mutated locus of the DNA of the present invention can be selected from a series of offspring obtained by crossing between such a chimeric animal and a normal animal, e.g., by coat color identification, etc. The individuals thus obtained are normally deficient in heterozygous expression of the receptor of the present invention. The individuals deficient in homozygous expression of the receptor of the present invention can be obtained from offspring of the intercross between the heterozygotes of the receptor of the present invention.

When an oocyte or egg cell is used, a DNA solution may be injected, e.g., to the prenucleus by microinjection thereby to obtain a transgenic non-human mammal having a targeting vector introduced in a chromosome thereof. From such transgenic non-human mammals, those having a mutation at the locus of the DNA of the present invention can be obtained by selection based on homologous recombination.

As described above, individuals in which the DNA of the present invention is rendered knockout permit passage rearing under ordinary rearing conditions, after the individuals obtained by their crossing have proven to have been knockout.

Furthermore, the genital system may be obtained and maintained by conventional methods. That is, by crossing male and female animals each having the inactivated DNA, homozygote animals having the inactivated DNA in both loci can be obtained. The homozygotes thus obtained may be reared so that one normal animal and two or more homozygotes are produced from a mother animal to efficiently obtain such homozygotes. By crossing male and female heterozygotes, homozygotes and heterozygotes having the inactivated DNA are proliferated and passaged.

The non-human mammal embryonic stem cell, in which the DNA of the present invention is inactivated, is very useful for preparing a non-human mammal deficient in expression of the DNA of the present invention.

Since the non-human mammal, in which the DNA of the present invention is inactivated, lacks various biological activities derived from the receptor of the present invention or the receptor of the present invention, such an animal can be a disease model suspected of inactivated biological activities of the receptor of the present invention or the receptor of the present invention and thus, offers an effective study to investigate causes for and therapy for these diseases.

[8a] Method of Screening Compounds Having Therapeutic/Preventive Effects on Diseases Caused by Deficiency, Damages, etc. of the DNA of the Present Invention The non-human mammal deficient in expression of the DNA of the present invention can be employed for screening of compounds having therapeutic/prophylactic effects on diseases caused by deficiency, damages, etc. of the DNA of the present invention.

That is, the present invention provides the method of screening the compound or its salt having therapeutic/prophylactic effects for diseases caused by deficiency, damages, etc. of the DNA of the present invention, for example, neurodegenerative diseases (e.g., Alzheimer's diseases, Parkinson's disease, Down's syndrome, amyotrophic lateral sclerosis, prion disease, Creutzfeldt-Jakob disease, Huntington's chorea, diabetic neuropathy, multiple sclerosis, etc.), which comprises administering a test compound to the non-human mammal deficient in expression of the DNA of the present invention and observing and measuring a change occurred in the animal.

As the non-human mammal deficient in expression of the DNA of the present invention which can be employed for the screening method, the same examples as given hereinabove apply.

Examples of the test compounds include peptides, proteins, non-peptide compounds, synthetic compounds, fermentation products, cell extracts, vegetable extracts, animal tissue extracts, blood plasma, etc. These compounds may be novel compounds or publicly known compounds.

Specifically, the non-human mammal deficient in expression of the DNA of the present invention is treated with a test compound, comparison is made with an intact animal for control and changes in each organ, tissue, disease conditions, etc. of the animal are used as an indicator to assess the therapeutic/prophylactic effects of the test compound.

For treating an animal to be tested with a test compound, for example, oral administration, intravenous injection, etc. are applied and the treatment is appropriately selected depending upon conditions of the test animal, properties of the test compound, etc. Furthermore, a dose of test compound to be administered can be appropriately chosen depending on method for administration, nature of test compound, etc.

In screening the compounds having the therapeutic/preventive effect on, e.g., neurodegenerative diseases (e.g., Alzheimer's diseases, Parkinson's disease, Down's syndrome, amyotrophic lateral sclerosis, prion disease, Creutzfeldt-Jakob disease, Huntington's chorea, diabetic neuropathy, multiple sclerosis, etc.), a test compound is administered to the non-human mammal deficient in expression of the DNA of the present invention and, learning ability, learning behavior, etc. of the animal are monitored with passage of time.

In the screening method described above, when a test compound is administered to a test animal and found to improve the learning ability of the animal to at least about 10%, preferably at least about 30% and more preferably at least about 50%, the test compound can be selected to be a compound having a prophylactic/therapeutic effect for neurodegenerative diseases (e.g., Alzheimer's diseases, Parkinson's disease, Down's syndrome, amyotrophic lateral sclerosis, prion disease, Creutzfeldt-Jakob disease, Huntington's chorea, diabetic neuropathy, multiple sclerosis, etc.).

The compound obtained using the screening method above is a compound selected from the test compounds described above and exhibits a prophylactic/therapeutic effect for the diseases caused by deficiencies, damages, etc. of the receptor of the present invention, for example, neurodegenerative diseases (e.g., Alzheimer's diseases, Parkinson's disease, Down's syndrome, amyotrophic lateral sclerosis, prion disease, Creutzfeldt-Jakob disease, Huntington's chorea, diabetic neuropathy, multiple sclerosis, etc.). Therefore, the compound can be used as a safe and low toxic drug such as an agent for the prevention/treatment of these diseases. Furthermore, compounds derived from the compound obtained by the screening described above can be used as well.

The compound obtained by the screening method above may be in the form of salts. As such salts, there may be used salts with physiologically acceptable acids (e.g., inorganic acids, organic acids, etc.) or bases (e.g., alkali metal salts, etc.), preferably in the form of physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

A pharmaceutical composition comprising the compound obtained by the above screening method or salts thereof may be manufactured in a manner similar to the method for preparing the pharmaceutical composition comprising the receptor of the present invention described hereinabove.

Since the pharmaceutical composition thus obtained is safe and low toxic, it can be administered to human and another mammal (e.g., rat, mouse, guinea pig, rabbit, sheep, swine, bovine, horse, cat, dog, monkey, etc.).

A dose of the compound or its salt varies depending upon particular disease, subject to be administered, route of administration, etc. For example, when the compound is orally administered, the compound is administered to the adult patient (as 60 kg body-weight) with Alzheimer's disease normally in a dose of about 0.1 mg to about 100 mg, preferably about 1.0 to about 50 mg, and more preferably about 1.0 to about 20 mg per day. In parenteral administration, the single dose of the compound varies depending on subject to be administered, target disease, etc. but when the compound is administered to the adult patient (as 60 kg) with Alzheimer's disease in the form of injectable preparations, it is advantageous to administer the compound intravenously at a daily dose of about 0.01 to about 30 mg, preferably about 0.1 to about 20 mg, and more preferably about 0.1 to about 10 mg. For other animal species, the corresponding dose as converted per 60 kg can be administered

[8b] Method for Screening the Compound that, Promotes or Inhibits the Activities of a Promoter to the DNA of the Present Invention The present invention provides the method of screening the compound or its salt that promotes or inhibits the activity of a promoter to the DNA of the present invention, which comprises administering a test compound to a non-human mammal deficient in expression of the DNA of the present invention and detecting expression of the reporter gene.

In the screening method supra, the non-human mammal deficient in expression of the DNA of the present invention is selected from the aforesaid non-human mammal deficient in expression of the DNA of the present invention, as an animal in which the DNA of the present invention is inactivated by introducing a reporter gene and the reporter gene is expressed under control of a promoter to the DNA of the present invention.

The same examples described above apply to the test compounds.

As the reporter gene, the same specific examples apply to this screening method. Preferably employed are β-galactosidase (lacZ), soluble alkaline phosphatase gene, luciferase gene and the like.

Since a reporter gene is present under control of a promoter to the DNA of the present invention in the non-human mammal deficient in expression of the DNA of the present invention wherein the DNA of the present invention is substituted with the reporter gene, the activity of the promoter can be detected by tracing expression of a substance encoded by the reporter gene.

When a part of the DNA region encoding the receptor of the present invention is substituted with, e.g., β-galactosidase gene (lacZ) derived from *Escherichia coli*; β-galactosidase is expressed in a tissue where the receptor of the present invention should originally be expressed, instead of the receptor of the present invention. Thus, the state of expression condition of the receptor of the present invention can be readily observed in vivo of an animal by staining with a reagent, e.g., 5-bromo-4-chloro-3-indolyl-β-galactopyranoside (X-gal) which is substrate for β-galactosidase. Specifically, a mouse deficient in the receptor of the present invention, or its tissue slice section is fixed with glutaraldehyde, etc. After washing with phosphate buffered saline (PBS), the system is reacted with a staining solution containing X-gal at room temperature or about 37° C. for approximately 30 minutes to an hour. After the β-galactosidase reaction is terminated by washing the tissue preparation with 1 mM EDTA/PBS solution, the color formed is observed. Alternatively, mRNA encoding lacZ may: be detected in a conventional manner.

The compound or salts thereof obtained using the aforesaid screening method are compounds selected from the test compounds described above and the compounds that promote or inhibit the promoter activity to the DNA of the present invention.

The compound obtained by the screening method above may form salts. As salts of the compound, there may be used salts with physiologically acceptable acids (e.g., inorganic acids, etc.) or bases (e.g., organic acids, etc.), and especially preferred are physiologically acceptable acid addition salts. Examples of such salts are salts with inorganic acids (e.g., hydrochloric acid, phosphoric acid, hydrobromic acid, sulfuric acid, etc.), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.) and the like.

The compounds or salts thereof that promote the promoter activity to the DNA of the present invention can promote expression of the receptor of the present invention thereby to promote the activities or functions of the polypeptide or the receptor of the present invention. Thus, these compounds are useful as safe and low toxic drugs such as agents for the prevention/treatment of, e.g., neurodegenerative diseases (e.g., Alzheimer's diseases, Parkinson's disease, Down's syndrome, amyotrophic lateral sclerosis, prion disease, Creutzfeldt-Jakob disease, Huntington's chorea, diabetic neuropathy, multiple sclerosis, etc.).

Also, the compounds or salts thereof that inhibit the promoter activity to the DNA of the present invention can inhibit expression of the receptor of the present invention, thus inhibiting the activities or functions of the receptor of the present invention. Accordingly, these compounds are useful as safe and low toxic drugs such as agents for the prevention/treatment of, e.g., immune diseases, [e.g., inflammatory diseases (e.g., pituitary tumor, thyroiditis, peritonitis, Crohn's disease, ulcerative colitis, erythema nodosum, chronic articular rheumatism, systemic lupus erythematosus, etc.), allergy, asthma, secretory otitis media, Meniere's disease, allergic conjunctivitis, contact dermatitis, allergic rhinitis, anaphylaxis, urticaria, myasthenia gravis, glomerulonephritis, Sjögren's syndrome, insulin resistant diabetes, atopic dermatitis, leukocyte, abnormality, etc.), edema, acid indigestion, and the like.

In addition, compounds derived from the compounds obtained by the screening described above may also be used similarly.

The pharmaceuticals comprising the compounds obtained by the screening method or salts thereof may be manufactured as in the aforesaid pharmaceuticals containing the compounds or salts thereof obtained by the screening method of the present invention described above.

Since the pharmaceutical preparations thus obtained are safe and low toxic, the preparations can be administered to human and another mammal (e.g., rat, mouse, guinea pig, rabbit, sheep, swine, bovine, horse, cat, dog, monkey, etc.).

A dose of the compound or its salt varies depending upon target disease, subject to be administered, route of administration, etc. For example, when the compound that promotes the promoter activity to the DNA of the present invention is orally administered, the compound is administered to the adult patient (as 60 kg body weight) with Alzheimer's disease, the compound is administered generally in a dose of approximately 0.1 to 100 mg, preferably approximately 1.0 to 50 mg, more preferably approximately 1.0 to 20 mg per day. In parenteral administration, a single dose of the compound varies depending upon subject to be administered, target disease, etc. When the compound that promotes the promoter activity to the DNA of the present invention is administered to the adult patient (as 60 kg body weight) with Alzheimer's disease in the form of an injectable preparation, it is advantageous to administer the compound intravenously in a dose of approximately 0.01 to 30 mg, preferably approximately 0.1 to 20 mg, more preferably approximately 0.1 to 10 mg per day. For other animals, the compound can be administered in the corresponding dose with converting it into that for the 60 kg.

On the other hand, when the compound that inhibits the promoter activity to the DNA of the present invention is orally administered, the compound is administered to the adult patient (as 60 kg body weight) with atopic dermatitis; generally in a dose of approximately 0.1 to 100 mg, preferably approximately 1.0 to 50 mg, more preferably approximately 1.0 to 20 mg per day. In parenteral administration, a single dose of the compound varies depending upon subject to be administered, target disease, etc. When the compound that inhibits the promoter activity to the DNA of the present invention is administered to the adult patient (as 60 kg) with atopic dermatitis in the form of an injectable preparations it is advantageous to administer the compound intravenously in a dose of approximately 0.01 to 30 mg, preferably approximately 0.1 to 20 mg; more preferably approximately 0.1 to 10 mg per day. For other animals, the compound can be administered in the corresponding dose with converting it into that for the 60 kg body weight.

As described above, the non-human mammal deficient in expressing the DNA of the present invention is extremely useful for screening the compound or its salt that promotes or inhibits the activity of a promoter to the DNA of the present invention, and thus can greatly contribute to investigations of causes for various diseases caused by failure to express the DNA of the present invention or to development of preventive/therapeutic agents for these diseases.

Moreover, when a so-called transgenic animal (gene-transfected animal) is prepared by using a DNA containing the promoter region in the receptor of the present invention, ligating genes encoding various proteins downstream the same and injecting the genes into animal oocyte, the polypeptide can be specifically synthesized by the animal so that it becomes possible to investigate the activity in vivo. In addition, when an appropriate reporter gene is ligated to the promoter region described above to establish a cell line so as to express the gene, such can be used as a survey system of low molecular weight compounds that specifically promotes or suppresses the ability of producing the receptor itself of the present invention in vivo.

In the specification and drawings, the codes of bases and amino acids are shown by abbreviations and in this case, they are denoted in accordance with the IUPAC-IUB Commission on Biochemical Nomenclature or by the common codes in the art, examples of which are shown below. For amino acids that may have the optical isomer, L form is presented unless otherwise indicated.

DNA: deoxyribonucleic acid
cDNA: complementary deoxyribonucleic acid
A: adenine
T: thymine
G: guanine
C: cytosine
I: inosine
R: adenine (A) or guanine (G)
Y: cytosine (C) or thymine (T)
M: adenine (A) or cytosine (C)
K: guanine (G) or thymine (T)
S: guanine (G) or cytosine (C)
W: adenine (A) or thymine (T)
B: guanine (G), guanine (G) or thymine (T)
D: adenine (A), guanine (G) or thymine (T)
V: adenine (A), guanine (G) or cytosine (C)
N: adenine (A), guanine (G), cytosine (C) or thymine (T), or unknown or other base
RNA: ribonucleic acid
mRNA: messenger ribonucleic acid
dATP: deoxyadenosine triphosphate
dTTP: deoxythymidine triphosphate
dGTP: deoxyguanosine triphosphate
dCTP: deoxycytidine triphosphate
ATP: adenosine triphosphate
EDTA: ethylenediaminetetraacetic acid
SDS: sodium dodecyl sulfate
BHA: benzhydrylamine
pMBHA: p-methyobenzhydrylamine
Tos: p-toluenesulfonyl
Bzl: benzyl
Bom: benzyloxymethyl
Boc: t-butyloxycarbonyl
DCM: dichloromethane
HOBt: 1-hydroxybenztriazole
DCC: N,N'-dicyclohexylcarbodiimide
TFA: trifluoroacetic acid
DIEA: diisopropylethylamine
Gly or G: glycine
Ala or A: alanine
Val or V: valine
Leu or L: leucine
Ile or I: isoleucine
Ser or S: serine
Thr or T: threonine
Cys or C: cysteine
Met or M: methionine
Glu or E: glutamic acid
Asp or D: aspartic acid
Lys or K: lysine
Arg or R: arginine
His or H: histidine
Phe or F: phenylalanine
Tyr or Y: tyrosine
Trp or W: tryptophan
Pro or P: proline
Asn or N: asparagine
Gln or Q: glutamine
pGlu: pyroglutamic acid
Tyr (I): 3-iodotyrosine
DMF: N,N-dimethylformamide
Fmoc: N-9-fluorenylmethoxycarbonyl
Trt: trityl
Pbf: 2,2,4,6,7-pentamethyldihydrobenzofuran-5-sulfonyl
Clt: 2-chlorotrityl
Bu$^t$: t-butyl
Met (O): methionine sulfoxide The sequence identification numbers in the sequence listing of the specification indicates the following sequence, respectively.

[SEQ ID NO: 1]
This shows the amino acid sequence of human derived G protein-coupled receptor protein GPR34.

[SEQ ID NO: 2]
This shows the base sequence of cDNA encoding human derived G protein-coupled receptor protein GPR34.

[SEQ ID NO: 3]
This shows the base sequence of primer 1 used for PCR in EXAMPLE 1 (1-1) below.

[SEQ ID NO: 4]
This shows the base sequence of primer 2 used for PCR in EXAMPLE 1 (1-1) below.

[SEQ ID NO: 5]
This shows the base sequence of primer 3 used for PCR in EXAMPLE 1 (1-3) below.

[SEQ ID NO: 6]
This shows the base sequence of primer 4 used for PCR in EXAMPLE 1 (1-3) below.

[SEQ ID NO: 7]
This shows the base sequence of probe used for PCR in EXAMPLE 1 (1-3) below. At the 5' end, FAM (6-carboxy-fluorescein) was labeled as a reporter dye and TAMRA (6-carboxy-tetramethyl-rhodamine) was labeled as a quencher at the 3' end.

[SEQ ID NO: 8]
This shows the base sequence of primer 1 used for PCR in EXAMPLE 2 below.

[SEQ ID NO: 9]
This shows the base sequence of primer 2 used for PCR in EXAMPLE 2 below.

[SEQ ID NO: 10]
This shows the base sequence of cDNA fragment encoding a part of rat-derived G protein-coupled receptor protein GPR34.

[SEQ ID NO: 11]
This shows the base sequence of primer 1 used for PCR in EXAMPLE 3 below.

[SEQ ID NO: 12]
This shows the base sequence of primer 2 used for PCR in EXAMPLE 3 below.

[SEQ ID NO: 13]
This shows the base sequence of the partial sequence of cDNA at the 3' end, encoding rat-derived G protein-coupled receptor protein GPR34.

[SEQ ID NO: 14]
This shows the base sequence of primer 1 used for PCR in EXAMPLE 4 below.

[SEQ ID NO: 15]
This shows the base sequence of primer 2 used for PCR in EXAMPLE 4 below.

[SEQ ID NO: 16]

This shows the base sequence of the partial sequence of cDNA at the 5' end, encoding rat-derived G protein-coupled receptor protein GPR34.

[SEQ ID NO: 17]

This shows the base sequence of primer 1 used for PCR in EXAMPLE 5 below.

[SEQ ID NO: 18]

This shows the base sequence of primer 2 used for PCR in EXAMPLE 5 below.

[SEQ ID NO: 19]

This shows the amino acid sequence of rat-derived G protein-coupled receptor protein GPR34.

[SEQ ID NO: 20]

This shows the base sequence of cDNA encoding rat-derived G protein-coupled receptor protein GPR34.

[SEQ ID NO: 21]

This shows the base sequence of cDNA encoding rat-derived G protein-coupled receptor protein GPR34 obtained in EXAMPLE 5 below.

[SEQ ID NO: 22]

This shows the amino acid sequence of mouse-derived G protein-coupled receptor protein GPR34 (Accession No. AAD50550).

[SEQ ID NO: 23]

This shows the base sequence of cDNA encoding mouse-derived G protein-coupled receptor protein GPR34 (Accession No. AF081916).

*Escherichia coli* DH5α-T1/pCR2.1-TOPO-ratGPR34 obtained in EXAMPLE 5 later described has been on deposit since Apr. 25, 2002 under Accession Number FERM BP-8032 at the National Institute of Advanced Industrial Science and Technology, International Patent Organism Depositary, located at Central 6, 1-1-1 Higashi, Tsukuba, Ibaraki, Japan (postal code 305-8566), and since Apr. 16, 2002 has been on deposit at the Institute for Fermentation (IFO), located at 2-17-85, Juso-honmachi, Yodogawa-ku, Osaka-shi, Osaka, Japan (postal code 532-8686) under Accession Number IFO 16792.

EXAMPLES

The present invention is described in more detail below with reference to EXAMPLES, but is not deemed to limit the scope of the present invention thereto.

Example 1

(1-1) Cloning of cDNA Encoding Human-Derived G Protein-Coupled Receptor Protein GPR34 and Preparation of Animal Cell Expression Vector Using human genome (CLONTECH) as a template together with SalI recognition site-added primer 1 (SEQ ID NO: 3) and SpeI recognition site-added primer 2 (SEQ ID NO: 4), PCR was carried out. In this reaction, 100 ng of the genome described above was used as a template and the reaction solution comprised of 2.5 U of Pfu Turbo DNA Polymerase (STRATAGENE), 1.0 µM each of primer 1 (SEQ ID NO: 3) and primer 2(SEQ ID NO: 4), 200 µM of dNTPs, and 25 µl of 2×GC Buffer I (TaKaRa Shuzo Co., Ltd.) was added to the enzyme to make the volume 50 µl. PCR was carried out by maintaining at 94° C. for 1 minute and then repeating 38 times one cycle set to include 94° C. for 30 seconds, 54° C. for 15 seconds and 72° C. for 1.5 minutes. The PCR product was purified using PCR Purification Kit (QIAGEN). Elution was performed in 30 µl of Buffer EB attached to the kit, and 10 µl of the eluate was digested with restriction enzymes SalII and SpeI. After gel electrophoresis, the restriction enzyme reaction product was excised from the agarose gel and recovered using Gel Extraction Kit (QIAGEN). The reaction product was added to vector plasmid pAKKO-111H for animal cell expression (the same vector plasmid as pAKKO1.11H described in Biochim. Biophys. Acta, 1219, 251–259, 1994), which was digested with SalI and SpeI, followed by ligation using DNA Ligation Kit Ver.2 (TaKaRa Shuzo Co., Ltd.). The digestion product was transfected to *Escherichia coli* TOP10 (Invitrogen) and clones bearing cDNA of GPR34 were selected in LB agar medium containing ampicillin. As a result of analysis of the sequence of each clone, *Escherichia coli* bearing the plasmid (which was named pAKKO-GPR34) containing the base sequence (SEQ ID NO: 2) of cDNA encoding GPR34 (SEQ ID NO: 1) was obtained. After *Escherichia coli* TOP10 transfected by this pAKKO-GPR34 was incubated, plasmid DNA of pAKKO-GPR34 was prepared using Plasmid Miniprep Kit (BIORAD). The amino acid sequence of GPR34 obtained coincided with the amino acid sequence of GPR34 described in Genomics, 56, 12–21, 1999, and the 181 amino acid in the amino acid sequence was Leu. The 181 amino acid in the amino acid sequence of GPR34 described in Biochim. Biophys. Acta, 1446, 57–70, 1999 is Val.

(1-2) Preparation of GPR34-Expressed CHO Cell Line

Hamster CHO/dhfr⁻ cells were plated on a Falcon dish (3.5 cm in diameter) with α-MEM medium (GIBCO Cat.No.12571) containing 10% cow fetal serum in 1×10⁵, followed by incubation at 37° C. in a 5% CO$_2$ incubator. Using Transfection Reagent FuGENE6 (Roche), 2 µg of the expression plasmid pAKKO-GPR34 obtained in (1-1) described above was transfected according to the method described in the instructions attached. After incubation for 18 hours, the medium was replaced by a fresh growth medium. Incubation was continued for further 10 hours. Then, the transfected cells were collected by trypsin-EDTA treatment and plated on a flat-bottomed 96-well plate with selective medium (α-MEM medium containing 10% fetal calf serum (GIBCO Cat. No. 12561)). While exchanging the selective medium every 3 to 4 days, incubation was continued to acquire 76 clones of DHFR⁺ cells grown in colonies 2 to 3 weeks after.

(1-3) Quantification of GPR34 Expression Level in GPR34-Expressed CHO Cell Line Using TaqMan PCR On a 96-well plate, 76 clones from the GPR34-expressed CHO cell line obtained in (1-2) described above were incubated and the total RNA was prepared using RNeasy 96 Kit (QIAGEN). Using TaqMan Reverse Transcription Reagents (Applied Biosystems), 1 to 200 ng of the total RNA obtained was subjected to reverse transcription. The obtained reverse transcription product corresponding to 0.1–20 ng of the total RNA, or 0.1–20 ng of the total RNA without reverse transcription, or standard cDNA prepared as later described, 0.5 µM each of 2 primers [primer 3 (SEQ ID NO: 5) and primer 4 (SEQ ID NO: 6)] and 0.1 µM of probe 1 (SEQ ID NO: 7; the 5' end and the 3' end were labeled with Fam (6-carboxy-fluorescein) and Tamra (6-carboxy-tetramethyl-rhodamine), respectively) were added with 25 µl of TaqMan Universal PCR Master Mix (Applied Biosystems) to make the volume 50 µl, and PCR was carried out. Using ABI7700 (Applied Biosystems), PCR was carried out by meaning at 50° C. for 2 minutes and 95° C. for 10 minutes, and then repeating 40 times one cycle set to include 95° C. for 15 seconds and 60° C. for 1 minute.

By measuring absorbance at 260 nm of the plasmid pAKKO-GPR34 obtained in (1-1) described above, the level of cDNA was calculated and the copy number was accurately calculated. After diluting with 10 mM Tris-HCl (pH 8.0) solution containing 1 mM EDTA, the standard cDNA solution of $1\times10^6$ copies was prepared from 1 copy. The probe and primers for TaqMan PCR were designed by Primer Express Ver. 1.0 (Applied Biosystems).

The expression level was computed by ABI PRISM 7700 SDS software. The cycle number at the moment when the fluorescence intensity of the reporter reached the given value was taken on the ordinate and the logarithmic value of the initial concentration of standard cDNA was taken on the abscissa to prepare the standard curve. The number of the copies in each reverse transcription product and the total RNA without reverse transcription was calculated from the standard curve. By subtracting the value obtained by the PCR product without reverse transcription from the value obtained by the PCR product of reverse transcription product, the expression level of GPR34 gene in each clone per 1 ng of the total RNA was determined. As a result, 12 CHO cell lines with high GPR34 expression were selected and cultured on a 24-well plate. The expression level of GPR34 was reexamined on these cells. After the total RNA was prepared using RNeasy Mini Kit (QIAGEN), reverse transcription was performed as described above to determine the expression level of GPR34 gene in each clone per 1 ng of the total RNA by TaqMan PCR. As a result, the GPR34-expressed CHO cell line clone Nos. 1-5 and 1-9 were found to show high expression levels.

In EXAMPLES below, the expression cells of these two clones were used.

(1-4) Assay for the Intracellular cAMP Production Inhibitory Activity Using the GPR34-Expressed CHO Cells The GPR34-expressed CHO cells prepared in (1-2) described above and selected in (1-2) described above were plated on a 24-well plate in $6\times10^4$ cells/well followed by incubation for 48 hours. The cells were washed with αMEM medium (pH 7.5) containing 0.2 mM 3-isobutyl-methylxanthine, 0.05% BSA and 20 mM HEPES (hereinafter αMEM medium (pH 7.5) containing 0.2 mM 3-isobutyl-methylxanthine, 0.05% BSA and 20 mM HEPES is referred to as the reaction buffer). Thereafter, 0.5 mL of the reaction buffer was added and the mixture was kept warm for 30 minutes in an incubator. The reaction buffer was removed and 0.25 mL of fresh reaction buffer was replenished to the cells. Then, 0.25 mL of the reaction buffer containing a sample and 2 µM forskolin was added to the cells, followed by reacting at 37° C. for 30 minutes. The reaction solution was removed and 0.5 mL of the cell lysis solution attached to cAMP EIA kit (Applied Biosystems) to extract cAMP in the cells. The cAMP level in the extract was quantified using the same kit. Based on this measurement data, the cAMP production inhibitory activity was calculated based on the equation shown below and expressed in terms of percentage to the control group. The activity in the group added with sample was calculated using each control value set on the same plate.

% of control=$(X-C)/(T-C)\times100$ wherein
X: cAMP level in the group added with sample
T: mean value of the cAMP levels in 3 wells of the groups without sample addition and with forskolin stimulation
C: mean value of the cAMP levels in 2 wells of the groups without sample addition and without forskolin stimulation (1-5) cAMP Production Inhibitory Activity of Lysophosphatidylserine and Phosphatidylserine on the GPR34-Expressed CHO Cells The amino acid sequence of GPR34 is known to have low homology to the amino acid sequence of the platelet-activating factor receptor or the uridine diphosphate glycoside. Thus, various compounds including platelet-activating factor and uridine diphosphate glycoside, which are ligands to the receptors showing homology to GPR34, were administered to the GPR34-expressed CHO cells to examine the cAMP production inhibitory activity of these compounds on the GPR34-expressed CHO cells by the method shown in (1-4) described above.

As a result, two compounds, i.e., lysophosphatidylserine (Sigma, L 5772) and phosphatidylserine (Sigma,P 7769) in a higher concentration showed marked activities. The effect was not noted on the other receptor expression cells but was receptor-specific. Based on these results, it was concluded that these two compounds were ligands to GPR34. FIG. 1 shows the cAMP production inhibitory activities when lysophosphatidylserine and phosphatidylserine were administered to the GPR34-expressed CHO cells.

(1-6) Screening of the Compound That Changes the Binding Properties of GPR34 to Lysophosphatidylserine or Phosphatidylserine The GPR34-expressed CHO cells prepared in (1-2) described above and selected in (1-2) described above were plated on a 24-well plate in $6\times10^4$ cells/well followed by incubation for 48 hours. The cells were washed with αMEM medium (pH 7.5) containing 0.2 mM 3-isobutyl-methylxanthine, 0.05% BSA and 20 mM HEPES (hereinafter αMEM medium (pH 7.5) containing 0.2 mM 3-isobutyl-methylxanthine, 0.05% BSA and 20 mM HEPES is referred to as the reaction buffer). Thereafter, 0.5 mL of the reaction buffer was added and the mixture was kept warm for 30 minutes in an incubator. The reaction buffer was removed and 0.25 mL of fresh reaction buffer was replenished to the cells. Then, (a) 0.25 mL of the reaction buffer containing 2 µM forskolin with addition of 1 µM lysophosphatidylserine or 10 µM phosphatidylserine or (b) 0.25 mL of the reaction buffer containing 2 µM forskolin with addition of 1 µM lysophosphatidylserine or 10 µM phosphatidylserine and a test compound, was added to the cells, followed by reacting at 37° C. for 30 minutes. The reaction solution was removed and 0.5 mL of the cell lysis solution attached to cAMP EIA kit (Applied Biosystems) to extract cAMP in the cells. The cAMP level in the extract was quantified using the same kit. Based on this measurement data, the cAMP production inhibitory activity was calculated based on the equation shown below and expressed in terms of percentage to the control group. The activity in the group added with sample was calculated using each control value set on the same plate.

% of control=$(X-C)/(T-C)\times100$ wherein
X: cAMP level in the group added with sample
T: mean value of the cAMP levels in 3 wells of the groups without sample addition and with forskolin stimulation C: mean value of the cAMP levels in 2 wells of the groups without sample addition and without forskolin stimulation The effect of the test compound on the cAMP production inhibitory activity by lysophosphatidylserine or phosphatidylserine was examined by comparing the cAMP production inhibitory activity when lysophosphatidylserine or phosphatidylserine was added to the cells and the cAMP production inhibitory activity when lysophosphatidylserine or phosphatidylserine and the test compound were added to the cells.

The test compound that attenuates the cAMP production inhibitory activity by lysophosphatidylserine or phosphatidylserine is selected to be a candidate substance capable of competitive inhibition; and the test compound that potentiates the cAMP production inhibitory activity by lysophosphatidylserine or phosphatidylserine is selected to be a candidate substance capable of promoting the binding (binding of lysophosphatidylserine or phosphatidylserine to GPR34).

Example 2

Cloning of cDNA Fragment Encoding a Part of Rat-Derived G Protein-Coupled Receptor Protein GPR34

In order to acquire cDNA encoding a part of rat-derived G protein-coupled receptor protein GPR34, PCR was carried out using primer 1 (SEQ ID NO: 8) and primer 2 (SEQ ID NO: 9) designed based on the consensus sequence between human GPR34 and mouse GPR34. The volume of the solution for PCR was made 20 µl and the composition was as follows: 1 µl of rat whole brain Marathon ready cDNA (CLONTECH) as a template, 0.2 µM each of the primers, 0.2 mM dNTP, 0.5 M GC-Melt, 1/50 volume of Advantage-GC, 2 Polymerase Mix (CLONTECH) and 1/5 volume of 5-fold condensed buffer. The cycle for amplification was performed by maintaining at 96° C. for 2 minutes, repeating 35 times one cycle set to include 96° C. for 30 seconds, 54° C. for 30 seconds and 72° C. for 1 minute, and then maintaining at 72° C. for 10 minutes. Using TOPO TA cloning kit (INVITROGEN), the reaction solution was subcloned to plasmid vector pCR2.1-TOPO and transfected to *Escherichia coli* DH5α-T1. From the resulting transformant, the plasmid DNA was purified using QIAwell 8 Ultra Plasmid Kit (QIAGEN). The reaction for base sequencing was carried out using BigDye Terminator Cycle Sequence Ready Reaction Kit (PERKIN-ELMER). As a result of decoding on a fluorescent automatic sequencer, the base sequence represented by SEQ ID NO: 10, which is the sequence of cDNA fragment encoding a part of rat-derived G protein-coupled receptor protein GPR34, was obtained.

Example 3

Cloning of the Partial Sequence of cDNA at the 3' End, Encoding Rat-Derived G Protein-Coupled Receptor Protein GPR34 by 3' RACE Rat whole brain Marathon ready cDNA (CLONTECH) was used as a template for 3' RACE. The primer set used for RACE PCR was the adaptor primer 1 attached to the kit and primer 1 (SEQ ID NO: 11) for the first PCR, and the adaptor primer 2 attached to the kit and primer 2 (SEQ ID NO: 12) for the second PCR, respectively. In the first PCR, the volume of the PCR solution was made 50 µl and the composition was as follows: 5 µl of template cDNA, 0.2 µM each of the primers, 0.2 mM dNTP, 1/50 volume of Advantage 2 Polymerase Mix (CLONTECH), and 1/10 volume of 10-fold condensed buffer. The cycle for amplification was performed by maintaining at 94° C. for 2 minutes, then repeating 30 times one cycle set to include 94° C. for 30 seconds and 68° C. for 2 minutes and maintaining at 72° C. for 10 minutes. In the second PCR, the volume of the PCR solution was made 50 µl and the composition was as follows: 5 µl of a 10-fold dilution of the first PCR reaction solution as a template, 0.2 µM each of the primers, 0.2 mM dNTP, 1/50 volume of Advantage 2 Polymerase Mix and 1/10 volume of 10-fold condensed buffer. The cycle for amplification was performed by maintaining at 94° C. for 2 minutes, then repeating 20 times one cycle set to include 94° C. for 30 seconds and 69° C. for 2 minutes and maintaining at 72° C. for 10 minutes. The reaction product was electrophoresed on 0.8% Seakem LE Agarose (TaKaRa Shuzo Co., Ltd.). A band around 800 bp observed when stained with ethidium bromide was extracted with QIAquick Gel Extraction Kit (QIAGEN), subcloned to plasmid vector pCR2.1-TOPO using TOPO TA cloning kit (INVITROGEN), and transfected to *Escherichia coli* DH5α-T1. The plasmid DNA was purified from the resulting transformant using QIAwell 8 Ultra Plasmid Kit (QIAGEN). The reaction for base sequencing was carried out using BigDye Terminator Cycle Sequence Ready Reaction Kit (PERKIN-ELMER). As a result of decoding on a fluorescent automatic sequencer, the base sequence represented by SEQ ID NO: 13, which is the partial sequence of cDNA at the 3' end, encoding rat-derived G protein-coupled receptor protein GPR34, was obtained.

Example 4

Cloning of the Partial Sequence of cDNA at the 3' End, Encoding Rat-Derived G Protein-Coupled Receptor Protein GPR34 by 5' RACE Rat spleen Marathon ready cDNA (CLONTECH) was used as a template for 5' RACE. The primer set used for RACE PCR was the adaptor primer 1 attached to the kit and primer 1 (SEQ ID NO: 14) for the first PCR, and the adaptor primer 2 attached to the kit and primer 2 (SEQ ID NO: 15) for the second PCR, respectively. In the first PCR, the volume of the PCR solution was made 50 µl and the composition was as follows: 5 µl of template cDNA, 0.2 µM each of the primers, 0.2 mM dNTP, 1/50 volume of Advantage 2 Polymerase Mix (CLONTECH), and 1/10 volume of 10-fold condensed buffer. The cycle for amplification was performed by maintaining at 94° C. for 30 seconds, then repeating 5 times one cycle set to include 94° C. for 5 seconds and 72° C. for 3 minutes, 5 times 94° C. for 5 seconds and 70° C. for 3 minutes and 25 times one cycle set to include 94° C. for 5 seconds and 68° C. for 3 minutes, and maintaining at 72° C. for 10 minutes. In the second PCR, the volume of the PCR solution was made 50 µl and the composition was as follows: 5 µl of a 10-fold dilution of the first PCR reaction solution as a template, 0.2 µM each of the primers, 0.2 mM dNTP, 1/50 volume of Advantage 2 Polymerase Mix and 1/10 volume of 10-fold condensed buffer. The cycle for amplification was performed by maintaining at 94° C. for 2 minutes, then repeating 30 times one cycle set to include 94° C. for 30 seconds and 69° C. for 2 minutes and maintaining at 72° C. for 10 minutes. The reaction solution was subcloned to plasmid vector pCR2.1-TOPO using TOPO TA cloning kit (INVITROGEN) and transfected to *Escherichia coli* DH5α-T1. The plasmid DNA was purified from the resulting transformant using QIAwell 8 Ultra Plasmid Kit (QIAGEN). The reaction for base sequencing was carried out using BigDye Terminator Cycle Sequence Ready Reaction Kit (PERKIN-ELMER). As a result of decoding on a fluorescent automatic sequencer, the base sequence represented by SEQ ID NO: 16, which is the partial sequence of cDNA at the 5' end, encoding rat-derived G protein-coupled receptor protein GPR34, was obtained.

Example 5

Cloning of the Full-Length Sequence for cDNA Encoding Rat-Derived G Protein-Coupled Receptor Protein GPR34

In order to obtain a putative sequence including the full length sequence for cDNA encoding rat-derived G protein-coupled receptor protein GPR34 predicted from the results of 5' and 3' RACE, primer 1 (SEQ ID NO: 17) and primer 2(SEQ ID NO: 18) was designed and PCR was carried out. The volume of the solution for PCR was made 50 μl and the composition was as follows: 3 μl of rat spleen Marathon ready cDNA (CLONTECH) as a template, 0.2 μM each of the primers, 0.2 mM dNTP, 0.5 M GC-Melt, 1/50 volume of Advantage-GC 2 Polymerase Mix (CLONTECH) and 1/5 volume of 5-fold condensed buffer. The cycle for amplification was performed by maintaining at 96° C. for 2 minutes, repeating 35 times one cycle set to include 96° C. for 30 seconds, 54° C. for 30 seconds and 72° C. for 60 seconds, and then maintaining at 72° C. for 10 minutes. Using TOPO TA cloning kit (INVITROGEN), the reaction solution was subcloned to plasmid vector pCR2.1-TOPO and transfected to *Escherichia coli* DH5α-T1. From the resulting transformant, the plasmid DNA was purified using QIAwell 8 Ultra Plasmid Kit (QIAGEN). The reaction for base sequencing was performed using BigDye Terminator Cycle Sequence Ready Reaction Kit (PERKIN-ELMER). As a result of decoding on a fluorescent automatic sequencer, the base sequence represented by SEQ ID NO: 21 was obtained. This sequence contained the base sequence (SEQ ID NO: 20) of cDNA encoding the full-length amino acid sequence (SEQ ID NO: 19) of rat-derived G protein-coupled receptor protein GPR34. Using this plasmid, *Escherichia coli* DH5α-T1 was transfected to acquire *Escherichia coli* DH5α-T1/pCR2.1-TOPO-ratGPR34.

Example 6

Chemotaxis Stimulating Activity of Human-Derived GPR34-Expressed CHO Cells by Lysophosphatidylserine Chemotaxis stimulating activity of lysophosphatidylserine on human-derived GPR34-expressed CHO cells prepared by the method as described in EXAMPLE 1 was assayed as follows.

Chemotaxis assay was conducted using a 96-well chemotaxis chamber (Neuro Probe). Polycarbonate frame filter (Neuro Probe) with a pore size of 5 μm was immersed in 10 μg/ml of bovine fibronectin (Yagai Research Center) diluted with PBS at room temperature for 10 minutes and then air-dried for pre-treatment. Human GPR34-expressed CHO cells was stripped by Trypsin-EDTA(GIBCO), the medium was replaced by DMEM (Nikken Seibutsu Kagaku Kenkyusho) and the cells were resuspended to prepare $1\times10^6$ cells/ml of cell suspension. In a lower chamber of 96-well chemotaxis chamber, 37 μl of lysophosphatidylserine solutions with various concentrations in DMEM were charged, and the human-derived GPR34-expressed CHO cell suspension prepared in $1\times10^6$ cells/ml was charged in an upper chamber in 200 μl/well ($2\times10^5$ cells/well). After incubation for 5 hours in a $CO_2$ incubator, the cells which that did not migrate from the top of the filter were scraped with Kimwipe (CRECIA) and the CHO cells that migrated to the bottom of the filter were immobilized and stained with Diff-Quick (International Reagents Corp.). Absorbance at 595 nm was measured with a plate reader.

Figure 2:
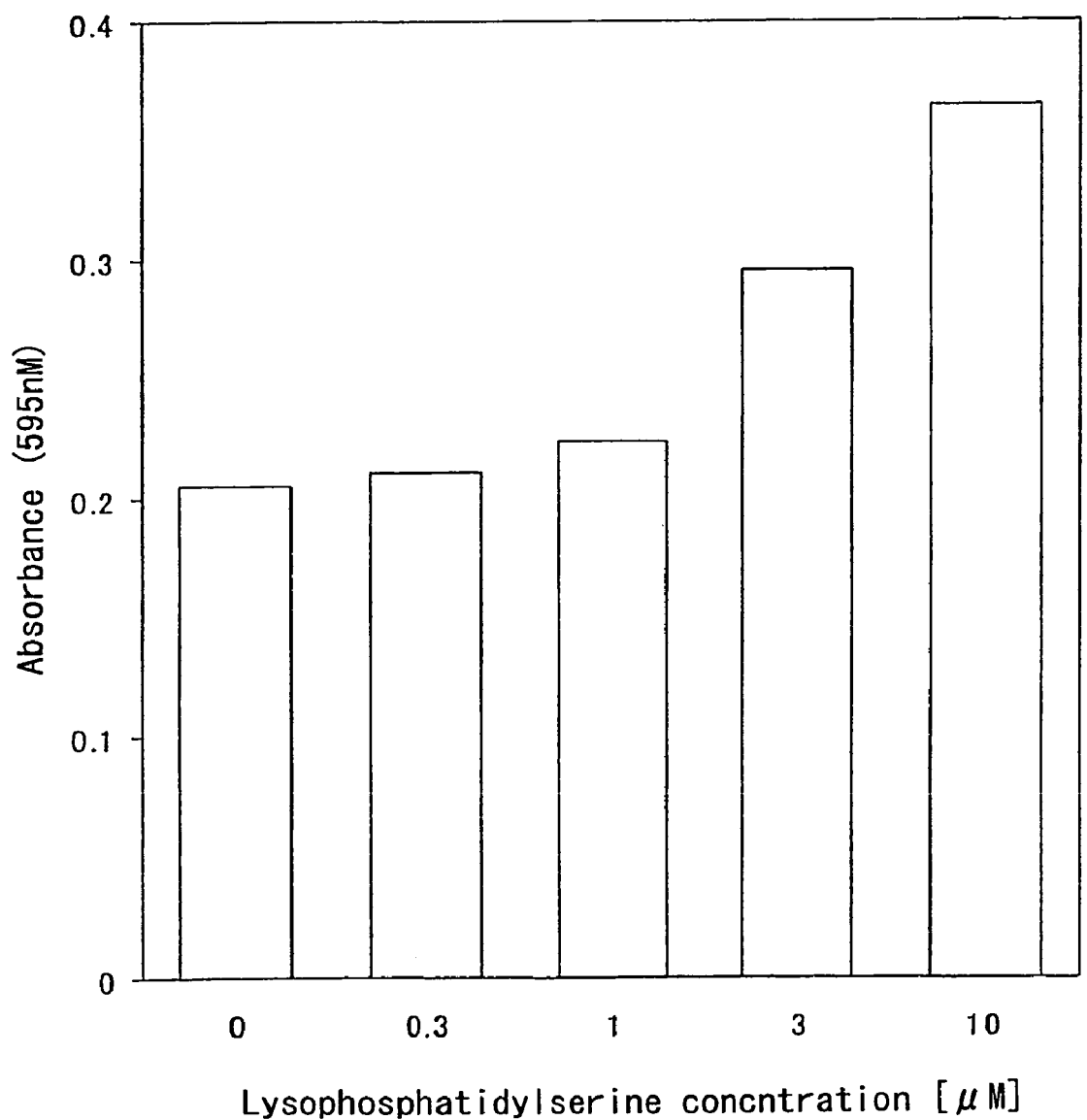
FIG. 2 shows the chemotaxis stimulating activity of lysophosphatidylserine on the GPR34-expressed CHO cells.

FIG. 2 shows the chemotaxis stimulating activity of lysophosphatidylserine on the human-derived GPR34-expressed CHO cells in concentrations of 0, 0.3, 1, 3 and 10 μM, in terms of absorbance at 595 nm.

The results reveal that the human-derived GPR34-expressed CHO cells exhibit the chemotaxis activity in response to lysophosphatidylserine. The chemotaxis activity was confirmed with 1 μM or higher, increased dependently on the concentration of lysophosphatidylserine and showed the maximum chemotaxis activity in 10 μM. The $EC_{50}$ value of the chemotaxis activity was about 2.5 μM.

Example 7

(7-1) Synthesis of 1-[9,10-$^3H_2$]-steraroyl-sn-glycero-3-phospho-L-serine (1-[9,10-$^3H_2$]-stearoyl-lysophosphatidylserine):

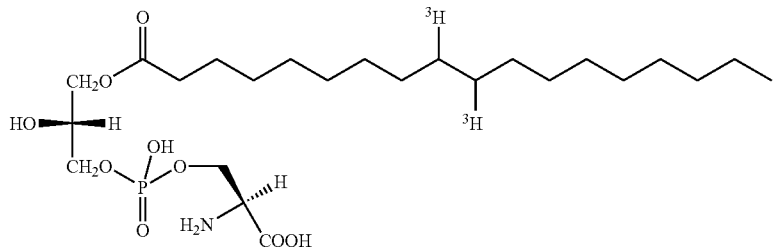

To perform the binding test using lysophosphatidylserine and GPR34-expressed CHO cell membrane fraction, $^3H$-labeled lysophosphatidylserine was synthesized as follows.

First, 1-oleoyl-sn-glycero-3-phospho-L-serine (1-oleoyl-lysophosphatidylserine) having double bond was prepared for $^3H$ labeling by catalytic hydrogenation.

After 1,2-dioleoyl-sn-glycero-3-phospho-L-serine sodium salt (SIGMA, P1060) (85 mg) was dissolved in distilled water (25 ml), 200 mM Tris-HCl buffer (pH 8.0) (1.5 ml) and 100 mM potassium chloride (1.5 ml) were added to the solution, and phospholipase A2 (0.3 ml) (10 mg/ml, 5 mM sodium acetate buffer (pH 5.0)) was further added thereto. The mixture was reacted at room temperature for 20 hours, and the pH was rendered 2 to 3 with 5M hydrochloric acid to terminate the reaction. After the reaction solution was concentrated to dryness, the residue was dissolved in a chloroform-methanol solvent mixture and the solution was adsorbed on silica gel column chromatography. Elution was performed with a chloroform-methanol solvent mixture to give 1-oleoyl-sn-glycero-3-phospho-L-serine.

Subsequently, 1-oleoyl-sn-glycero-3-phospho-L-serine was catalytically hydrogenated with gaseous tritium ($^3H_2$) in the presence of palladium, in accordance with publicly known methods (e.g., the methods described in R. F. Glascock, Isotopic Gas Analysis for Biochemists, 227, Academic Press, New York, 1954) to introduce tritium into the double bond. Thus, the objective product, 1-[9,10-$^3H_2$]-stearoyl-sn-glycero-3-phospho-L-serine was obtained.

(7-2) Preparation of Human-Derived GPR34-Expressed CHO Cell Membrane Fraction

The human-derived GPR34-expressed CHO cells prepared by a modification of the method described in EXAMPLE 1 were incubated. Then, 10 ml of homogenate buffer (10 mM $NaHCO_3$, 5 mM EDTA (ethylenediaminetetraacetate), 0.5 mM PMSF (phenylmethanesulfonyl fluoride), 1 μg/ml pepstatin, 4 μg/ml E64, 20 μg/ml leupeptin) was added to the cells of $1 \times 10^8$, followed by homogenization using a polytron (12,000 rpm, 1 minute). The cell homogenate was centrifuged (1,000 g, 15 minutes) to give the supernatant. Next, the supernatant was subjected to ultracentrifugation (Beckman type 30 rotor, 30,000 rpm, 1 hour) to give the human-derived GPR34-expressed CHO cell membrane fraction as precipitates.

(7-3) Receptor Binding Test Using 1-[9,10-$^3H_2$]-stearoyl-sn-glycero-3-phospho-L-serine (hereinafter abbreviated as [$^3H$]-lysoPS) and human-derived GPR34-expressed CHO cell membrane fraction The cell membrane fraction prepared in (7-2) described above was diluted to various concentrations in assay buffer (25 mM Tris-HCl, 5 mM EDTA, 0.05% CHAPS (3-[(3-cholamidopropyl)dimethylammonio]-1-propanesulfate), 0.1% BSA, 0.5 mM PMSF, 1 μg/ml pepstatin, 20 μg/ml leupeptin, 4 μg/ml E-64, pH 7.4) and a 200 μl aliquot of the dilution was dispensed in a polypropylene-made test tube (Falcon 2053). In order to measure the maximum binding level, 2 μl of DMSO and 2 μl of 80 nM [$^3H$]-lysoPS were added to the membrane fraction solution. Further in order to measure non-specific binding, 2 μl of a solution of 10 mM lysophosphatidylserine in DMSO and 2 μl of 80 nM [$^3H$]-lysoPS were added to the membrane fraction solution. After reacting at 25° C. for 75 minutes, the reaction solution was suction filtered using Whatman glass filter (GF-F) treated with polyethyleneimine and the filter was further washed twice with 1.5 ml of wash buffer (25 mM Tris-HCl, 5 mM EDTA, 0.05% CHAPS, 0.1% BSA, pH 7.4). After filtration, the radioactivity remained on the filter paper was measured with a scintillation counter. The specific binding (SB) was estimated by subtracting the radioactivity of the non-specific binding from the radioactivity (TB) for the maximum binding.

(7-4) Screening of the Compound That Changes the Binding Properties of GPR34 to Lysophosphatidylserine by the Receptor Binding Test In (7-3) described above, 2 μl of the DMSO solution of a test compound and 2 μl of 80 nM [$^3H$]-lysoPS were added to the membrane fraction solution. After the mixture was reacted at 25° C. for 75 minutes, the reaction solution was suction filtered through Whatman glass filter (GF-F) treated with polyethyleneimine, and the filter was further washed twice with 1.5 ml of wash buffer (25 mM Tris-HCl, 5 mM EDTA, 0.05% CHAPS, 0.1% BSA, pH 7.4). After filtration, the radioactivity remained on the filter paper was measured with a scintillation counter. When this radioactivity is made X, the binding inhibitory activity of the test compound is expressed by (TB−X)/SB×100(%).

With respect to the test compounds showing the binding inhibitory activity, the 50% inhibitory concentration ($IC_{50}$ value) can be determined by assaying the binding inhibitory activity using the test compounds prepared in various concentrations. The compound which give a lower $IC_{50}$ value are selected as compounds which inhibit the binding of GPR34 to lysophosphatidylserine more potently.

On the other hand, the compounds which give negative values in the binding inhibitory activity are selected as the compounds that promote the binding of GPR34 to lysophosphatidylserine.

INDUSTRIAL APPLICABILITY

The compounds, which are obtainable by the screening methods or screening kits of the present invention, or salts thereof, the receptors of the present invention, etc. are useful as agents for the prevention/treatment of, for example, neurodegenerative diseases (e.g., Alzheimer's diseases, Parkinson's disease, Down's syndrome, amyotrophic lateral sclerosis, prion disease, Creutzfeldt-Jakob disease, Huntington's chorea, diabetic neuropathy, multiple sclerosis, etc.), immune diseases [e.g., inflammatory diseases (e.g., pituitary tumor, thyroiditis, peritonitis, Crohn's disease, ulcerative colitis, erythema nodosum, chronic articular rheumatism, systemic lupus erythematosus, etc.), allergy, asthma, secretory otitis media, Meniere's disease, allergic conjunctivitis, contact dermatitis, allergic rhinitis, anaphylaxis, urticaria, myasthenia gravis, glomerulonephritis, Sjögren's syndrome, insulin resistant diabetes, atopic dermatitis, leukocyte abnormality, etc.), edema, acid indigestion, histamine release inhibitors, nerve growth factor activity potentiators, etc.

In more detail, the receptor agonists of the present invention, the receptors of the present invention, the DNAs of the present invention, etc. are useful as growth factor activity potentiators or safe and low toxic pharmaceuticals such as agents for the prevention/treatment of, for example, neurodegenerative diseases (e.g., Alzheimer's diseases, Parkinson's disease, Down's syndrome, amyotrophic lateral sclerosis, prion disease, Creutzfeldt-Jakob disease, Huntington's chorea, diabetic neuropathy, multiple sclerosis, etc.) or the like. The receptor antagonists of the present invention, the antibodies of the present invention, the antisense polynucleotides of the present invention, etc. are useful as histamine release inhibitors or safe and low toxic pharmaceuticals such as agents for the prevention/treatment of, for example, immune diseases [e.g., inflammatory diseases (e.g., pituitary tumor, thyroiditis, peritonitis, Crohn's disease, ulcerative colitis, erythema nodosum, chronic articular rheumatism, systemic lupus erythematosus, etc.), allergy, asthma, secretory otitis media, Meniere's disease, allergic conjunctivitis, contact dermatitis, allergic rhinitis, anaphylaxis, urticaria, myasthenia gravis, glomerulonephritis, Sjögren's syndrome, insulin resistant diabetes, atopic dermatitis, leukocyte abnormality, etc.), edema, acid indigestion, etc.

The invention claimed is:

1. A method for screening compounds which change binding properties of (i) a protein, its partial peptide, or a salt of the protein or the partial peptide with (ii) a ligand which binds specifically to the protein, its partial peptide, or a salt of the protein or the partial peptide, said method comprising:

(A) contacting (i) the protein, its partial peptide, or a salt of the protein or the partial peptide with (ii) the ligand;

(B) contacting (i) the protein, its partial peptide, or a salt of the protein or the partial peptide with (ii) the ligand in the presence of a test compound;

(C) detecting an activity or a binding amount of (i) the protein, its partial peptide, or a salt of the protein or the partial peptide with (ii) the ligand in the instance of (A) and (B); and (D) comparing the results to identify compounds which change the binding properties of (i) the protein, its partial peptide, or a salt of the protein or the partial peptide with (ii) the ligand, wherein said protein comprises the same or substantially the same amino acid sequence as an amino acid sequence represented by SEQ ID NO: 1 or SEQ ID NO: 19, and said ligand is a compound represented by the formula below:

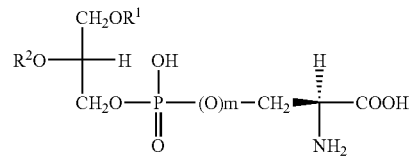

wherein $R^1$ represents a hydrogen atom, alkyl, alkenyl, alkynyl, cycloalkyl, or acyl, wherein each alkyl, alkenyl, alkynyl, or cycloalkyl may optionally have a substituent;

m represents 0 or 1; and $R^2$ represents a hydrogen atom, alkyl, alkenyl, alkynyl, cycloalkyl, or acyl, wherein each alkyl, alkenyl, alkynyl, or cycloalkyl may optionally have a substituent, or a group represented by the formula below:

(III)

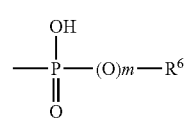

wherein $R^6$ represents a hydrogen atom, alkyl which may optionally have a substituent, or cycloalkyl which may optionally have a substituent, and m is 0 or 1; or a salt thereof.

2. The screening method according to claim 1, wherein the protein comprising the same or substantially the same amino acid sequence as the amino acid sequence represented by SEQ ID NO: 1 is a protein comprising an amino acid sequence represented by SEQ ID NO: 22.

3. The screening method according to claim 1, wherein the protein consisting of the amino acid sequence represented by SEQ ID NO: 1.

4. The screening method according to claim 1, which comprises (a) contacting the ligand with the protein, its partial peptide, or a salt of the protein or the partial peptide to measure a binding amount of the ligand to the protein, its partial peptide, or a salt of the protein or the partial peptide; (b) contacting the ligand and a test compound with the protein, its partial peptide, or a salt of the protein or the partial peptide to measure a binding amount of the ligand to the protein, its partial peptide, or a salt of the protein or the partial peptide; and (c) comparing the binding amount obtained in step (a) with that obtained in step (b).

5. The screening method according to claim 1, which comprises (a) contacting the ligand with a cell comprising the protein, its partial peptide, or a salt of the protein or the partial peptide, or a membrane fraction of the cell to measure a binding amount of the ligand to the cell or the membrane fraction; (b) contacting the ligand and a test compound with the cell comprising the protein, its partial peptide, or a salt of the protein or the partial peptide, or the membrane fraction of the cell to measure a binding amount of the ligand to the cell or the membrane fraction; and (c) comparing the binding amount obtained in step (a) with that obtained in step (b).

6. The screening method according to claim 4, wherein the protein, its partial peptide, or a salt of the protein or the partial peptide is expressed on a cell membrane by culturing a transformant comprising a DNA encoding the protein, its partial peptide, or a salt of the protein or the partial peptide.

7. The screening method according to any one of claims 4 to 6, wherein the ligand is a labeled ligand.

8. The screening method according to claim 1, which comprises (a) contacting the ligand with the protein, its partial peptide, or a salt of the protein or the partial peptide to assay a cell stimulating activity mediated by the protein, its partial peptide, or a salt of the protein or the partial peptide; (b) contacting the ligand and a test compound with the protein, its partial peptide, or a salt of the protein or the partial peptide to assay a cell stimulating activity mediated by the protein, its partial peptide, or a salt of the protein or the partial peptide; and (c) comparing the cell stimulating activity obtained in step (a) with that obtained in step (b).

9. The screening method according to claim 1, which comprises (a) contacting the ligand with a cell comprising the protein, its partial peptide, or a salt of the protein or the partial peptide, or a membrane fraction of the cell to assay a cell stimulating activity mediated by the protein, its partial peptide, or a salt of the protein or the partial peptide; (b) contacting the ligand and a test compound with the cell comprising the protein, its partial peptide, or a salt of the protein or the partial peptide, or the membrane fraction of the cell to assay a cell stimulating activity mediated by the protein, its partial peptide, or a salt of the protein or the partial peptide; and (c) comparing the cell stimulating activity obtained in step (a) with that obtained in step (b).

10. The screening method according to claim 8, wherein the protein, its partial peptide, or a salt of the protein or partial peptide is expressed on a cell membrane by culturing a transformant comprising a DNA encoding the protein, its partial peptide, or a salt of the protein or the partial peptide.

11. A kit for screening a compound or its salt that changes the binding properties of a protein containing the same or substantially the same amino acid sequence as the amino acid sequence represented by SEQ ID NO: 1 or SEQ ID NO: 19, or a salt thereof, to a ligand capable of binding specifically to the protein or its salt, comprising (a) the protein or its salt and (b) the ligand capable of binding specifically to the protein or its salt, said ligand being a compound represented by the formula below:

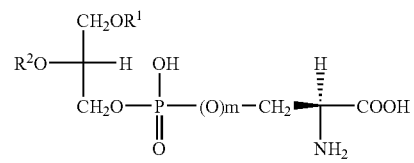

wherein $R^1$ represents a hydrogen atom, alkyl, alkenyl, alkynyl, cycloalkyl, or acyl, wherein each alkyl, alkenyl, alkynyl, or cycloalkyl may optionally have a substituent;

m represents 0 or 1; and $R^2$ represents a hydrogen atom, alkyl, alkenyl, alkynyl, cycloalkyl, or acyl, wherein each alkyl, alkenyl, alkynyl, or cycloalkyl may optionally have a substituent, or a group represented by the formula below:

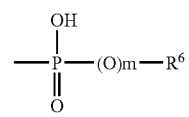

(III)

wherein $R^6$ represents a hydrogen atom, alkyl which may optionally have a substituent, or cycloalkyl which may optionally have a substituent, and m is 0 or 1; or a salt thereof.

12. The screening method according to claim 1, wherein the ligand is a compound of the above formula wherein $R^2$ represents a hydrogen atom.

13. The screening method according to claim 1, wherein $R^1$ represents acyl.

14. The screening method according to claim 1, wherein $R^1$ represents $C_{1-30}$ alkyl-carbonyl.

15. The screening method according to claim 1, wherein the ligand is 1-stearoyl-sn-glycero-3-phospho-L-serine, 1-palmitoyl-sn-glycero-3-phospho-L-serine, or 1-oleoyl-sn-glycero-3-phospho-L-serine.

16. The screening method according to claim 7, wherein the ligand is 1-[9, 10-$^3$H$_2$]-stearoyl-sn-glycero-3-phospho-L-serine.

17. The screening method according to claim 11, wherein the ligand is a compound of the above formula wherein, $R^2$ represents a hydrogen atom.

18. The screening method according to claim 1, wherein said compounds comprise a salt with an inorganic acid, organic acid or alkali metal.

19. The screening method according to claim 18, wherein said inorganic acid is selected from the group consisting of a hydrochloric acid, phosphoric acid, hydrobromic acid and sulfuric acid; and said organic acid is selected from the group consisting of an acetic acid, formic acid, propionic acid, fumaric acid, maleic acid, succinic acid, tartaric acid, citric acid, malic acid, oxalic acid, benzoic acid, methanesulfonic acid and benzenesulfonic acid.

20. The screening method according to claim 1, wherein said salt of the protein or the partial peptide is a salt with an inorganic acid, organic acid or alkali metal.

21. The screening method according to claim 20, wherein said inorganic acid is selected from the group consisting of a hydrochloric acid, phosphoric acid, hydrobromic acid and sulfuric acid; and said organic acid is selected from the group consisting of an acetic acid, formic acid, propionic acid, fumaric acid, maleic acid, succinic acid, tartaric acid, citric acid, malic acid, oxalic acid, benzoic acid, methanesulfonic acid and benzenesulfonic acid.

22. The screening method according to claim 1, wherein said compounds are selected from the group consisting of peptides, proteins, non-peptide compounds, synthetic compounds, fermentation products, cell extracts, plant extracts, animal tissue extracts and plasma.

* * * * *

SEQUENCE LISTING

<160> NUMBER OF SEQ ID NOS: 23

<210> SEQ ID NO 1
<211> LENGTH: 381
<212> TYPE: PRT
<213> ORGANISM: Human

<400> SEQUENCE: 1

```
Met Arg Ser His Thr Ile Thr Met Thr Thr Ser Val Ser Ser Trp
                5                   10                  15

Pro Tyr Ser Ser His Arg Met Arg Phe Ile Thr Asn His Ser Asp Gln
            20                  25                  30

Pro Pro Gln Asn Phe Ser Ala Thr Pro Asn Val Thr Thr Cys Pro Met
        35                  40                  45

Asp Glu Lys Leu Leu Ser Thr Val Leu Thr Thr Ser Tyr Ser Val Ile
    50                  55                  60

Phe Ile Val Gly Leu Val Gly Asn Ile Ile Ala Leu Tyr Val Phe Leu
65                  70                  75                  80

Gly Ile His Arg Lys Arg Asn Ser Ile Gln Ile Tyr Leu Leu Asn Val
                85                  90                  95

Ala Ile Ala Asp Leu Leu Leu Ile Phe Cys Leu Pro Phe Arg Ile Met
            100                 105                 110

Tyr His Ile Asn Gln Asn Lys Trp Thr Leu Gly Val Ile Leu Cys Lys
        115                 120                 125

Val Val Gly Thr Leu Phe Tyr Met Asn Met Tyr Ile Ser Ile Ile Leu
    130                 135                 140

Leu Gly Phe Ile Ser Leu Asp Arg Tyr Ile Lys Ile Asn Arg Ser Ile
145                 150                 155                 160

Gln Gln Arg Lys Ala Ile Thr Thr Lys Gln Ser Ile Tyr Val Cys Cys
                165                 170                 175

Ile Val Trp Met Leu Ala Leu Gly Gly Phe Leu Thr Met Ile Ile Leu
            180                 185                 190

Thr Leu Lys Lys Gly Gly His Asn Ser Thr Met Cys Phe His Tyr Arg
        195                 200                 205

Asp Lys His Asn Ala Lys Gly Glu Ala Ile Phe Asn Phe Ile Leu Val
    210                 215                 220

Val Met Phe Trp Leu Ile Phe Leu Leu Ile Ile Leu Ser Tyr Ile Lys
225                 230                 235                 240

Ile Gly Lys Asn Leu Leu Arg Ile Ser Lys Arg Ser Lys Phe Pro
                245                 250                 255

Asn Ser Gly Lys Tyr Ala Thr Thr Ala Arg Asn Ser Phe Ile Val Leu
            260                 265                 270

Ile Ile Phe Thr Ile Cys Phe Val Pro Tyr His Ala Phe Arg Phe Ile
        275                 280                 285

Tyr Ile Ser Ser Gln Leu Asn Val Ser Ser Cys Tyr Trp Lys Glu Ile
    290                 295                 300

Val His Lys Thr Asn Glu Ile Met Leu Val Leu Ser Ser Phe Asn Ser
305                 310                 315                 320

Cys Leu Asp Pro Val Met Tyr Phe Leu Met Ser Ser Asn Ile Arg Lys
                325                 330                 335

Ile Met Cys Gln Leu Leu Phe Arg Arg Phe Gln Gly Glu Pro Ser Arg
            340                 345                 350

Ser Glu Ser Thr Ser Glu Phe Lys Pro Gly Tyr Ser Leu His Asp Thr
```

355                 360                 365
Ser Val Ala Val Lys Ile Gln Ser Ser Ser Lys Ser Thr
    370                 375                 380

<210> SEQ ID NO 2
<211> LENGTH: 1143
<212> TYPE: DNA
<213> ORGANISM: Human

<400> SEQUENCE: 2

| | | | |
|---|---|---|---|
| atgagaagtc ataccataac aatgacgaca acttcagtca gcagctggcc ttactcctcc | 60 |
| cacagaatgc gctttataac caatcatagc gaccaaccgc cacaaaactt ctcagcaaca | 120 |
| ccaaatgtta ctacctgtcc catggatgaa aaattgctat ctactgtgtt aaccacatcc | 180 |
| tactctgtta ttttcatcgt gggactggtt gggaacataa tcgccctcta tgtatttctg | 240 |
| ggtattcacc gtaaaagaaa ttccattcaa atttatctac ttaacgtagc cattgcagac | 300 |
| ctcctactca tcttctgcct cccttttcga ataatgtatc atattaacca aaacaagtgg | 360 |
| acactaggtg tgattctgtg caaggttgtg ggaacactgt tttatatgaa catgtacatt | 420 |
| agcattattt tgcttggatt catcagtttg gatcgctata taaaaattaa tcggtctata | 480 |
| cagcaacgga aggcaataac aaccaaacaa gtatttatg tctgttgtat agtatggatg | 540 |
| cttgctcttg gtggattcct aactatgatt attttaacac ttaagaaagg agggcataat | 600 |
| tccacaatgt gtttccatta cagagataag cataacgcaa aaggagaagc cattttaac | 660 |
| ttcattcttg tggtaatgtt ctggctaatt ttcttactaa taatcctttc atatattaag | 720 |
| attgggaaga atctattgag gatttctaaa aggaggtcaa aatttcctaa ttctggtaaa | 780 |
| tatgccacta cagctcgtaa ctcctttatt gtacttatca tttttactat atgttttgtt | 840 |
| ccctatcatg cctttcgatt catctacatt tcttcacagc taaatgtatc atcttgctac | 900 |
| tggaaagaaa ttgttcacaa aaccaatgag atcatgctgg ttctctcatc tttcaatagt | 960 |
| tgcttagatc cagtcatgta tttcctgatg tccagtaaca ttcgcaaaat aatgtgccaa | 1020 |
| cttctttta gacgatttca aggtgaacca gtaggagtg aaagcacttc agaatttaaa | 1080 |
| ccaggatact ccctgcatga tacatctgtg gcagtgaaaa tacagtctag ttctaaaagt | 1140 |
| act | 1143 |

<210> SEQ ID NO 3
<211> LENGTH: 27
<212> TYPE: DNA
<213> ORGANISM: Artificial Sequence
<220> FEATURE:
<223> OTHER INFORMATION: Designed oligonucleotide primer to amplify DNA
      encoding GPR34

<400> SEQUENCE: 3
atctgtcgac atgagaagtc ataccat                                     27

<210> SEQ ID NO 4
<211> LENGTH: 30
<212> TYPE: DNA
<213> ORGANISM: Artificial Sequence
<220> FEATURE:
<223> OTHER INFORMATION: Designed oligonucleotide primer to amplify DNA
      encoding GPR34

<400> SEQUENCE: 4
tatgactagt tcaagtactt ttagaactag                                  30

<210> SEQ ID NO 5
<211> LENGTH: 20
<212> TYPE: DNA
<213> ORGANISM: Artificial Sequence
<220> FEATURE:
<223> OTHER INFORMATION: Designed oligonucleotide primer to amplify DNA encoding GPR34

<400> SEQUENCE: 5
tcagtcagca gctggcctta                                          20

<210> SEQ ID NO 6
<211> LENGTH: 18
<212> TYPE: DNA
<213> ORGANISM: Artificial Sequence
<220> FEATURE:
<223> OTHER INFORMATION: Designed oligonucleotide primer to amplify DNA encoding GPR34

<400> SEQUENCE: 6
ggcggttggt cgctatga                                            18

<210> SEQ ID NO 7
<211> LENGTH: 28
<212> TYPE: DNA
<213> ORGANISM: Artificial Sequence
<220> FEATURE:
<223> OTHER INFORMATION: Designed oligonucleotide probe (labeled with FAM and TAMRA)

<400> SEQUENCE: 7
tcctcccaca gaatgcgctt tataacca                                 28

<210> SEQ ID NO 8
<211> LENGTH: 20
<212> TYPE: DNA
<213> ORGANISM: Artificial Sequence
<220> FEATURE:
<223> OTHER INFORMATION: Designed oligonucleotide primer to amplify DNA encoding rat GPR34

<400> SEQUENCE: 8
taaattctga agtgctttca                                          20

<210> SEQ ID NO 9
<211> LENGTH: 20
<212> TYPE: DNA
<213> ORGANISM: Artificial Sequence
<220> FEATURE:
<223> OTHER INFORMATION: Designed oligonucleotide primer to amplify DNA encoding rat GPR34

<400> SEQUENCE: 9
attcaccgta aaagaaattc                                          20

<210> SEQ ID NO 10
<211> LENGTH: 749
<212> TYPE: DNA
<213> ORGANISM: Rat

<400> SEQUENCE: 10
ggctgttgca gaccttctac tcatcttctg cctcccttc cgcataatgt atcacatcaa      60
ccaaaatagg tggacactag gtgtgattct ttgcaaagtt gtggggacac tatttttacat   120 gaacatgtac attagtatta ttctgcttgg gtttatcagt ttggatcgat atataaaaat    180

```
caaccggtct atacaacaaa gaagggcaat aaccaccaag caaagtgttt acgtttgctg     240
tgtagtctgg acagttgctc tagctggatt tttaacaatg atcattttga cactgaagaa     300
gggagggcac aattccacaa tgtgtttcca ttacagagat aagcataatg caaagggaga     360
agcgatcttt aactttgctc ttgtagtaat gttctggctc attttcctac tgataatcct     420
ttcatatatt aagattggca agaatctact gaggatttct aaaaggaggt caaaatttcc     480
taactctggc aaatatgcca cgacagcccg gaactccttc attgtactaa tcattttac      540 tatatgcttc gtgccttatc atgcctttcg attcatttac atttcttcac agctaaatgc     600
atcttcttgc tactggaagg aaatcattca taaaaccaat gagatcatgt tggttctctc     660
ctctttcaac agctgcttgg atcctgtcat gtatttccta atgtccagta atattcgcaa     720
aatcatgtgt caacttcttt ttagaagat                                       749

<210> SEQ ID NO 11
<211> LENGTH: 25
<212> TYPE: DNA
<213> ORGANISM: Artificial Sequence
<220> FEATURE:
<223> OTHER INFORMATION: Designed oligonucleotide primer to amplify DNA
      encoding rat GPR34

<400> SEQUENCE: 11
gcttcgtgcc ttatcatgcc tttcg                                            25

<210> SEQ ID NO 12
<211> LENGTH: 25
<212> TYPE: DNA
<213> ORGANISM: Artificial Sequence
<220> FEATURE:
<223> OTHER INFORMATION: Designed oligonucleotide primer to amplify DNA
      encoding rat GPR34

<400> SEQUENCE: 12
ctctcctctt tcaacagctg cttgg                                            25

<210> SEQ ID NO 13
<211> LENGTH: 300
<212> TYPE: DNA
<213> ORGANISM: Rat

<400> SEQUENCE: 13
ttcaaagtga cacaagcaga agtgaaagca cttcagaatt taagccagga tattccttgc      60
atgatctatc tgtgacggtc aaaatgcagt acagcactaa gggtaactga ggcacatgca     120
gtaaaatgaa caacataaac cagcctcttc attccttgag gttggtaaaa ttatggaaca     180
aattcctagc atgttcaaaa accagatctt tagaagtggt cttcacttg cttaactgca      240 aaatagttca aggcaaagaa aagcttacac taatccctag attttagaac tatatgtaga     300

<210> SEQ ID NO 14
<211> LENGTH: 24
<212> TYPE: DNA
<213> ORGANISM: Artificial Sequence
<220> FEATURE:
<223> OTHER INFORMATION: Designed oligonucleotide primer to amplify DNA
      encoding rat GPR34

<400> SEQUENCE: 14
gcccttcttt gttgtataga ccgg                                             24

<210> SEQ ID NO 15
```

<211> LENGTH: 26
<212> TYPE: DNA
<213> ORGANISM: Artificial Sequence
<220> FEATURE:
<223> OTHER INFORMATION: Designed oligonucleotide primer to amplify DNA
      encoding rat GPR34

<400> SEQUENCE: 15
gcaaagaatc acacctagtg tccacc                                          26

<210> SEQ ID NO 16
<211> LENGTH: 500
<212> TYPE: DNA
<213> ORGANISM: Rat

<400> SEQUENCE: 16
cggatggaag agtccagctg acacgacctg gtcgagggag ctttgggttt cctcctttac     60
ttcagcaaag cctcaactca gttcctgtga cttctgaagt atggcctgaa tagattcaat    120
cattattagt ccattatcat ataggaaaat ctgaagacac caagaagtat aaaaagcatg    180
tcatttagca ccctgtcctg atagttacag aagacattga aagttacag tgtaacaatg     240 acgactacag ttgacagctg gctttgctcc tctcctggaa tgcactttat aactaatgac    300
agtgaccaag tctcacaaaa tttctcagga gtgtcaaatg tcactagctg tccaatggat    360
gaaaaattac tgtctactgt gttaacaact ttctactctg tgatattcat cgtgggactg    420
gttggaaaca tcattgccct ttatgtattt ctgggcatcc accgcaaaag aaattccatt    480
caaatttatc tacttaatgt                                                500

<210> SEQ ID NO 17
<211> LENGTH: 20
<212> TYPE: DNA
<213> ORGANISM: Artificial Sequence
<220> FEATURE:
<223> OTHER INFORMATION: Designed oligonucleotide primer to amplify DNA
      encoding rat GPR34

<400> SEQUENCE: 17
tcagttaccc ttagtgctgt                                                 20

<210> SEQ ID NO 18
<211> LENGTH: 20
<212> TYPE: DNA
<213> ORGANISM: Artificial Sequence
<220> FEATURE:
<223> OTHER INFORMATION: Designed oligonucleotide primer to amplify DNA
      encoding rat GPR34

<400> SEQUENCE: 18
atgacgacta cagttgacag                                                 20

<210> SEQ ID NO 19
<211> LENGTH: 373
<212> TYPE: PRT
<213> ORGANISM: Rat

<400> SEQUENCE: 19

Met Thr Thr Thr Val Asp Ser Trp Leu Cys Ser Ser Pro Gly Met His
              5                  10                  15

Phe Ile Thr Asn Asp Ser Asp Gln Val Ser Gln Asn Phe Ser Gly Val
           20                  25                  30

Ser Asn Val Thr Ser Cys Pro Met Asp Glu Lys Leu Leu Ser Thr Val
        35                  40                  45

| Leu | Thr | Thr | Phe | Tyr | Ser | Val | Ile | Phe | Ile | Val | Gly | Leu | Val | Gly | Asn |
|---|---|---|---|---|---|---|---|---|---|---|---|---|---|---|---|
| | 50 | | | | | 55 | | | | 60 | | | | | |

| Ile | Ile | Ala | Leu | Tyr | Val | Phe | Leu | Gly | Ile | His | Arg | Lys | Arg | Asn | Ser |
|---|---|---|---|---|---|---|---|---|---|---|---|---|---|---|---|
| 65 | | | | 70 | | | | | 75 | | | | | | 80 |

| Ile | Gln | Ile | Tyr | Leu | Leu | Asn | Val | Ala | Val | Ala | Asp | Leu | Leu | Leu | Ile |
|---|---|---|---|---|---|---|---|---|---|---|---|---|---|---|---|
| | | | | 85 | | | | | 90 | | | | | 95 | |

| Phe | Cys | Leu | Pro | Phe | Arg | Ile | Met | Tyr | His | Ile | Asn | Gln | Asn | Arg | Trp |
|---|---|---|---|---|---|---|---|---|---|---|---|---|---|---|---|
| | | | 100 | | | | | 105 | | | | | 110 | | |

| Thr | Leu | Gly | Val | Ile | Leu | Cys | Lys | Val | Val | Gly | Thr | Leu | Phe | Tyr | Met |
|---|---|---|---|---|---|---|---|---|---|---|---|---|---|---|---|
| | | | 115 | | | | | 120 | | | | | 125 | | |

| Asn | Met | Tyr | Ile | Ser | Ile | Ile | Leu | Leu | Gly | Phe | Ile | Ser | Leu | Asp | Arg |
|---|---|---|---|---|---|---|---|---|---|---|---|---|---|---|---|
| | 130 | | | | | 135 | | | | | 140 | | | | |

| Tyr | Ile | Lys | Ile | Asn | Arg | Ser | Ile | Gln | Gln | Arg | Ala | Ile | Thr | Thr |
|---|---|---|---|---|---|---|---|---|---|---|---|---|---|---|
| 145 | | | | | 150 | | | | | 155 | | | | 160 |

| Lys | Gln | Ser | Val | Tyr | Val | Cys | Cys | Val | Val | Trp | Thr | Val | Ala | Leu | Ala |
|---|---|---|---|---|---|---|---|---|---|---|---|---|---|---|---|
| | | | | 165 | | | | | 170 | | | | | 175 | |

| Gly | Phe | Leu | Thr | Met | Ile | Ile | Leu | Thr | Leu | Lys | Lys | Gly | Gly | His | Asn |
|---|---|---|---|---|---|---|---|---|---|---|---|---|---|---|---|
| | | | | 180 | | | | | 185 | | | | | 190 | |

| Ser | Thr | Met | Cys | Phe | His | Tyr | Arg | Asp | Lys | His | Asn | Ala | Lys | Gly | Glu |
|---|---|---|---|---|---|---|---|---|---|---|---|---|---|---|---|
| | | 195 | | | | | 200 | | | | | 205 | | | |

| Ala | Ile | Phe | Asn | Phe | Ala | Leu | Val | Val | Met | Phe | Trp | Leu | Ile | Phe | Leu |
|---|---|---|---|---|---|---|---|---|---|---|---|---|---|---|---|
| | 210 | | | | | 215 | | | | | 220 | | | | |

| Leu | Ile | Ile | Leu | Ser | Tyr | Ile | Lys | Ile | Gly | Lys | Asn | Leu | Leu | Arg | Ile |
|---|---|---|---|---|---|---|---|---|---|---|---|---|---|---|---|
| 225 | | | | | 230 | | | | | 235 | | | | | 240 |

| Ser | Lys | Arg | Arg | Ser | Lys | Phe | Pro | Asn | Ser | Gly | Lys | Tyr | Ala | Thr | Thr |
|---|---|---|---|---|---|---|---|---|---|---|---|---|---|---|---|
| | | | | 245 | | | | | 250 | | | | | 255 | |

| Ala | Arg | Asn | Ser | Phe | Ile | Val | Leu | Ile | Ile | Phe | Thr | Ile | Cys | Phe | Val |
|---|---|---|---|---|---|---|---|---|---|---|---|---|---|---|---|
| | | | 260 | | | | | 265 | | | | | 270 | | |

| Pro | Tyr | His | Ala | Phe | Arg | Phe | Ile | Tyr | Ile | Ser | Ser | Gln | Leu | Asn | Ala |
|---|---|---|---|---|---|---|---|---|---|---|---|---|---|---|---|
| | | 275 | | | | | 280 | | | | | 285 | | | |

| Ser | Ser | Cys | Tyr | Trp | Lys | Glu | Ile | Ile | His | Lys | Thr | Asn | Glu | Ile | Met |
|---|---|---|---|---|---|---|---|---|---|---|---|---|---|---|---|
| | 290 | | | | | 295 | | | | | 300 | | | | |

| Leu | Val | Leu | Ser | Ser | Phe | Asn | Ser | Cys | Leu | Asp | Pro | Val | Met | Tyr | Phe |
|---|---|---|---|---|---|---|---|---|---|---|---|---|---|---|---|
| 305 | | | | | 310 | | | | | 315 | | | | | 320 |

| Leu | Met | Ser | Ser | Asn | Ile | Arg | Lys | Ile | Met | Cys | Gln | Leu | Leu | Phe | Arg |
|---|---|---|---|---|---|---|---|---|---|---|---|---|---|---|---|
| | | | | 325 | | | | | 330 | | | | | 335 | |

| Arg | Phe | Gln | Ser | Asp | Thr | Ser | Arg | Ser | Glu | Ser | Thr | Ser | Glu | Phe | Lys |
|---|---|---|---|---|---|---|---|---|---|---|---|---|---|---|---|
| | | | 340 | | | | | 345 | | | | | 350 | | |

| Pro | Gly | Tyr | Ser | Leu | His | Asp | Leu | Ser | Val | Thr | Val | Lys | Met | Gln | Tyr |
|---|---|---|---|---|---|---|---|---|---|---|---|---|---|---|---|
| | | | 355 | | | | | 360 | | | | | 365 | | |

| Ser | Thr | Lys | Gly | Asn |
|---|---|---|---|---|
| | 370 | | | |

<210> SEQ ID NO 20
<211> LENGTH: 1119
<212> TYPE: DNA
<213> ORGANISM: Rat

<400> SEQUENCE: 20

| | | | | |
|---|---|---|---|---|
| atgacgacta cagttgacag ctggctttgc tcctctcctg gaatgcactt tataactaat | | | | 60 |
| gacagtgacc aagtctcaca aaatttctca ggagtgtcaa atgtcactag ctgtccaatg | | | | 120 |
| gatgaaaaat tactgtctac tgtgttaaca actttctact ctgtgatatt catcgtggga | | | | 180 |
| ctggttggaa acatcattgc cctttatgta tttctgggca tccaccgcaa aagaaattcc | | | | 240 |

-continued

```
attcaaattt atctacttaa tgtggctgtt gcagaccttc tactcatctt ctgcctccct      300
ttccgcataa tgtatcacat caaccaaaat aggtggacac taggtgtgat tctttgcaaa      360
gttgtgggga cactatttta catgaacatg tacattagta ttattctgct tgggtttatc      420
agtttggatc gatatataaa aatcaaccgg tctatacaac aaagaagggc aataaccacc      480
aagcaaagtg tttacgtttg ctgtgtagtc tggacagttg ctctagctgg attttttaaca     540 atgatcattt tgacactgaa gaagggaggg cacaattcca caatgtgttt ccattacaga      600
gataagcata atgcaaaggg agaagcgatc tttaactttg ctcttgtagt aatgttctgg      660 ctcatttttcc tactgataat cctttcatat attaagattg caagaatct actgaggatt      720 tctaaaagga ggtcaaaatt tcctaactct ggcaaatatg ccacgacagc ccggaactcc      780
ttcattgtac taatcatttt tactatatgc ttcgtgcctt atcatgcctt tcgattcatt      840
tacatttctt cacagctaaa tgcatcttct tgctactgga aggaaatcat tcataaaacc      900
aatgagatca tgttggttct ctcctctttc aacagctgct ggatcctgt catgtatttc       960 ctaatgtcca gtaatattcg caaaatcatg tgtcaacttc tttttagaag atttcaaagt     1020
gacacaagca gaagtgaaag cacttcagaa tttaagccag gatattcctt gcatgatcta    1080
tctgtgacgg tcaaaatgca gtacagcact aagggtaac                            1119
```

<210> SEQ ID NO 21
<211> LENGTH: 1122
<212> TYPE: DNA
<213> ORGANISM: Rat

<400> SEQUENCE: 21

```
atgacgacta cagttgacag ctggctttgc tcctctcctg gaatgcactt tataactaat       60
gacagtgacc aagtctcaca aaatttctca ggagtgtcaa atgtcactag ctgtccaatg      120
gatgaaaaat tactgtctac tgtgttaaca actttctact ctgtgatatt catcgtggga      180
ctggttggaa acatcattgc cctttatgta tttctgggca tccaccgcaa agaaattcc       240 attcaaattt atctacttaa tgtggctgtt gcagaccttc tactcatctt ctgcctccct      300
ttccgcataa tgtatcacat caaccaaaat aggtggacac taggtgtgat tctttgcaaa      360
gttgtgggga cactatttta catgaacatg tacattagta ttattctgct tgggtttatc      420
agtttggatc gatatataaa aatcaaccgg tctatacaac aaagaagggc aataaccacc      480
aagcaaagtg tttacgtttg ctgtgtagtc tggacagttg ctctagctgg attttttaaca     540 atgatcattt tgacactgaa gaagggaggg cacaattcca caatgtgttt ccattacaga      600
gataagcata atgcaaaggg agaagcgatc tttaactttg ctcttgtagt aatgttctgg      660 ctcatttttcc tactgataat cctttcatat attaagattg caagaatct actgaggatt      720 tctaaaagga ggtcaaaatt tcctaactct ggcaaatatg ccacgacagc ccggaactcc      780
ttcattgtac taatcatttt tactatatgc ttcgtgcctt atcatgcctt tcgattcatt      840
tacatttctt cacagctaaa tgcatcttct tgctactgga aggaaatcat tcataaaacc      900
aatgagatca tgttggttct ctcctctttc aacagctgct ggatcctgt catgtatttc       960 ctaatgtcca gtaatattcg caaaatcatg tgtcaacttc tttttagaag atttcaaagt     1020
gacacaagca gaagtgaaag cacttcagaa tttaagccag gatattcctt gcatgatcta    1080
tctgtgacgg tcaaaatgca gtacagcact aagggtaact ga                        1122
```

<210> SEQ ID NO 22

-continued

```
<211> LENGTH: 375
<212> TYPE: PRT
<213> ORGANISM: Mouse

<400> SEQUENCE: 22

Met Thr Thr Thr Ser Val Asp Ser Trp Leu Cys Ser Ser His Gly Met
                  5                  10                  15

His Phe Ile Thr Asn Tyr Ser Asp Gln Ala Ser Gln Asn Phe Ser Gly
             20                  25                  30

Val Pro Asn Val Thr Ser Cys Pro Met Asp Glu Lys Leu Leu Ser Thr
             35                  40                  45

Val Leu Thr Thr Phe Tyr Ser Val Ile Phe Leu Val Gly Leu Val Gly
         50                  55                  60

Asn Ile Ile Ala Leu Tyr Val Phe Leu Gly Ile His Arg Lys Arg Asn
65                  70                  75                  80

Ser Ile Gln Ile Tyr Leu Leu Asn Val Ala Val Ala Asp Leu Leu Leu
                 85                  90                  95

Ile Phe Cys Leu Pro Phe Arg Ile Met Tyr His Ile Asn Gln Asn Lys
                100                 105                 110

Trp Thr Leu Gly Val Ile Leu Cys Lys Val Val Gly Thr Leu Phe Tyr
                115                 120                 125

Met Asn Met Tyr Ile Ser Ile Ile Leu Leu Gly Phe Ile Ser Leu Asp
            130                 135                 140

Arg Tyr Ile Lys Ile Asn Arg Ser Ile Gln Gln Arg Ala Ile Thr
145                 150                 155                 160

Thr Lys Gln Ser Ile Tyr Val Cys Cys Ile Val Trp Thr Val Ala Leu
                165                 170                 175

Ala Gly Phe Leu Thr Met Ile Ile Leu Thr Leu Lys Lys Gly Gly His
                180                 185                 190

Asn Ser Thr Met Cys Phe His Tyr Arg Asp Arg His Asn Ala Lys Gly
                195                 200                 205

Glu Ala Ile Phe Asn Phe Val Leu Val Val Met Phe Trp Leu Ile Phe
210                 215                 220

Leu Leu Ile Ile Leu Ser Tyr Ile Lys Ile Gly Lys Asn Leu Leu Arg
225                 230                 235                 240

Ile Ser Lys Arg Arg Ser Lys Phe Pro Asn Ser Gly Lys Tyr Ala Thr
                245                 250                 255

Thr Ala Arg Asn Ser Phe Ile Val Leu Ile Ile Phe Thr Ile Cys Phe
                260                 265                 270

Val Pro Tyr His Ala Phe Arg Phe Ile Tyr Ile Ser Ser Gln Leu Asn
                275                 280                 285

Val Ser Ser Cys Tyr Trp Lys Glu Ile Ile His Lys Thr Asn Glu Ile
            290                 295                 300

Met Leu Val Phe Ser Ser Phe Asn Ser Cys Leu Asp Pro Val Met Tyr
305                 310                 315                 320

Phe Leu Met Ser Ser Asn Ile Arg Lys Ile Met Cys Gln Leu Leu Phe
                325                 330                 335

Arg Arg Phe Gln Ser Glu Ala Ser Arg Ser Glu Ser Thr Ser Glu Phe
                340                 345                 350

Lys Pro Gly His Ser Leu His Asp Leu Ser Val Thr Val Lys Met Pro
                355                 360                 365

Gln Tyr Ser Thr Lys Gly Asn
            370                 375
```

```
<210> SEQ ID NO 23
<211> LENGTH: 1125
<212> TYPE: DNA
<213> ORGANISM: Mouse

<400> SEQUENCE: 23
atgactacta cttcagttga cagctggctt tgctcctctc atggaatgca ctttataact      60
aattatagtg accaagcctc acaaaatttc tcaggagtgc caaatgtcac tagctgtcca     120
atggatgaaa aattactatc tactgtgtta acaaccttct actctgttat attcctcgtg     180
ggactggttg gaaacatcat tgccctctat gtatttctgg gcattcaccg taaaagaaat     240
tccattcaaa tttatctact taatgtggct gttgcagacc ttctactcat cttctgcctc     300
cctttccgca taatgtatca catcaaccaa aacaagtgga cactaggtgt gattctttgt     360
aaagttgtgg ggacactatt ttacatgaac atgtacatta gcattatttt gcttgggttt     420
atcagtttgg atcgctatat aaaaatcaat cggtctatac aacaaagaag ggcaataacc     480
accaagcaaa gtatttatgt ttgctgtata gtatggacgg ttgctcttgc tggatttcta     540
actatgatca ttttgacact gaagaaggga ggtcataatt ccacaatgtg tttccattac     600
agagacagac ataatgcaaa gggagaagca attttttaact ttgttcttgt agtaatgttc     660
tggcttattt tcctactgat aatcctctca tatattaaga ttggcaagaa tctactgagg     720
atttctaaac ggaggtcaaa atttccaaac tctggcaaat atgctacaac agcccggaac     780
tcctttattg tactgatcat ttttactata tgctttgtgc cttaccatgc ctttcggttc     840
atttacattt cttcacagct aaatgtgtcc tcttgttatt ggaaggaaat cattcacaaa     900
actaacgaga tcatgctggt tttctcctct ttcaacagtt gcctggatcc tgtcatgtat     960
ttcctgatgt ccagtaatat tcgcaaaatc atgtgtcaac ttcttttttag aaggtttcaa    1020 agtgaagcaa gcagaagtga aagcacttca gaatttaagc caggacattc cttgcatgat    1080
ctgtccgtga cagtcaaaat gccccagtac agcactaagg gtaat                    1125
```